(12) United States Patent  
Tearney et al.

(10) Patent No.: US 7,231,243 B2  
(45) Date of Patent: Jun. 12, 2007

(54) OPTICAL METHODS FOR TISSUE ANALYSIS

(75) Inventors: Guillermo J. Tearney, Cambridge, MA (US); Brett E. Bouma, Quincy, MA (US)

(73) Assignee: The General Hospital Corporation, Boston, MA (US)

( * ) Notice: Subject to any disclaimer, the term of this patent is extended or adjusted under 35 U.S.C. 154(b) by 563 days.

(21) Appl. No.: 10/016,244

(22) Filed: Oct. 30, 2001

(65) Prior Publication Data

US 2002/0183601 A1 Dec. 5, 2002

Related U.S. Application Data

(60) Provisional application No. 60/244,255, filed on Oct. 30, 2000.

(51) Int. Cl.
*A61B 5/00* (2006.01)

(52) U.S. Cl. ............. 600/407; 600/476; 600/477; 600/479

(58) Field of Classification Search ......... 600/310, 600/473, 160, 182, 407, 475–479; 356/450, 356/457, 496, 498, 503, 511; 250/450, 496
See application file for complete search history.

(56) References Cited

U.S. PATENT DOCUMENTS

| | | | |
|---|---|---|---|
| 2,339,754 A | 1/1944 | Brace | |
| 4,295,738 A | 10/1981 | Meltz et al. | |
| 4,300,816 A | 11/1981 | Snitzer et al. | |
| 4,585,349 A | 4/1986 | Gross et al. | |
| 4,601,036 A | 7/1986 | Faxvog et al. | |
| 4,631,498 A | 12/1986 | Cutler | |
| 4,770,492 A | 9/1988 | Levin et al. | |
| 4,868,834 A | 9/1989 | Fox et al. | |
| 4,925,302 A | 5/1990 | Cutler | |
| 4,928,005 A | 5/1990 | Lefèvre et al. | |
| 4,965,441 A | 10/1990 | Picard | |
| 4,993,834 A | 2/1991 | Carlhoff et al. | |
| 5,039,193 A | 8/1991 | Snow et al. | |
| 5,040,889 A | 8/1991 | Keane | |
| 5,045,936 A | 9/1991 | Lobb et al. ............. 358/100 |
| 5,046,501 A | 9/1991 | Crilly | |
| 5,065,331 A * | 11/1991 | Vachon et al. ............. 356/35.5 |
| 5,120,953 A | 6/1992 | Harris | |
| 5,127,730 A | 7/1992 | Brelje et al. | |
| 5,197,470 A | 3/1993 | Helfer et al. | |
| 5,202,745 A | 4/1993 | Sorin et al. | |

(Continued)

FOREIGN PATENT DOCUMENTS

DE  4309056  9/1994

(Continued)

OTHER PUBLICATIONS

Boas et al., "Diffusing temporal light correlation for burn diagnosis," *SPIE*, 2979:468-477, 1999.

(Continued)

*Primary Examiner*—Ruth S. Smith
(74) *Attorney, Agent, or Firm*—Dorsey & Whitney LLP

(57) ABSTRACT

The invention relates to methods and systems to optically analyze samples such as tissue based on speckle patterns of microscopic motion, such as Brownian motion.

50 Claims, 7 Drawing Sheets

U.S. PATENT DOCUMENTS

| | | |
|---|---|---|
| 5,248,876 A | 9/1993 | Kerstens et al. |
| 5,262,644 A | 11/1993 | Maguire |
| 5,291,885 A | 3/1994 | Taniji et al. .............. 128/633 |
| 5,293,872 A | 3/1994 | Alfano et al. |
| 5,293,873 A | 3/1994 | Fang ...................... 128/664 |
| 5,304,810 A | 4/1994 | Amos |
| 5,305,759 A | 4/1994 | Kaneko et al. |
| 5,317,389 A | 5/1994 | Hochberg et al. |
| 5,321,501 A | 6/1994 | Swanson et al. |
| 5,353,790 A | 10/1994 | Jacques et al. |
| 5,383,467 A | 1/1995 | Auer et al. |
| 5,419,323 A | 5/1995 | Kittrell et al. |
| 5,439,000 A | 8/1995 | Gunderson et al. |
| 5,441,053 A | 8/1995 | Lodder et al. |
| 5,450,203 A | 9/1995 | Penkethman |
| 5,459,325 A | 10/1995 | Hueton et al. |
| 5,459,570 A | 10/1995 | Swanson et al. |
| 5,465,147 A | 11/1995 | Swanson |
| 5,486,701 A | 1/1996 | Norton et al. |
| 5,491,524 A | 2/1996 | Hellmuth et al. |
| 5,491,552 A | 2/1996 | Kittrell |
| 5,526,338 A | 6/1996 | Hasman et al. |
| 5,562,100 A | 10/1996 | Kittrell et al. |
| 5,565,986 A | 10/1996 | Knüttel |
| 5,583,342 A | 12/1996 | Ichie |
| 5,590,660 A | 1/1997 | MacAulay et al. |
| 5,600,486 A | 2/1997 | Gal et al. |
| 5,601,087 A | 2/1997 | Gunderson et al. |
| 5,623,336 A | 4/1997 | Raab et al. |
| 5,697,373 A | 12/1997 | Richards-Kortum et al. |
| 5,698,397 A | 12/1997 | Zarling et al. |
| 5,710,630 A | 1/1998 | Essenpreis et al. |
| 5,719,399 A | 2/1998 | Alfano et al. |
| 5,735,276 A * | 4/1998 | Lemelson ................. 600/407 |
| 5,748,598 A | 5/1998 | Swanson et al. |
| 5,784,352 A | 7/1998 | Swanson et al. |
| 5,785,651 A | 7/1998 | Kuhn et al. |
| 5,795,295 A | 8/1998 | Hellmuth et al. |
| 5,803,082 A | 9/1998 | Stapleton et al. |
| 5,807,261 A | 9/1998 | Benaron et al. |
| 5,817,144 A | 10/1998 | Gregory |
| 5,840,023 A | 11/1998 | Oraevsky et al. |
| 5,842,995 A | 12/1998 | Mahadevan-Jansen et al. |
| 5,843,000 A | 12/1998 | Nishioka et al. |
| 5,847,827 A | 12/1998 | Fercher |
| 5,865,754 A | 2/1999 | Sevick-Muraca et al. |
| 5,871,449 A | 2/1999 | Brown |
| 5,877,856 A | 3/1999 | Fercher |
| 5,887,009 A | 3/1999 | Mandella et al. |
| 5,920,373 A | 7/1999 | Bille |
| 5,920,390 A | 7/1999 | Farahi et al. |
| 5,921,926 A | 7/1999 | Rolland et al. |
| 5,949,929 A | 9/1999 | Hamm |
| 5,951,482 A | 9/1999 | Winston et al. |
| 5,956,355 A | 9/1999 | Swanson et al. |
| 5,968,064 A | 10/1999 | Selmon et al. |
| 5,983,125 A | 11/1999 | Alfano et al. |
| 5,987,346 A | 11/1999 | Benaron et al. |
| 5,991,697 A | 11/1999 | Nelson et al. |
| 5,994,690 A | 11/1999 | Kulkarni et al. |
| 6,002,480 A | 12/1999 | Izatt et al. |
| 6,004,314 A | 12/1999 | Wei et al. |
| 6,006,128 A | 12/1999 | Izatt et al. |
| 6,010,449 A | 1/2000 | Selmon et al. |
| 6,033,721 A | 3/2000 | Nassuphis |
| 6,044,288 A | 3/2000 | Wake et al. |
| 6,048,742 A | 4/2000 | Weyburne et al. |
| 6,053,613 A | 4/2000 | Wei et al. |
| 6,069,698 A | 5/2000 | Ozawa et al. |
| 6,091,984 A | 7/2000 | Perelman et al. |
| 6,111,645 A | 8/2000 | Tearney et al. |
| 6,117,128 A | 9/2000 | Gregory |
| 6,120,516 A | 9/2000 | Selmon et al. |
| 6,134,003 A | 10/2000 | Tearney et al. |
| 6,134,010 A | 10/2000 | Zavislan |
| 6,141,577 A * | 10/2000 | Rolland et al. .............. 600/407 |
| 6,151,522 A | 11/2000 | Alfano et al. |
| 6,159,445 A | 12/2000 | Klaveness et al. |
| 6,160,826 A | 12/2000 | Swanson et al. |
| 6,161,031 A | 12/2000 | Hochman et al. |
| 6,166,373 A | 12/2000 | Mao |
| 6,175,669 B1 | 1/2001 | Colston et al. |
| 6,185,271 B1 | 2/2001 | Kinsinger |
| 6,191,862 B1 | 2/2001 | Swanson et al. |
| 6,193,676 B1 | 2/2001 | Winston et al. |
| 6,198,956 B1 * | 3/2001 | Dunne ........................ 600/407 |
| 6,201,989 B1 | 3/2001 | Whitehead et al. |
| 6,208,415 B1 | 3/2001 | De Boer et al. |
| 6,208,887 B1 | 3/2001 | Clarke |
| 6,263,234 B1 | 7/2001 | Engelhardt et al. |
| 6,282,011 B1 | 8/2001 | Tearney et al. |
| 6,308,092 B1 | 10/2001 | Hoyns |
| 6,324,419 B1 * | 11/2001 | Guzelsu et al. ............. 600/476 |
| 6,341,036 B1 | 1/2002 | Tearney et al. |
| 6,353,693 B1 | 3/2002 | Kano et al. |
| 6,377,349 B1 | 4/2002 | Fercher |
| 6,393,312 B1 | 5/2002 | Hoyns |
| 6,394,964 B1 | 5/2002 | Sievert, Jr. et al. |
| 6,421,164 B2 | 7/2002 | Tearney et al. |
| 6,445,944 B1 | 9/2002 | Ostrovsky |
| 6,463,313 B1 | 10/2002 | Winston et al. |
| 6,469,846 B2 | 10/2002 | Ebizuka et al. |
| 6,485,413 B1 | 11/2002 | Boppart et al. |
| 6,485,482 B1 | 11/2002 | Belef |
| 6,501,551 B1 | 12/2002 | Tearney et al. |
| 6,549,801 B1 | 4/2003 | Chen et al. |
| 6,552,796 B2 | 4/2003 | Magnin et al. |
| 6,558,324 B1 | 5/2003 | Von Behren et al. |
| 6,564,087 B1 | 5/2003 | Pitris et al. |
| 6,564,089 B2 * | 5/2003 | Izatt et al. ................... 600/478 |
| 6,622,732 B2 | 9/2003 | Constantz |
| 6,680,780 B1 | 1/2004 | Fee |
| 6,685,885 B2 | 2/2004 | Nolte et al. |
| 6,687,007 B1 | 2/2004 | Meigs |
| 6,687,010 B1 | 2/2004 | Horii et al. |
| 6,806,963 B1 | 10/2004 | Wälti et al. |
| 6,816,743 B2 * | 11/2004 | Moreno et al. ............. 600/473 |
| 6,980,299 B1 | 12/2005 | de Boer |
| 2001/0047137 A1 * | 11/2001 | Moreno et al. ............. 600/475 |
| 2002/0016533 A1 * | 2/2002 | Marchitto et al. .......... 600/310 |
| 2002/0122246 A1 | 9/2002 | Tearney et al. |
| 2002/0161357 A1 | 10/2002 | Rox et al. |
| 2002/0163622 A1 | 11/2002 | Magnin et al. |
| 2002/0196446 A1 | 12/2002 | Roth et al. |
| 2002/0198457 A1 | 12/2002 | Tearney et al. |
| 2003/0023153 A1 | 1/2003 | Izatt et al. |
| 2003/0026735 A1 | 2/2003 | Nolte et al. |
| 2003/0135101 A1 | 7/2003 | Webler |
| 2003/0236443 A1 | 12/2003 | Cespedes et al. |
| 2004/0150829 A1 | 8/2004 | Koch et al. |
| 2004/0166593 A1 | 8/2004 | Nolte et al. |

FOREIGN PATENT DOCUMENTS

| | | |
|---|---|---|
| DE | 19542955 | 5/1997 |
| EP | 0110201 | 6/1984 |
| EP | 0251062 | 1/1988 |
| EP | 1426799 | 6/2004 |
| GB | 2209221 | 5/1989 |
| JP | 4135550 | 5/1992 |
| JP | 4135551 | 5/1992 |
| WO | 9219930 | 11/1992 |
| WO | 9303672 | 3/1993 |
| WO | 9533971 | 12/1995 |

| | | |
|---|---|---|
| WO | 9732182 | 9/1997 |
| WO | 9814132 | 4/1998 |
| WO | 9835203 | 8/1998 |
| WO | 9848838 | 11/1998 |
| WO | 9944089 | 9/1999 |
| WO | 9957507 | 11/1999 |
| WO | 0058766 | 10/2000 |
| WO | 0138820 | 5/2001 |
| WO | 0142735 | 6/2001 |
| WO | 0236015 | 5/2002 |
| WO | 0238040 | 5/2002 |
| WO | 0254027 | 7/2002 |
| WO | 0 3020119 | 3/2003 |
| WO | 03062802 | 7/2003 |
| WO | 0 4105598 | 12/2004 |

OTHER PUBLICATIONS

Briers, J. David, "Speckle fluctuations and biomedical optics: implications and applications," *Optical Engineering*, 32(2):277-283, 1993.

Clark et al., "Tracking Speckle Patterns with Optical Correlation," *SPIE*, 1772:77-87, 1992.

Facchini et al., "An endoscopic system for DSPI," *Optik*, 95(1):27-30, 1993.

Hrabovsky, M., "Theory of speckle dispacement and decorrelation: application in mechanics," *SPIE*, 3479:345-354, 1998.

Kirkpatrick, Sean J. and Brooks, Brent W., "Micromechanical behavior of cortical bone as inferred from laser speckle data," *Journal of Biomedical Materials Research*, 39(3):373-379, 1998.

Kirkpatrick, Sean J. and Cipolla, Marilyn J., "Laser speckle microstrain measurement in vascular tissue," *SPIE*, 3598:121-129, 1999.

Loree et al., "Mechanical Properties of Model Atherosclerotic Lesion Lipid Pools," *Arteriosclerosis and Thrombosis*, 14(2):230-234, 1994.

Podbielska, H., "Interferometric Methods and Biomedical Research," *SPIE*, 2732:134-141, 1999.

Richards-Kortum et al., "Spectral diagnosis of atherosclerosis using an optical fiber laser catheter," American Heart Journal, 118(2):381-391, 1989.

Ruth, B., "Blood flow determination by the laser speckle method," *Int J Microcirc: Clin Exp*, 9:21-45, 1990.

Shapo et al., "Intravascular Strain Imaging: Experiments on an Inhomogeneous Phantom," *1996 IEEE Ultrasonics Symposium*, 2:1177-1180, 1996.

Shapo et al., "Ultrasonic Displacement and Strain Imaging of Coronary Arteries with a Catheter Array," 1995 IEEE Ultrasoncis Symposium, 2:1511-1514, 1995.

Thompson et al., "Imaging in scattering media by use of laser speckle," *Opt. Soc. Am. A.*, 14(9):2269-2277, 1997.

Thompson et al., "Diffusive media characterization with laser speckle," *Applied Optics*, 36(16):3726-3734, 1997.

Tuchin, Valery V., "Coherent Optical Techniques for the Analysis of Tissue Structure and Dynamics," *Journal of Biomedical Optics*, 4(1):106-124, 1999.

Wussling, M. and Schenk, W., "Laser diffraction and speckling studies in skeletal and heart muscle," *Biomed. Biochim. Acta*, 45(1/2):S 23-S 27, 1986.

Yoshimura, T., "Statistical properties of dynamic speckles," *J. Opt. Soc. Am. A.*, 3(7):1032-1054, 1986.

Zimnyakov et al., "Spatial speckle correlometry in applications to tissue structure monitoring," *Applied Optics*, 36(22):5594-5607, 1997.

Zimnyakov et al., "A Study of Statistical Properties of Partially Developed Speckle Fields as Applied to the Diagnostics of Structural Changes in Human Skin," *Optics and Spectroscopy*, 76(5):747-753, 1994.

Zimnyakov et al., "Speckle patterns polarization analysis as an approach to turbid tissue structure monitoring," *SPIE*, 2981:172-180, 1999.

D. Fu et al., "Non-invasive quantitative reconstruction of tissue elasticity using an iterative forward approach", Phys. Med. Biol. 2000 (45): 1495-1509.

S.B. Adams Jr. et al., "The use of polarization sensitive optical coherence tomography and elastography to assess connective tissue", Optical Soc. of American Washington 2002, p. 3.

International Search Report for International Patent application No. PCT/US2005/039740.

International Written Opinion for International Patent application No. PCT/US2005/039740.

International Search Report for International Patent application No. PCT/US2005/030294.

Fujimoto et al., "High Resolution in Vivo Intra-Arterial Imaging with Optical Coherence Tomography," *Official Journal of the British Cardiac Society*, vol. 82, pp. 128-133 Heart, 1999.

D. Huang et al., "Optical Coherence Tomography," *SCIENCE*, vol. 254, pp. 1178-1181, Nov. 1991.

Tearney et al., "High-Speed Phase—and Group Delay Scanning with a Grating Based Phase Control Delay Line," *Optics Letters*, vol. 22, pp. 1811-1813, Dec. 1997.

Rollins, et al., "In Vivo Video Rate Optical Coherence Tomography," *Optics Express*, vol. 3, pp. 219-229, Sep. 1998.

Saxer, et al., High Speed Fiber-Based Polarization-Sensitive Optical Coherence Tomography of in Vivo Human Skin, *Optical Society of America*, vol. 25, pp. 1355-1357, Sep. 2000.

Oscar Eduardo Martinez, "3000 Times Grating Compress or with Positive Group Velocity Dispersion," *IEEE*, vol. QE-23, pp. 59-64, Jan. 1987.

Kulkarni, et al., "Image Enhancement in Optical Coherence Tomography Using Deconvolution," *Electronics Letters*, vol. 33, pp. 1365-1367, Jul. 1997.

Bashkansky, et al., "Signal Processing for Improving Field Cross-Correlation Function in Optical Coherence Tomography," *Optics & Photonics News*, vol. 9, pp. 8137-8138, May 1998.

Yung et al., "Phase-Domain Processing of Optical Coherence Tomography Images," *Journal of Biomedical Optics*, vol. 4, pp. 125-136, Jan. 1999.

Tearney, et al., "In Vivo Endoscopic Optical Biopsy with Optical Coherence Tomography," *SCIENCE*, vol. 276, Jun. 1997.

W. Drexler et al., "In Vivo Ultrahigh-Resolution Optical Coherence Tomography," *Optics Letters* vol. 24, pp. 1221-1223, Sep. 1999.

Nicusor V. Iftimia et al., "A Portable, Low Coherence Interferometry Based Instrument for Fine Needle Aspiration Biopsy Guidance," Accepted to Review of Scientific Instruments, 2005.

Abbas, G.L., V.W.S. Chan et al., "Local-Oscillator Excess-Noise Suppression for Homodyne and Heterodyne-Detection," *Optics Letters*, vol. 8, pp. 419-421, Aug. 1983 issue.

Agrawal, G.P., "Population Pulsations and Nondegenerate 4-Wave Mixing in Semiconductor-Lasers and Amplifiers," *Journal Of The Optical Society Of America B-Optical Physics*, vol. 5, pp. 147-159, Jan. 1998.

Andretzky, P. et al., "Optical Coherence Tomography by Spectral Radar: Improvement of Signal-to-Noise Ratio," *The International Society for Optical Engineering, USA*, vol. 3915, 2000.

Ballif, J. et al., "Rapid and Scalable Scans at 21 m/s in optical Low-Coherence Reflectometry," *Optics Letters*, vol. 22, pp. 757-759, Jun. 1997.

Barfuss H. et al., "Modified Optical Frequency-Domain Reflectometry with High Spatial-Resolution for Components of Integrated Optic Systems," *Journal Of Lightwave Technology*, vol. 7, pp. 3-10, Jan. 1989.

Beaud, P. et al., "Optical Reflectometry with Micrometer Resolution for the Investigation of Integrated Optical-Devices," *Ieee Journal of Quantum Electronics*, vol. 25, pp. 755-759, Apr. 1989.

Bouma, Brett et al., "Power-Efficient Nonreciprocal Interferometer and Linear-Scanning Fiber-Optic Catheter for Optical Coherence Tomography," *Optics Letters*, vol. 24, pp. 531-533, Apr. 1999.

Brinkmeyer, E. et al., "Efficient Algorithm for Non-Equidistant Interpolation of Sampled Data," *Electronics Letters*, vol. 28, p. 693, Mar. 1992.

Brinkmeyer, E. et al., "High-Resolution OCDR in Dispersive Wave-Guides," *Electronics Letters*, vol. 26, pp. 413-414, Mar. 1990.

Chinn, S.R. et al., "Optical Coherence Tomography Using a Frequency-Tunable Optical Source," *Optics Letters*, vol. 22, pp. 340-342, Mar. 1997.
Danielson, B.L. et al., "Absolute Optical Ranging Using Low Coherence Interferometry," *Applied Optics*, vol. 30, p. 2975, Jul. 1991.
Dorrer, C. et al., "Spectral Resolution and Sampling Issues in Fourier-Transform Spectral Interferometry," *Journal of the Optical Society of America B-Optical Physics*, vol. 17, pp. 1795-1802, Oct. 2000.
Dudley, J.M. et al., "Cross-Correlation Frequency Resolved Optical Gating Analysis of Broadband Continuum Generation in Photonic Crystal Fiber: Simulations and Experiments," *Optics Express*, vol. 10, p. 1215, Oct. 2002.
Eickhoff, W. et al., "Optical Frequency-Domain Reflectometry in Single-Mode Fiber," *Applied Physics Letters*, vol. 39, pp. 693-695, 1981.
Fercher, Adolf "Optical Coherence Tomography," *Journal of Biomedical Optics*, vol. 1, pp. 157-173, Apr. 1996.
Ferreira, L.A. et al., "Polarization-Insensitive Fiberoptic White-Light Interferometry," *Optics Communications*, vol. 114, pp. 386-392, Feb. 1995.
Fujii, Yohji, "High-Isolation Polarization-Independent Optical Circulator", *Journal of Lightwave Technology*, vol. 9, pp. 1239-1243, Oct. 1991.
Glance, B., "Polarization Independent Coherent Optical Receiver," *Journal of Lightwave Technology*, vol. LT-5, p. 274, Feb. 1987.
Glombitza, U., "Coherent Frequency-Domain Reflectometry for Characterization of Single-Mode Integrated-Optical Wave-Guides," *Journal of Lightwave Technology*, vol. 11, pp. 1377-1384, Aug. 1993.
Golubovic, B. et al., "Optical Frequency-Domain Reflectometry Using Rapid Wavelength Tuning of a Cr4+:Forsterite Laser," *Optics Letters*, vol. 11, pp. 1704-1706, Nov. 1997.
Haberland, U. H. P. et al., "Chirp Optical Coherence Tomography of Layered Scattering Media," *Journal of Biomedical Optics*, vol. 3, pp. 259-266, Jul. 1998.
Hammer, Daniel X. et al., "Spectrally Resolved White-Light Interferometry for Measurement of Ocular Dispersion," *Journal of the Optical Society of America A-Optics Image Science and Vision*, vol. 16, pp. 2092-2102, Sep. 1999.
Harvey, K. C. et al., "External-Cavity Diode-Laser Using a Grazing-Incidence Diffraction Grating," *Optics Letters*, vol. 16, pp. 910-912, Jun. 1991.
Hausler, Gerd et al., "'Coherence Radar' and 'Spectral Radar' New Tools for Dermatological Diagnosis," *Journal of Biomedical Optics*, vol. 3, pp. 21-31, Jan. 1998.
Hee, Michael R. et al., "Polarization-Sensitive Low-Coherence Reflectometer for Birefringence Characterization and Ranging," *Journal of the Optical Society of America B(Optical Physics)*, vol. 9, p. 903-908, Jun. 1992.
Hotate Kazuo et al., "Optical Coherence Domain Reflectometry by Synthesis of Coherence Function," *Journal of Lightwave Technology*, vol. 11, pp. 1701-1710, Oct. 1993.
Inoue, Kyo et al., "Nearly Degenerate 4-Wave-Mixing in a Traveling-Wave Semiconductor-Laser Amplifier," *Applied Physics Letters*, vol. 51, pp. 1051-1053, 1987.
Ivanov, A. P. et al., "New Method for High-Range Resolution Measurements of Light Scattering in Optically Dense Inhomogeneous Media," *Optics Letters*, vol. 1, pp. 226-228, Dec. 1977.
Ivanov, A. P. et al., "Interferometric Study of the Spatial Structure of a Light-Scattering Medium," *Journal of Applied Spectroscopy*, vol. 28, pp. 518-525, 1978.
Kazovsky, L. G. et al., "Heterodyne Detection Through Rain, Snow, and Turbid Media: Effective Receiver Size at Optical Through Millimeter Wavelenghths," *Applied Optics*, vol. 22, pp. 706-710, Mar. 1983.
Kersey, A. D. et al., "Adaptive Polarization Diversity Receiver Configuration for Coherent Optical Fiber Communications," *Electronics Letters*, vol. 25, pp. 275-277, Feb. 1989.
Kohlhaas, Andreas et al., "High-Resolution OCDR for Testing Integrated-Optical Waveguides: Dispersion-Corrupted Experimental Data Corrected by a Numerical Algorithm," *Journal of Lightwave Technology*, vol. 9, pp. 1493-1502, Nov. 1991.
Larkin, Kieran G., "Efficient Nonlinear Algorithm for Envelope Detection in White Light Interferometry," *Journal of the Optical Society of America A-Optics Image Science and Vision*, vol. 13, pp. 832-843, Apr. 1996.
Leitgeb, R. et al., "Spectral measurement of Absorption by Spectroscopic Frequency-Domain Optical Coherence Tomography," *Optics Letters*, vol. 25, pp. 820-822, Jun. 2000.
Lexer, F. et al., "Wavelength-Tuning Interferometry of Intraocular Distances," *Applied Optics*, vol. 36, pp. 6548-6553, Sep. 1997.
Mitsui, Takahisa, "Dynamic Range of Optical Reflectometry with Spectral Interferometry," *Japanese Journal of Applied Physics Part 1-Regular Papers Short Notes & Review Papers*, vol. 38, pp. 6133-6137, 1999.
Naganuma, Kazunori et al., "Group-Delay Measurement Using the Fourier-Transform of an Interferometric Cross-Correlation Generated by White Light," *Optics Letters*, vol. 15, pp. 393-395, Apr. 1990.
Okoshi, Takanori, "Polarization-State Control Schemes for Heterodyne or Homodyne Optical Fiber Communications," *Journal of Lightwave Technology*, vol. LT-3, pp. 1232-1237, Dec. 1995.
Passy, R. et al., "Experimental and Theoretical Investigations of Coherent OFDR with Semiconductor-Laser Sources," *Journal of Lightwave Technology*, vol. 12, pp. 1622-1630, Sep. 1994.
Podoleanu, Adrian G., "Unbalanced Versus Balanced Operation in an Optical Coherence Tomography System," *Applied Optics*, vol. 39, pp. 173-182, Jan. 2000.
Price, J. H. V. et al., "Tunable, Femtosecond Pulse Source Operating in the Range 1.06-1.33 mu m Based on an Yb3+-doped Holey Fiber Amplifier," *Journal of the Optical Society of America B-Optical Physics*, vol. 19, pp. 1286-1294, Jun. 2002.
Schmitt, J. M. et al, "Measurement of Optical-Properties of Biological Tissues By Low-Coherence Reflectometry," *Applied Optics*, vol. 32, pp. 6032-6042, Oct. 1993.
Silberberg, Y. et al., "Passive-Mode Locking of a Semiconductor Diode-Laser," *Optics Letters*, vol. 9, pp. 507-509, Nov. 1984.
Smith, L. Montgomery et al., "Absolute Displacement Measurements Using Modulation of the Spectrum of White-Light in a Michelson Interferometer," *Applied Optics*, vol. 28, pp. 3339-3342, Aug. 1989.
Sonnenschein, C. M. et al., "Signal-To-Noise Relationships for Coaxial Systems that Heterodyne Backscatter from Atmosphere," *Applied Optics*, vol. 10, pp. 1600-1604, Jul. 1971.
Sorin, W. V. et al., "Measurement of Rayleigh Backscattering at 1.55 mu m with 32 mu m Spatial Resolution," *IEEE Photonics Technology Letters*, vol. 4, pp. 374-376, Apr. 1992.
Sorin, W. V. et al., "A Simple Intensity Noise-Reduction Technique for Optical Low-Coherence Reflectometry," *IEEE Photonics Technology Letters*, vol. 4, pp. 1404-1406, Dec. 1992.
Swanson, E. A. et al., "High-Speed Optical Coherence Domain Reflectometry," *Optics Letters*, vol. 17, pp. 151-153, Jan. 1992.
Takada, K. et al., "High-Resolution OFDR with Incorporated Fiberoptic Frequency Encoder," *IEEE Photonics Technology Letters*, vol. 4, pp. 1069-1072, Sep. 1992.
Takada, Kazumasa et al., "Narrow-Band light Source with Acoustooptic Tunable Filter for Optical Low-Coherence Reflectometry," *IEEE Photonics Technology Letters*, vol. 8, pp. 658-660, May 1996.
Takada, Kazumasa et al., "New Measurement System for Fault Location in Optical Wave-Guide Devices Based on an Interometric-Technique," *Applied Optics*, vol. 26, pp. 1603-1606, May 1987.
Tateda, Mitsuhiro et al., "Interferometric Method for Chromatic Dispersion Measurement in a Single-Mode Optical Fiber," *IEEE Journal Of Quantum Electronics*, vol. 17, pp. 404-407, Mar. 1981.
Toide, M. et al., "Two-Dimensional Coherent Detection Imaging in Multiple Scattering Media Based the Directional Resolution Capability of the Optical Heterodyne Method," *Applied Physics B(Photophysics and Laser Chemistry)*, vol. B52, pp. 391-394, 1991.
Trutna, W. R. et al., "Continuously Tuned External-Cavity Semiconductor-Laser," *Journal of Lightwave Technology*, vol. 11, pp. 1279-1286, Aug. 1993.

Uttam, Deepak et al., "Precision Time Domain Reflectometry in Optical Fiber Systems Using a Frequency Modulated Continuous Wave Ranging Technique," *Journal of Lightwave Technology*, vol. 3, pp. 971-977, Oct. 1985.

Von Der Weid, J. P. et al., "On the Characterization of Optical Fiber Network Components with Optical Frequency Domain Reflectometry," *Journal of Lightwave Technology*, vol. 15, pp. 1131-1141, Jul. 1997.

Wysocki, P.F. et al., "Broad-Spectrum, Wavelength-Swept, Erbium-Doped Fiber Laser at 1.55-Mu-M," *Optics Letters*, vol. 15, pp. 879-881, Aug. 1990.

Youngquist, Robert C. et al., "Optical Coherence-Domain Reflectometry—A New Optical Evaluation Technique," *Optics Letters*, vol. 12, pp. 158-160, Mar. 1987.

Yun, S. H. et al., "Wavelength-Swept Fiber Laser with Frequency Shifted Feedback and Resonantly Swept Intra-Cavity Acoustooptic Tunable Filter," *IEEE Journal of Selected Topics in Quantum Electronics*, vol. 3, pp. 1087-1096, Aug. 1997.

Yun, S. H. et al., "Interrogation of Fiber Grating Sensor Arrays with a Wavelength-Swept Fiber Laser," *Optics Letters*, vol. 23, pp. 843-845, Jun. 1998.

Yung, K. M., "Phase-Domain Processing of Optical Coherence Tomography Images," *Journal of Biomedical Optics*, vol. 4, pp. 125-136, Jan. 1999.

Zhou, Xiao-Qun et al., "Extended-Range FMCW Reflectometry Using an optical Loop with a Frequency Shifter," *IEEE Photonics Technology Letters*, vol. 8, pp. 248-250, Feb. 1996.

Zorabedian, Paul et al., "Tuning Fidelity of Acoustooptically Controlled External Cavity Semiconductor-Lasers," *Journal of Lightwave Technology*, vol. 13, pp. 62-66, Jan. 1995.

Victor S. Y. Lin et al., "A Porous Silicon-Based Optical Interferometric Biosensor," *Science Magazine*, vol. 278, pp. 840-843, Oct. 31, 1997.

De Boer, Johannes F. et al., "Review of Polarization Sensitive Optical Coherence Tomography and Stokes Vector Determination," *Journal of Biomedical Optics*, vol. 7, No. 3, Jul. 2002, pp. 359-371.

Jiao, Shuliang et al., "Depth-Resolved Two-Dimensional Stokes Vectors of Backscattered Light and Mueller Matrices of Biological Tissue Measured with Optical Coherence Tomography," *Applied Optics*, vol. 39, No. 34, Dec. 1, 2000, pp. 6318-6324.

Park, B. Hyle et al., "In Vivo Burn Depth Determination by High-Speed Fiber-Based Polarization Sensitive Optical Coherence Tomography," *Journal of Biomedical Optics*, vol. 6 No. 4, Oct. 2001, pp. 474-479.

Roth, Jonathan E. et al., "Simplified Method for Polarization-Sensitive Optical Coherence Tomography," *Optics Letters*, vol. 26, No. 14, Jul. 15, 2001, pp. 1069-1071.

Hitzenberger, Christoph K. et al., "Measurement and Imaging of Birefringence and Optic Axis Orientation by Phase Resolved Polarization Sensitive Optical Coherence Tomography," *Optics Express*, vol. 9, No. 13, Dec. 17, 2001, pp. 780-790.

Wang, Xueding et al., "Propagation of Polarized Light in Birefringent Turbid Media: Time-Resolved Simulations," Optical Imaging Laboratory, Biomedical Engineering Program, Texas A&M University.

Wong, Brian J.F. et al., "Optical Coherence Tomography of the Rat Cochlea," Journal of *Biomedical Optics*, vol. 5, No. 4, Oct. 2000, pp. 367-370.

Yao, Gang et al., "Propagation of Polarized Light in Turbid Media: Simulated Animation Sequences," *Optics Express*, vol. 7, No. 5, Aug. 28, 2000, pp. 198-203.

Wang, Xiao-Jun et al., "Characterization of Dentin and Enamel by Use of Optical Coherence Tomography," *Applied Optics*, vol. 38, No. 10, Apr. 1, 1999, pp. 2092-2096.

De Boer, Johannes F. et al., "Determination of the Depth-Resolved Stokes Parameters of Light Backscattered from Turbid Media by use of Polarization-Sensitive Optical Coherence Tomography," *Optics Letters*, vol. 24, No. 5, Mar. 1, 1999, pp. 300-302.

Ducros, Mathieu G. et al., "Polarization Sensitive Optical Coherence Tomography of the Rabbit Eye," *IEEE Journal of Selected Topics in Quantum Electronics*, vol. 5, No. 4, Jul./Aug. 1999, pp. 1159-1167.

Groner, Warren et al., "Orthogonal Polarization Spectral Imaging: A New Method for Study of the Microcirculation," *Nature Medicine Inc.*, vol. 5 No. 10, Oct. 1999, pp. 1209-1213.

De Boer, Johannes F. et al., "Polarization Effects in Optical Coherence Tomography of Various Viological Tissues," *IEEE Journal of Selected Topics in Quantum Electronics*, vol. 5, No. 4, Jul./Aug. 1999, pp. 1200-1204.

Yao, Gang et al., "Two-Dimensional Depth-Resolved Mueller Matrix Characterization of Biological Tissue by Optical Coherence Tomography," *Optics Letters*, Apr. 15, 1999, vol. 24, No. 8, pp. 537-539.

Lu, Shih-Yau et al., "Homogeneous and Inhomogeneous Jones Matrices," *J. Opt. Soc. Am. A.*, vol. 11, No. 2, Feb. 1994, pp. 766-773.

Bickel, S. William et al., "Stokes Vectors, Mueller Matrices, and Polarized Scattered Light," *Am. J. Phys.*, vol. 53, No. 5, May 1985 pp. 468-478.

Bréhonnet, F. Le Roy et al., "Optical Media and Target Characterization by Mueller Matrix Decomposition," *J. Phys. D: Appl. Phys.* 29, 1996, pp. 34-38.

Cameron, Brent D. et al., "Measurement and Calculation of the Two-Dimensional Backscattering Mueller Matrix of a Turbid Medium," *Optics Letters*, vol. 23, No. 7, Apr. 1, 1998, pp. 485-487.

De Boer, Johannes F. et al., "Two-Dimensional Birefringence Imaging in Biological Tissue by Polarization-Sensitive Optical Coherence Tomography," *Optics Letters*, vol. 22, No. 12, Jun. 15, 1997, pp. 934-936.

De Boer, Johannes F. et al., "Imaging Thermally Damaged Tissue by Polarization Sensitive Optical Coherence Tomography," *Optics Express*, vol. 3, No. 6, Sep. 14, 1998, pp. 212-218.

Everett, M.J. et al., "Birefringence Characterization of Biological Tissue by Use of Optical Coherence Tomography," *Optics Letters*, vol. 23, No. 3, Feb. 1, 1998, pp. 228-230.

Hee, Michael R. et al., "Polarization-Sensitive Low-Coherence Reflectometer for Birefringence Characterization and Ranging," *J. Opt. Soc. Am. B.*, vol. 9, No. 6, Jun. 1992, pp. 903-908.

Barakat, Richard, "Statistics of the Stokes Parameters," *J. Opt. Soc. Am. B.*, vol. 4, No. 7, Jul. 1987, pp. 1256-1263.

Schmitt, J.M. et al., "Cross-Polarized Backscatter in Optical Coherence Tomography of Biological Tissue," *Optics Letters*, vol. 23, No. 13, Jul. 1, 1998, pp. 1060-1062.

Schoenenberger, Klaus et al., "Mapping of Birefringence and Thermal Damage in Tissue by use of Polarization-Sensitive Optical Coherence Tomography," *Applied Optics*, vol. 37, No. 25, Sep. 1, 1998, pp. 6026-6036.

Pierce, Mark C. et al., "Simultaneous Intensity, Birefringence, and Flow Measurements with High-Speed Fiber-Based Optical Coherence Tomography," *Optics Letters*, vol. 27, No. 17, Sep. 1, 2002, pp. 1534-1536.

De Boer, Johannes F. et al., "Review of Polarization Sensitive Optical Coherence Tomography and Stokes Vector Determination," *Journal of Biomedical Optics*, Jul. 2002, vol. 7, No. 3, pp. 359-371.

Fried, Daniel et al., "Imaging Caries Lesions and Lesion Progression with Polarization Sensitive Optical Coherence Tomography," *Journal of Biomedical Optics*, vol. 7, No. 4, Oct. 2002, pp. 618-627.

Jiao, Shuliang et al., "Two-Dimensional Depth-Resolved Mueller Matrix of Biological Tissue Measured with Double-Beam Polarization-Sensitive Optical Coherence Tomography," *Optics Letters*, vol. 27, No. 2, Jan. 15, 2002, pp. 101-103.

Jiao, Shuliang et al., "Jones-Matrix Imaging of Biological Tissues with Quadruple-Channel Optical Coherence Tomography," *Journal of Biomedical Optics*, vol. 7, No. 3, Jul. 2002, pp. 350-358.

Kuranov, R.V. et al., "Complementary Use of Cross-Polarization and Standard OCT for Differential Diagnosis of Pathological Tissues," *Optics Express*, vol. 10, No. 15, Jul. 29, 2002, pp. 707-713.

Cense, Barry et al., "*In Vivo* Depth-Resolved Birefringence Measurements of the Human Retinal Nerve Fiber Layer by Polarization-Sensitive Optical Coherence Tomography," *Optics Letters*, vol. 27, No. 18, Sep. 15, 2002, pp. 1610-1612.

Ren, Hongwu et al., "Phase-Resolved Functional Optical Coherence Tomography: Simultaneous Imaging of *In Situ* Tissue Structure, Blood Flow Velocity, Standard Deviation, Birefringence, and Stokes Vectors in Human Skin," *Optics Letters*, vol. 27, No. 19, Oct. 1, 2002, pp. 1702-1704.

Tripathi, Renu et al., "Spectral Shaping for Non-Gaussian Source Spectra in Optical Coherence Tomography," *Optics Letters*, vol. 27, No. 6, Mar. 15, 2002, pp. 406-408.

Yasuno, Y. et al., "Birefringence Imaging of Human Skin by Polarization-Sensitive Spectral Interferometric Optical Coherence Tomography," *Optics Letters*, vol. 27, No. 20, Oct. 15, 2002 pp. 1803-1805.

White, Brian R. et al., "In Vivo Dynamic Human Retinal Blood Flow Imaging Using Ultra-High-Speed Spectral Domain Optical Doppler Tomography," *Optics Express*, vol. 11, No. 25, Dec. 15, 2003, pp. 3490-3497.

De Boer, Johannes F. et al., "Improved Signal-to-Noise Ratio in Spectral-Domain Compared with Time-Domain Optical Coherence Tomography," *Optics Letters*, vol. 28, No. 21, Nov. 1, 2003, pp. 2067-2069.

Jiao, Shuliang et al., "Optical-Fiber-Based Mueller Optical Coherence Tomography," *Optics Letters*, vol. 28, No. 14, Jul. 15, 2003, pp. 1206-1208.

Jiao, Shuliang et al., "Contrast Mechanisms in Polarization-Sensitive Mueller-Matrix Optical Coherence Tomography and Application in Burn Imaging," *Applied Optics*, vol. 42, No. 25, Sep. 1, 2003, pp. 5191-5197.

Moreau, Julien et al., "Full-Field Birefringence Imaging by Thermal-Light Polarization-Sensitive Optical Coherence Tomography. I. Theory," *Applied Optics*, vol. 42, No. 19, Jul. 1, 2003, pp. 3800-3810.

Moreau, Julien et al., "Full-Field Birefringence Imaging by Thermal-Light Polarization-Sensitive Optical Coherence Tomography. II. Instrument and Results," *Applied Optics*, vol. 42, No. 19, Jul. 1, 2003, pp. 3811-3818.

Morgan, Stephen P. et al., "Surface-Reflection Elimination in Polarization Imaging of Superficial Tissue," *Optics Letters*, vol. 28, No. 2, Jan. 15, 2003, pp. 114-116.

Oh, Jung-Taek et al., "Polarization-Sensitive Optical Coherence Tomography for Photoelasticity Testing of Glass/Epoxy Composites," *Optics Express*, vol. 11, No. 14, Jul. 14, 2003, pp. 1669-1676.

Park, B. Hyle et al., "Real-Time Multi-Functional Optical Coherence Tomography," *Optics Express*, vol. 11, No. 7, Apr. 7, 2003, pp. 782-793.

Shribak, Michael et al., "Techniques for Fast and Sensitive Measurements of Two-Dimensional Birefringence Distributions," *Applied Optics*, vol. 42, No. 16, Jun. 1, 2003, pp. 3009-3017.

Somervell, A.R.D. et al., "Direct Measurement of Fringe Amplitude and Phase Using a Heterodyne Interferometer Operating in Broadband Light," *Elsevier, Optics Communications*, Oct. 2003.

Stifter, D. et al., "Polarisation-Sensitive Optical Coherence Tomography for Material Characterisation and Strain-Field Mapping," Applied Physics A 76, Materials Science & Processing, Jan. 2003, pp. 947-951.

Davé, Digant P. et al., "Polarization-Maintaining Fiber-Based Optical Low-Coherence Reflectometer for Characterization and Ranging of Birefringence," *Optics Letters*, vol. 28, No. 19, Oct. 1, 2003, pp. 1775-1777.

Yang, Ying et al., "Observations of Birefringence in Tissues from Optic-Fibre-Based Optical Coherence Tomography," *Measurement Science and Technology*, Nov. 2002, pp. 41-46.

Yun, S.H. et al., "High-Speed Optical Frequency-Domain Imaging," *Optics Express*, vol. 11, No. 22, Nov. 3, 2003, pp. 2953-2963.

Yun, S.H. et al., "High-Speed Spectral-Domain Optical Coherence Tomography at 1.3 μm Wavelength," *Optics Express*, vol. 11, No. 26, Dec. 29, 2003, pp. 3598-3604.

Zhang, Jun et al., "Determination of Birefringence and Absolute Optic Axis Orientation Using Polarization-Sensitive Optical Coherence Tomography with PM Fibers," *Optics Express*, vol. 11, No. 24, Dec. 1, 2003, pp. 3262-3270.

Pircher, Michael et al., "Three Dimensional Polarization Sensitive OCT of Human Skin In Vivo," 2004, *Optical Society of America*.

Götzinger, Erich et al., "Measurement and Imaging of Birefringent Properties of the Human Cornea with Phase-Resolved, Polarization-Sensitive Optical Coherence Tomography," *Journal of Biomedical Optics*, vol. 9, No. 1, Jan./Feb. 2004, pp. 94-102.

Guo, Shuguang et al., "Depth-Resolved Birefringence and Differential Optical Axis Orientation Measurements with Finer-based Polarization-Sensitive Optical Coherence Tomography," *Optics Letters*, vol. 29, No. 17, Sep. 1, 2004, pp. 2025-2027.

Huang, Xiang-Run et al.,"Variation of Peripapillary Retinal Nerve Fiber Layer Birefringence in normal Human Subjects," *Investigative Ophthalmology & Visual Science*, vol. 45, No. 9, Sep. 2004, pp. 3073-3080.

Matcher, Stephen J. et al., "The Collagen Structure of Bovine Intervertebral Disc Studied Using Polarization-Sensitive Optical Coherence Tomography," *Physics in Medicine and Biology*, 2004, pp. 1295-1306.

Nassif, Nader et al., "*In Vivo* Human Retinal Imaging by Ultrahigh-Speed Spectral Domain Optical Coherence Tomography," *Optics Letters*, vol. 29, No. 5, Mar. 1, 2004, pp. 480-482.

Nassif, N.A. et al., "*In Vivo* High-Resolution Video-Rate Spectral-Domain Optical Coherence Tomography of the Human Retina and Optic Nerve," *Optics Express*, vol. 12, No. 3, Feb. 9, 2004, pp. 367-376.

Park, B. Hyle et al., "Comment on Optical-Fiber-Based Mueller Optical Coherence Tomography," *Optics Letters*, vol. 29, No. 24, Dec. 15, 2004, pp. 2873-2874.

Park, B. Hyle et al., "Jones Matrix Analysis for a Polarization-Sensitive Optical Coherence Tomography System Using Fiber-Optic Components," *Optics Letters*, vol. 29, No. 21, Nov. 1, 2004, pp. 2512-2514.

Pierce, Mark C. et al., "Collagen Denaturation can be Quantified in Burned Human Skin Using Polarization-Sensitive Optical Coherence Tomography," *Elsevier, Burns*, 2004, pp. 511-517.

Pierce, Mark C. et al., "Advances in Optical Coherence Tomography Imaging for Dermatology," *The Society for Investigative Dermatology, Inc.* 2004, pp. 458-463.

Pierce, Mark C. et al., "Birefringence Measurements in Human Skin Using Polarization-Sensitive Optical Coherence Tomography," *Journal of Biomedical Optics*, vol. 9, No. 2, Mar./Apr. 2004, pp. 287-291.

Cense, Barry et al., "*In Vivo* Birefringence and Thickness Measurements of the Human Retinal Nerve Fiber Layer Using Polarization-Sensitive Optical Coherence Tomography," *Journal of Biomedical Optics*, vol. 9, No. 1, Jan./Feb. 2004, pp. 121-125.

Pircher, Michael et al., "Imaging Of Polarization Properties of Human Retina *in Vivo* with Phase Resolved Transversal PS-OCT," *Optics Express*, vol. 12, No. 24, Nov. 29, 2004 pp. 5940-5951.

Pircher, Michael et al., "Transversal Phase Resolved Polarization Sensitive Optical Coherence Tomography," *Physics in Medicine & Biology*, 2004, pp. 1257-1263.

Srinivas, Shyam M. et al., "Determination of Burn Depth by Polarization-Sensitive Optical Coherence Tomography," *Journal of Biomedical Optics*, vol. 9, No. 1, Jan./Feb. 2004, pp. 207-212.

Strasswimmer, John et al., "Polarization-Sensitive Optical Coherence Tomography of Invasive Basal Cell Carcinoma," *Journal of Biomedical Optics*, vol. 9, No. 2, Mar./Apr. 2004, pp. 292-298.

Todorovič, Miloš et al., "Determination of Local Polarization Properties of Biological Samples in the Presence of Diattenuation by use of Mueller Optical Coherence Tomography," *Optics Letters*, vol. 29, No. 20, Oct. 15, 2004, pp. 2402-2404.

Yasuno, Yoshiaki et al., "Polarization-Sensitive Complex Fourier Domain Optical Coherence Tomography for Jones Matrix Imaging of Biological Samples," Applied Physics Letters, vol. 85, No. 15, Oct. 11, 2004, pp. 3023-3025.

Acioli, L. H., M. Ulman, et al. (1991). "Femtosecond Temporal Encoding in Barium-Titanate." *Optics Letters* 16(24): 1984-1986.

Aigouy, L., A. Lahrech, et al. (1999). "Polarization effects in apertureless scanning near-field optical microscopy: an experimental study." *Optics Letters* 24(4): 187-189.

Akiba, M., K. P. Chan, et al. (2003). "Full-field optical coherence tomography by two-dimensional heterodyne detection with a pair of CCD cameras." *Optics Letters* 28(10): 816-818.

Akkin, T., D. P. Dave, et al. (2004). "Detection of neural activity using phase-sensitive optical low-coherence reflectometry." *Optics Express* 12(11): 2377-2386.

Akkin, T., D. P. Dave, et al. (2003). "Surface analysis using phase sensitive optical low coherence reflectometry." *Lasers in Surgery and Medicine*: 4-4.

Akkin, T., D. P. Dave, et al. (2003). "Imaging tissue response to electrical and photothermal stimulation with nanometer sensitivity." *Lasers in Surgery and Medicine* 33(4): 219-225.

Akkin, T., T. E. Milner, et al. (2002). "Phase-sensitive measurement of birefringence change as an indication of neural functionality and diseases." *Lasers in Surgery and Medicine*: 6-6.

Andretzky, P., Lindner, M.W., Herrmann, J.M., Schultz, A., Konzog, M., Kiesewetter, F., Haeusler, G. (1999). "Optical coherence tomography by 'spectral radar': Dynamic range estimation and in vivo measurements of skin." *Proceedings of SPIE—The International Society for Optical Engineering* 3567: pp. 78-87.

Antcliff, R. J., T. J. ffytche, et al. (2000). "Optical coherence tomography of melanocytoma." *American Journal of Ophthalmology* 130(6): 845-7.

Antcliff, R. J., M. R. Stanford, et al. (2000). "Comparison between optical coherence tomography and fundus fluorescein angiography for the detection of cystoid macular edema in patients with uveitis." *Ophthalmology* 107(3): 593-9.

Anvari, B., T. E. Milner, et al. (1995). "Selective Cooling of Biological Tissues—Application for Thermally Mediated Therapeutic Procedures." *Physics in Medicine and Biology* 40(2): 241-252.

Anvari, B., B. S. Tanenbaum, et al. (1995). "A Theoretical-Study of the Thermal Response of Skin to Cryogen Spray Cooling and Pulsed-Laser Irradiation—Implications for Treatment of Port-Wine Stain Birthmarks." *Physics in Medicine and Biology* 40(9): 1451-1465.

Arend, O., M. Ruffer, et al. (2000). "Macular circulation in patients with diabetes mellitus with and without arterial hypertension." *British Journal of Ophthalmology* 84(12): 1392-1396.

Arimoto, H. and Y. Ohtsuka (1997). "Measurements of the complex degree of spectral coherence by use of a wave-front-folded interferometer." *Optics Letters* 22(13): 958-960.

Azzolini, C., F. Patelli, et al. (2001). "Correlation between optical coherence tomography data and biomicroscopic interpretation of idiopathic macular hole." *American Journal of Ophthalmology* 132(3): 348-55.

Baba, T., K. Ohno-Matsui, et al. (2002). "Optical coherence tomography of choroidal neovascularization in high myopia." *Acta Ophthalmologica Scandinavica* 80(1): 82-7.

Bail, M. A. H., Gerd; Herrmann, Juergen M.; Lindner, Michael W.; Ringler, R. (1996). "Optical coherence tomography with the "spectral radar": fast optical analysis in volume scatterers by short-coherence interferometry." *Proc. SPIE*, 2925: p. 298-303.

Baney, D. M. and W. V. Sorin (1993). "Extended-Range Optical Low-Coherence Reflectometry Using a Recirculating Delay Technique." *Ieee Photonics Technology Letters* 5(9): 1109-1112.

Baney, D. M., B. Szafraniec, et al. (2002). "Coherent optical spectrum analyzer." *Ieee Photonics Technology Letters* 14(3): 355-357.

Barakat, R. (1981). "Bilinear Constraints between Elements of the 4by4 Mueller-Jones Transfer-Matrix of Polarization Theory." *Optics Communications* 38(3): 159-161.

Barakat, R. (1993). "Analytic Proofs of the Arago-Fresnel Laws for the Interference of Polarized-Light." *Journal of the Optical Society of America a-Optics Image Science and Vision* 10(1): 180-185.

Barbastathis, G. and D. J. Brady (1999). "Multidimensional tomographic imaging using volume holography." *Proceedings of the Ieee* 87(12): 2098-2120.

Bardal, S., A. Kamal, et al. (1992). "Photoinduced Birefringence in Optical Fibers—a Comparative-Study of Low-Birefringence and High-Birefringence Fibers." *Optics Letters* 17(6): 411-413.

Barsky, S. H., S. Rosen, et al. (1980). "Nature and Evolution of Port Wine Stains—Computer-Assisted Study." *Journal of Investigative Dermatology* 74(3): 154-157.

Barton, J. K., J. A. Izatt, et al. (1999). "Three-dimensional reconstruction of blood vessels from in vivo color Doppler optical coherence tomography images." *Dermatology* 198(4): 355-361.

Barton, J. K., A. Rollins, et al. (2001). "Photothermal coagulation of blood vessels: a comparison of high-speed optical coherence tomography and numerical modelling." *Physics in Medicine and Biology* 46.

Barton, J. K., A. J. Welch, et al. (1998). "Investigating pulsed dye laser-blood vessel interaction with color Doppler optical coherence tomography." *Optics Express* 3.

Bashkansky, M., M. D. Duncan, et al. (1997). "Subsurface defect detection in ceramics by high-speed high-resolution optical coherent tomography." *Optics Letters* 22 (1): 61-63.

Bashkansky, M. and J. Reintjes (2000). "Statistics and reduction of speckle in optical coherence tomography." *Optics Letters* 25(8): 545-547.

Baumgartner, A., S. Dichtl, et al. (2000). "Polarization-sensitive optical coherence tomography of dental structures." *Caries Research* 34(1): 59-69.

Baumgartner, A., C. K. Hitzenberger, et al. (2000). "Resolution-improved dual-beam and standard optical coherence tomography: a comparison." *Graefes Archive for Clinical and Experimental Ophthalmology* 238(5): 385-392.

Baumgartner, A., C. K. Hitzenberger, et al. (1998). "Signal and resolution enhancements in dual beam optical coherence tomography of the human eye." *Journal of Biomedical Optics* 3(1): 45-54.

Beaurepaire, E., P. Gleyzes, et al. (1998). *Optical coherence microscopy for the in-depth study of biological structures: System based on a parallel detection scheme*, Proceedings of SPIE—The International Society for Optical Engineering.

Beaurepaire, E., L. Moreaux, et al. (1999). "Combined scanning optical coherence and two-photon-excited fluorescence microscopy." *Optics Letters* 24(14): 969-971.

Bechara, F. G., T. Gambichler, et al. (2004). "Histomorphologic correlation with routine histology and optical coherence tomography." *Skin Research and Technology* 10 (3): 169-173.

Bechmann, M., M. J. Thiel, et al. (2000). "Central corneal thickness determined with optical coherence tomography in various types of glaucoma. [see comments]." *British Journal of Ophthalmology* 84(11): 1233-7.

Bek, T. and M. Kandi (2000). "Quantitative anomaloscopy and optical coherence tomography scanning in central serous chorioretinopathy." *Acta Ophthalmologica Scandinavica* 78(6): 632-7.

Benoit, A. M., K. Naoun, et al. (2001). "Linear dichroism of the retinal nerve fiber layer expressed with Mueller matrices." *Applied Optics* 40(4): 565-569.

Bicout, D., C. Brosseau, et al. (1994). "Depolarization of Multiply Scattered Waves by Spherical Diffusers—Influence of the Size Parameter." *Physical Review* E 49(2): 1767-1770.

Blanchot, L., M. Lebec, et al. (1997). *Low-coherence in depth microscopy for biological tissues imaging: Design of a real time control system*. Proceedings of SPIE—the International Society for Optical Engineering.

Blumenthal, E. Z. and R. N. Weinreb (2001). "Assessment of the retinal nerve fiber layer in clinical trials of glaucoma neuroprotection. [Review] [36 refs]." *Survey of Ophthalmology* 45(Suppl 3): S305-12; discussion S332-4.

Blumenthal, E. Z., J. M. Williams, et al. (2000). "Reproducibility of nerve fiber layer thickness measurements by use of optical coherence tomography." *Ophthalmology* 107(12): 2278-82.

Boppart, S. A., B. E. Bouma, et al. (1996). "Imaging developing neural morphology using optical coherence tomography." *Journal of Neuroscience Methods* 70.

Boppart, S. A., B. E. Bouma, et al. (1997). "Forward-imaging instruments for optical coherence tomography." *Optics Letters* 22.

Boppart, S. A., B. E. Bouma, et al. (1998). "Intraoperative assessment of microsurgery with three-dimensional optical coherence tomography." *Radiology* 208: 81-86.

Boppart, S. A., J. Herrmann, et al. (1999). "High-resolution optical coherence tomography-guided laser ablation of surgical tissue." *Journal of Surgical Research* 82(2): 275-84.

Bouma, B. E. and J. G. Fujimoto (1996). "Compact Kerr-lens mode-locked resonators." *Optics Letters* 21.

Bouma, B. E., L. E. Nelson, et al. (1998). "Optical coherence tomographic imaging of human tissue at 1.55 mu m and 1.81 mu m using Er and Tm-doped fiber sources." *Journal of Biomedical Optics* 3.

Bouma, B. E., M. Ramaswamy-Paye, et al. (1997). "Compact resonator designs for mode-locked solid-state lasers." *Applied Physics B(Lasers and Optics)* B65.

Bouma, B. E. and G. J. Tearney (2002). "Clinical imaging with optical coherence tomography." *Academic Radiology* 9(8): 942-953.

Bouma, B. E., G. J. Tearney, et al. (1996). "Self-phase-modulated Kerr-lens mode-locked Cr:forsterite laser source for optical coherence tomography." *Optics Letters* 21(22): 1839.

Bouma, B. E., G. J. Tearney, et al. (2000). "High-resolution imaging of the human esophagus and stomach in vivo using optical coherence tomography." *Gastrointestinal Endoscopy* 51(4): 467-474.

Bouma, B. E., G. J. Tearney, et al. (2003). "Evaluation of intracoronary stenting by intravascular optical coherence tomography." *Heart* 89(3): 317-320.

Bourquin, S., V. Monterosso, et al. (2000). "Video-rate optical low-coherence reflectometry based on a linear smart detector array." *Optics Letters* 25(2): 102-104.

Bourquin, S., P. Seitz, et al. (2001). "Optical coherence topography based on a two-dimensional smart detector array." *Optics Letters* 26(8): 512-514.

Bouzid, A., M. A. G. Abushagur, et al. (1995). "Fiber-optic four-detector polarimeter." *Optics Communications* 118(3-4): 329-334.

Bowd, C., R. N. Weinreb, et al. (2000). "The retinal nerve fiber layer thickness in ocular hypertensive, normal, and glaucomatous eyes with optical coherence tomography." *Archives of Ophthalmology* 118(1): 22-6.

Bowd, C., L. M. Zangwill, et al. (2001). "Detecting early glaucoma by assessment of retinal nerve fiber layer thickness and visual function." *Investigative Ophthalmology & Visual Science* 42(9): 1993-2003.

Bowd, C., L. M. Zangwill, et al. (2002). "Imaging of the optic disc and retinal nerve fiber layer: the effects of age, optic disc area, refractive errror, and gender." *Journal of the Optical Society of America, A, Optics, Image Science & Vision* 19(1): 197-207.

Brand, S., J. M. Poneros, et al. (2000). "Optical coherence tomography in the gastrointestinal tract." *Endoscopy* 32(10): 796-803.

Brezinski, M. E. and J. G. Fujimoto (1999). "Optical coherence tomography: high-resolution imaging in nontransparent tissue." *IEEE Journal of Selected Topics in Quantum Electronics* 5(4): 1185-1192.

Brezinski, M. E., G. J. Tearney, et al. (1996). "Imaging of coronary artery microstructure (in vitro) with optical coherence tomography." *American Journal of Cardiology* 77(1): 92-93.

Brezinski, M. E., G. J. Tearney, et al. (1996). "Optical coherence tomography for optical biopsy—Properties and demonstration of vascular pathology." *Circulation* 93(6): 1206-1213.

Brezinski, M. E., G. J. Tearney, et al. (1997). "Assessing atherosclerotic plaque morphology: Comparison of optical coherence tomography and high frequency intravascular ultrasound." *Heart* 77(5): 397-403.

Brink, H. B. K. and G. J. Vanblokland (1988). "Birefringence of the Human Foveal Area Assessed Invivo with Mueller-Matrix Ellipsometry." *Journal of the Optical Society of America a-Optics Image Science and Vision* 5(1): 49-57.

Brosseau, C. and D. Bicout (1994). "Entropy Production in Multiple-Scattering of Light by a Spatially Random Medium." *Physical Review E* 50(6): 4997-5005.

Burgoyne, C. F., D. E. Mercante, et al. (2002). "Change detection in regional and volumetric disc parameters using longitudinal confocal scanning laser tomography." *Ophthalmology* 109(3): 455-66.

Candido, R. and T. J. Allen (2002). "Haemodynamics in microvascular complications in type 1 diabetes." *Diabetes-Metabolism Research and Reviews* 18(4): 286-304.

Cense, B., T. C. Chen, et al. (2004). "Thickness and birefringence of healthy retinal nerve fiber layer tissue measured with polarization-sensitive optical coherence tomography." *Investigative Ophthalmology & Visual Science* 45(8): 2606-2612.

Cense, B., N. Nassif, et al. (2004). "Ultrahigh-Resolution High-Speed Retinal Imaging Using Spectral-Domain Optical Coherence Tomography." *Optics Express* 12(11): 2435-2447.

Chance, B., J. S. Leigh, et al. (1988). "Comparison of Time-Resolved and Time-Unresolved Measurements of Deoxyhemoglobin in Brain." *Proceedings of the National Academy of Sciences of the United States of America* 85(14): 4971-4975.

Chang, E. P., D. A. Keedy, et al. (1974). "Ultrastructures of Rabbit Corneal Stroma—Mapping of Optical and Morphological Anisotropies." *Biochimica Et Biophysica Acta* 343(3): 615-626.

Chartier, T., A. Hideur, et al. (2001). "Measurement of the elliptical birefringence of single-mode optical fibers." *Applied Optics* 40(30): 5343-5353.

Chauhan, B. C., J. W. Blanchard, et al. (2000). "Technique for Detecting Serial Topographic Changes in the Optic Disc and Peripapillary Retina Using Scanning Laser Tomograph." *Invest Ophthalmol Vis Sci* 41: 775-782.

Chen, Z. P., T. E. Milner, et al. (1997). "Optical Doppler tomographic imaging of fluid flow velocity in highly scattering media." *Optics Letters* 22(1): 64-66.

Chen, Z. P., T. E. Milner, et al. (1997). "Noninvasive imaging of in vivo blood flow velocity using optical Doppler tomography." *Optics Letters* 22(14): 1119-1121.

Chen, Z. P., Y. H. Zhao, et al. (1999). "Optical Doppler tomography." *Ieee Journal of Selected Topics in Quantum Electronics* 5(4): 1134-1142.

Cheong, W. F., S. A. Prahl, et al. (1990). "A Review of the Optical-Properties of Biological Tissues." *Ieee Journal of Quantum Electronics* 26(12): 2166-2185.

Chernikov, S. V., Y. Zhu, et al. (1997). "Supercontinuum self-Q-switched ytterbium fiber laser." *Optics Letters* 22(5): 298-300.

Cho, S. H., B. E. Bouma, et al. (1999). "Low-repetition-rate high-peak-power Kerr-lens mode-locked Ti:Al/sub 2/0/sub 3/ laser with a multiple-pass cavity." *Optics Letters* 24(6): 417-419.

Choma, M. A., M. V. Sarunic, et al. (2003). "Sensitivity advantage of swept source and Fourier domain optical coherence tomography." *Optics Express* 11(18): 2183-2189.

Choma, M. A., C. H. Yang, et al. (2003). "Instantaneous quadrature low-coherence interferometry with 3 x 3 fiber-optic couplers." *Optics Letters* 28(22): 2162-2164.

Choplin, N. T. and D. C. Lundy (2001). "The sensitivity and specificity of scanning laser polarimetry in the detection of glaucoma in a clinical setting." *Ophthalmology* 108 (5): 899-904.

Christens Barry, W. A., W. J. Green, et al. (1996). "Spatial mapping of polarized light transmission in the central rabbit cornea." *Experimental Eye Research* 62(6): 651-662.

Chvapil, M., D. P. Speer, et al. (1984). "Identification of the depth of burn injury by collagen stainability." *Plastic & Reconstructive Surgery* 73(3): 438-41.

Cioffi, G. A. (2001). "Three common assumptions about ocular blood flow and glaucoma." *Survey of Ophthalmology* 45: S325-S331.

Coleman, A. L. (1999). "Glaucoma." *Lancet* 354(9192): 1803-10.

Collaborative Normal-Tension Glaucoma Study Group (1998). "Comparison of Glaucomatous Progression Between Untreated Patients With Normal Tension Glaucoma and Patients with Therapeutically Reduced Intraocular Pressures." *Am J Ophthalmol* 126: 4887-97.

Collaborative Normal-Tension Glaucoma Study Group (1998). "The effectiveness of intraocular pressure reduction in the treatment of normal-tension glaucoma." *Am J Ophthalmol* 126: 498-505.

Collaborative Normal-Tension Glaucoma Study Group (2001). "Natural History of Normal-Tension Glaucoma." *Ophthalmology* 108: 247-253.

Colston, B. W., M. J. Everett, et al. (1998). "Imaging of hard- and soft-tissue structure in the oral cavity by optical coherence tomography." *Applied Optics* 37(16): 3582-3585.

Colston, B. W., U. S. Sathyam, et al. (1998). "Dental OCT." *Optics Express* 3(6): 230-238.

Congdon, N. G., D. S. Friedman, et al. (2003). "Important causes of visual impairment in the world today." *Jama-Journal of the American Medical Association* 290(15): 2057-2060.

Cregan, R. F., B. J. Mangan, et al. (1999). "Single-mode photonic band gap guidance of light in air." *Science* 285(5433): 1537-1539.

DalMolin, M., A. Galtarossa, et al. (1997). "Experimental investigation of linear polarization in high-birefringence single-mode fibers." *Applied Optics* 36(12): 2526-2528.

Danielson, B. L. and C. D. Whittenberg (1987). "Guided-Wave Reflectometry with Micrometer Resolution." *Applied Optics* 26(14): 2836-2842.

Dave, D. P. and T. E. Milner (2000). "Doppler-angle mesurement in highly scattering media." *Optics Letters* 25(20): 1523-1525.

de Boer, J. F., T. E. Milner, et al. (1998). *Two dimensional birefringence imaging in biological tissue using phase and polarization sensitive optical coherence tomography*. Trends in Optics and Photonics (TOPS): Advances in Optical Imaging and Photon Migration, Orlando, USA, Optical Society of America, Washington, DC 1998.

de Boer, J. F., C. E. Saxer, et al. (2001). "Stable carrier generation and phase-resolved digital data processing in optical coherence tomography." *Applied Optics* 40(31): 5787-5790.

Degroot, P. and L. Deck (1993). "3-Dimensional Imaging by Sub-Nyquist Sampling of White-Light Interferograms." *Optics Letters* 18(17): 1462-1464.

Denk, W., J. H. Strickler, et al. (1990). "2-Photon Laser Scanning Fluorescence Microscopy." *Science* 248(4951): 73-76.

Descour, M. R., A. H. O. Karkkainen, et al. (2002). "Toward the development of miniaturized Imaging systems for detection of pre-cancer." *Ieee Journal of Quantum Electronics* 38(2): 122-130.

Dettwiller, L. (1997). "Polarization state interference: A general investigation." *Pure and Applied Optics* 6(1): 41-53.

DiCarlo, C. D., W. P. Roach, et al. (1999). "Comparison of optical coherence tomography imaging of cataracts with histopathy." *Journal of Biomedical Optics* 4.

Ding, Z., Y. Zhao, et al. (2002). "Real-time phase-resolved optical coherence tomography and optical Doppler tomography." *Optics Express* 10(5): 236-245.

Dobrin, P. B. (1996). "Effect of histologic preparation on the cross-sectioned area of arterial rings." *Journal of Surgical Research* 61(2): 413-5.

Donohue, D. J., B. J. Stoyanov, et al. (1995). "Numerical Modeling of the Corneas Lamellar Structure and Birefringence Properties." *Journal of the Optical Society of America a-Optics Image Science and Vision* 12(7): 1425-1438.

Doornbos, R. M. P., R. Lang, et al. (1999). "The determination of in vivo human tissue optical properties and absolute chromophore concentrations using spatially resolved steady-state diffuse reflectance spectroscopy." *Physics in Medicine and Biology* 44(4): 967-981.

Drexler, W., A. Baumgartner, et al. (1997). "Biometric investigation of changes in the anterior eye segment during accommodation." *Vision Research* 37(19): 2789-2800.

Drexler, W., A. Baumgartner, et al. (1997). "Submicrometer precision biometry of the anterior segment of the human eye." *Investigative Ophthalmology & Visual Science* 38(7): 1304-1313.

Drexler, W., A. Baumgartner, et al. (1998). "Dual beam optical coherence tomography: signal identification for ophthalmologic diagnosis." *Journal of Biomedical Optics* 3 (1): 55-65.

Drexler, W., O. Findl, et al. (1998). "Partial coherence interferometry: A novel approach to biometry in cataract surgery." *American Journal of Ophthalmology* 126(4): 524-534.

Drexler, W., O. Findl, et al. (1997). "Clinical feasibility of dual beam optical coherence topography and tomography for ophthalmologic diagnosis." *Investigative Ophthalmology & Visual Science* 38(4): 1038-1038.

Drexler, W., C. K. Hitzenberger, et al. (1998). "Investigation of dispersion effects in ocular media by multiple wavelength partial coherence interferometry." *Experimental Eye Research* 66(1): 25-33.

Drexler, W., C. K. Hitzenberger, et al. (1996). "(Sub)micrometer precision biometry of the human eye by optical coherence tomography and topography." *Investigative Ophthalmology & Visual Science* 37(3): 4374-4374.

Drexler, W., C. K. Hitzenberger, et al. (1995). "Measurement of the Thickness of Fundus Layers by Partial Coherence Tomography." *Optical Engineering* 34(3): 701-710.

Drexler, W., U. Morgner, et al. (2001). "Ultrahigh-resolution ophthalmic optical coherence tomography." *Nature Medicine* 7(4): 502-507.

Drexler, W., U. Morgner, et al. (2001). "Ultrahigh-resolution ophthalmic optical coherence tomography. [erratum appears in Nat Med 2001 May;7(5):636]." *Nature Medicine* 7(4): 502-7.

Drexler, W., H. Sattmann, et al. (2003). "Enhanced visualization of macular pathology with the use of ultrahigh-resolution optical coherence tomography." *Archives of Ophthalmology* 121(5): 695-706.

Drexler, W., D. Stamper, et al. (2001). "Correlation of collagen organization with polarization sensitive imaging of in vitro cartilage: implications for osteoarthritis." *Journal of Rheumatology* 28(6): 1311-8.

Droog, E. J., W. Steenbergen, et al. (2001). "Measurement of depth of burns by laser Doppler perfusion imaging." *Burns* 27(6): 561-8.

Dubois, A., K. Grieve, et al. (2004). "Ultrahigh-resolution full-field optical coherence tomography." *Applied Optics* 43(14): 2874-2883.

Dubois, AL. Vabre, et al. (2002). "High-resolution full-field optical coherence tomography with a Linnik microscope." *Applied Optics* 41(4): 805-812.

Ducros, M., M. Laubscher, et al. (2002). "Parallel optical coherence tomography in scattering samples using a two-dimensional smart-pixel detector array." *Optics Commuications* 202(1-3): 29-35.

Ducros, M. G., J. D. Marsack, et al. (2001). "Primate retina imaging with polarization-sensitive optical coherence tomography." *Journal of the Optical Society of America a-Optics Image Science and Vision* 18(12): 2945-2956.

Duncan, A., J. H. Meek, et al. (1995). "Optical Pathlength Measurements on Adult Head, Calf and Forearm and the Head of the Newborn-Infant Using Phase-Resolved Optical Spectroscopy." *Physics in Medicine and Biology* 40(2): 295-304.

Eigensee, A., G. Haeusler, et al. (1996). "New method of short-coherence interferometry in human skin (in vivo) and in solid volume scatterers." *Proceedings of SPIE—The International Society for Optical Engineering* 2925: 169-178.

Eisenbeiss, W., J. Marotz, et al. (1999). "Reflection-optical multispectral imaging method for objective determination of burn depth." *Burns* 25(8): 697-704.

Elbaum, M., M. King, et al. (1972). "Wavelength-Diversity Technique for Reduction of Speckle Size." *Journal of the Optical Society of America* 62(5): 732-&.

Ervin, J. C., H. G. Lemij, et al. (2002). "Clinician change detection viewing longitudinal stereophotographs compared to confocal scanning laser tomography in the LSU Experimental Glaucoma (LEG) Study." *Ophthalmology* 109(3): 467-81.

Essenpreis, M., C. E. Elwell, et al. (1993). "Spectral Dependence of Temporal Point Spread Functions in Human Tissues." *Applied Optics* 32(4): 418-425.

Eun, H. C. (1995). "Evaluation of skin blood flow by laser Doppler flowmetry. [Review] [151 refs]." *Clinics in Dermatology* 13(4): 337-47.

Evans, J. A., J. M. Poneros, et al. (2004). "Application of a histopathologic scoring system to optical coherence tomography (OCT) images to identify high-grade dysplasia in Barrett's esophagus." *Gastroenterology* 126(4): A51-A51.

Feldchtein, F. I., G. V. Gelikonov, et al. (1998). "In vivo OCT imaging of hard and soft tissue of the oral cavity." *Optics Express* 3(6): 239-250.

Feldchtein, F. I., G. V. Gelikonov, et al. (1998). "Endoscopic applications of optical coherence tomography." *Optics Express* 3(6): 257-270.

Fercher, A. F., W. Drexler, et al. (1997). "Optical ocular tomography." *Neuro-Ophthalmology* 18(2): 39-49.

Fercher, A. F., W. Drexler, et al. (1994). *Measurement of optical distances by optical spectrum modulation*. Proceedings of SPIE—The International Society for Optical Engineering.

Fercher, A. F., W. Drexler, et al. (2003). "Optical coherence tomography—principles and applications." *Reports on Progress in Physics* 66(2): 239-303.

Fercher, A. F., C. Hitzenberger, et al. (1991). "Measurement of Intraocular Optical Distances Using Partially Coherent Laser-Light." *Journal of Modern Optics* 38(7): 1327-1333.

Fercher, A. F., C. K. Hitzenberger, et al. (1996). *Ocular coherence interferometry*. Proceedings of SPIE—The International Society for Optical Engineering.

Fercher, A. F., C. K. Hitzenberger, et al. (1993). "In-Vivo Optical Coherence Tomography." *American Journal of Ophthalmology* 116(1): 113-115.

Fercher, A. F., C. K. Hitzenberger, et al. (1994). *In-vivo dual-beam optical coherence tomography*. Proceedings of SPIE—The International Society for Optical Engineering.

Fercher, A. F., C. K. Hitzenberger, et al. (1995). "Measurement of Intraocular Distances by Backscattering Spectral Interferometry." *Optics Communications* 117(1-2): 43-48.

Fercher, A. F., C. K. Hitzenberger, et al. (2000). "A thermal light source technique for optical coherence tomography." *Optics Communications* 185(1-3): 57-64.

Fercher, A. F., C. K. Hitzenberger, et al. (2001). "Numerical dispersion compensation for Partial Coherence Interferometry and Optical Coherence Tomography." *Optics Express* 9(12): 610-615.

Fercher, A. F., C. K. Hitzenberger, et al. (2002). "Dispersion compensation for optical coherence tomography depth-scan signals by a numerical technique." *Optics Communications* 204(1-6): 67-74.

Fercher, A. F., H. C. Li, et al. (1993). "Slit Lamp Laser-Doppler Interferometer." *Lasers in Surgery and Medicine* 13(4): 447-452.

Fercher, A. F., K. Mengedoht, et al. (1988). "Eye-Length Measurement by Interferometry with Partially Coherent-Light." *Optics Letters* 13(3): 186-188.

Ferro, P., M. Haelterman, et al. (1991). "All-Optical Polarization Switch with Long Low-Birefringence Fiber." *Electronics Letters* 27(16): 1407-1408.

Fetterman, M. R., D. Goswami, et al. (1998). "Ultrafast pulse shaping: amplification and characterization." *Optics Express* 3(10): 366-375.

Findl, O., W. Drexler, et al. (2001). "Improved prediction of intraocular lens power using partial coherence interferometry." *Journal of Cataract and Refractive Surgery* 27 (6): 861-867.

Fork, R. L., C. H. B. Cruz, et al. (1987). "Compression of Optical Pulses to 6 Femtoseconds by Using Cubic Phase Compensation." *Optics Letters* 12(7): 483-485.

Foschini, G. J. and C. D. Poole (1991). "Statistical-Theory of Polarization Dispersion in Single-Mode Fibers." *Journal of Lightwave Technology* 9(11): 1439-1456.

Francia, C., F. Bruyere, et al. (1998). "PMD second-order effects on pulse propagation in single-mode optical fibers." *Ieee Photonics Technology Letters* 10(12): 1739-1741.

Fried, D., R. E. Glena, et al. (1995). "Nature of Light-Scattering in Dental Enamel and Dentin at Visible and near-Infrared Wavelengths." *Applied Optics* 34(7): 1278-1285.

Fujimoto, J. G., M. E. Brezinski, et al. (1995). "Optical Biopsy and Imaging Using Optical Coherence Tomography." *Nature Medicine* 1(9): 970-972.

Fukusawa, A. and H. Iijima (2002). "Optical coherence tomography of choroidal osteoma." *American Journal of Ophthalmology* 133(3): 419-21.

Fymat, A. L. (1981). "High-Resolution Interferometric Spectrophotopotarimetry." *Optical Engineering* 20(1): 25-30.

Galtarossa, A., L. Palmieri, et al. (2000). "Statistical characterization of fiber random birefringence." *Optics Letters* 25(18): 1322-1324.

Galtarossa, A., L. Palmieri, et al. (2000). "Measurements of beat length and perturbation length in long single-mode fibers." *Optics Letters* 25(6): 384-386.

Gandjbakhche, A. H., P. Mills, et al. (1994). "Light-Scattering Technique for the Study of Orientation and Deformation of Red-Blood-Cells in a Concentrated Suspension." *Applied Optics* 33(6): 1070-1078.

Garcia, N. and M. Nieto-Vesperinas (2002). "Left-handed materials do not make a perfect lens." *Physical Review Letters* 88(20).

Gelikonov, V. M., G. V. Gelikonov, et al. (1995). "Coherent Optical Tomography of Microscopic Inhomogeneities in Biological Tissues." *Jetp Letters* 61(2): 158-162.

George, N. and A. Jain (1973). "Speckle Reduction Using Multiple Tones of Illumination." *Applied Optics* 12(6): 1202-1212.

Gibson, G. N., R. Klank, et al. (1996). "Electro-optically cavity-dumped ultrashort-pulse Ti:sapphire oscillator." *Optics Letters* 21(14): 1055.

Gil, J. J. (2000). "Characteristic properties of Mueller matrices." *Journal of the Optical Society of America a-Optics Image Science and Vision* 17(2): 328-334.

Gil, J. J. and E. Bernabeu (1987). "Obtainment of the Polarizing and Retardation Parameters of a Nondepolarizing Optical-System from the Polar Decomposition of Its Mueller Matrix." *Optik* 76(2): 67-71.

Gladkova, N. D., G. A. Petrova, et al. (2000). "In vivo optical coherence tomography imaging of human skin: norm and pathology." *Skin Research and Technology* 6 (1): 6-16.

Glaessl, A., A. G. Schreyer, et al. (2001). "Laser surgical planning with magnetic resonance imaging-based 3-dimensional reconstructions for intralesional Nd : YAG laser therapy of a venous malformation of the neck." *Archives of Dermatology* 137(10): 1331-1335.

Gloesmann, M., B. Hermann, et al. (2003). "Histologic correlation of pig retina radial stratification with ultrahigh-resolution optical coherence tomography." *Investigative Ophthalmology & Visual Science* 44(4): 1696-1703.

Goldberg, L. and D. Mehuys (1994). "High-Power Superluminescent Diode Source." *Electronics Letters* 30(20): 1682-1684.

Goldsmith, J. A., Y. Li, et al. (2005). "Anterior chamber width measurement by high speed optical coherence tomography." *Ophthalmology* 112(2): 238-244.

Goldstein, L. E., J. A. Muffat, et al. (2003). "Cytosolic beta-amyloid deposition and supranuclear cataracts in lenses from people with Alzheimer's disease." *Lancet* 361(9365): 1258-1265.

Golubovic, B., B. E. Bouma, et al. (1996). "Thin crystal, room-temperature Cr/sup 4 +/:forstefite laser using near-infrared pumping." *Optics Letters* 21(24): 1993-1995.

Gonzalez, S. and Z. Tannous (2002). "Real-time, in vivo confocal reflectance microscopy of basal cell carcinoma." *Journal of the American Academy of Dermatology* 47(6): 869-874.

Gordon, M. O. and M. A. Kass (1999). "The Ocular Hypertension Treatment Study: design and baseline description of the participants." *Archives of Ophthalmology* 117(5): 573-83.

Grayson, T. P., J. R. Torgerson, et al. (1994). "Observation of a Nonlocal Pancharatnam Phase-Shift in the Process of Induced Coherence without Induced Emission." *Physical Review* A 49(1): 626-628.

Greaney, M. J., D. C. Hoffman, et al. (2002). "Comparison of optic nerve imaging methods to distinguish normal eyes from those with glaucoma." *Investigative Ophthalmology & Visual Science* 43(1): 140-5.

Greenfield, D. S., H. Bagga, et al. (2003). "Macular thickness changes in glaucomatous optic neuropathy detected using optical coherence tomography." *Archives of Ophthalmology* 121(1): 41-46.

Greenfield, D. S., R. W. Knighton, et al. (2000). "Effect of corneal polarization axis on assessment of retinal nerve fiber layer thickness by scanning laser polarimetry." *American Journal of Ophthalmology* 129(6): 715-722.

Griffin, R. A., D. D. Sampson, et al. (1995). "Coherence Coding for Photonic Code-Division Multiple-Access Networks." *Journal of Lightwave Technology* 13(9): 1826-1837.

Guedes, V., J. S. Schuman, et al. (2003). "Optical coherence tomography measurement of macular and nerve fiber layer thickness in normal and glaucomatous human eyes." *Ophthalmology* 110(1): 177-189.

Gueugniaud, P. Y., H. Carsin, et al. (2000). "Current advances in the initial management of major thermal burns. [Review] [76refs]." *Intensive Care Medicine* 26(7): 848-56.

Guido, S. and R. T. Tranquillo (1993). "A Methodology for the Systematic and Quantitative Study of Cell Contact Guidance in Oriented Collagen Gels—Correlation of Fibroblast Orientation and Gel Birefringence." *Journal of Cell Science* 105: 317-331.

Gurses-Ozden, R., H. Ishikawa, et al. (1999). "Increasing sampling density improves reproducibility of optical coherence tomography measurements." *Journal of Glaucoma* 8(4): 238-41.

Guzzi, R. (1998). "Scattering Theory from Homogeneous and Coated Spheres." 1-11.

Haberland, U. B., Vladimir; Schmitt, Hans J. (1996). "Optical coherent tomography of scattering media using electrically tunable near-infrared semiconductor laser." *Applied Optics* Draft Copy.

Haberland, U. R., Walter; Blazek, Vladimir; Schmitt, Hans J. (1995). "Investigation of highly scattering media using near-infrared continuous wave tunable semiconductor laser." *Proc. SPIE*, 2389: 503-512.

Hale, G. M. and M. R. Querry (1973). "Optical-Constants of Water in 200-Nm to 200-Mum Wavelength Region." *Applied Optics* 12(3): 555-563.

Hammer, D. X., R. D. Ferguson, et al. (2002). "Image stabilization for scanning laser ophthalmoscopy." *Optics Express* 10(26): 1542.

Hara, T., Y. Ooi, et al. (1989). "Transfer Characteristics of the Microchannel Spatial Light-Modulator." *Applied Optics* 28(22): 4781-4786.

Harland, C. C., S. G. Kale, et al. (2000). "Differentiation of common benign pigmented skin lesions from melanoma by high-resolution ultrasound." *British Journal of Dermatology* 143(2): 281-289.

Hartl, I., X. D. Li, et al. (2001). "Ultrahigh-resolution optical coherence tomgraphy using continuum generation in an air-silica microstructure optical fiber." *Optics Letters* 26(9): 608-610.

Hassenstein, A., A. A. Bialasiewicz, et al. (2000). "Optical coherence tomography in uveitis patients." *American Journal of Ophthalmoloqv* 130(5): 669-70.

Hattenhauer, M. G., D. H. Johnson, et al. (1998). "The probability of blindness from open-angle glaucoma. [see comments]." *Ophthalmology* 105(11): 2099-104.

Hausler, G., J. M. Herrmann, et al. (1996). "Observation of light propagation in volume scatterers with 10(11)-fold slow motion." *Optics Letters* 21(14): 1087-1089.

Hazebroek, H. F. and A. A. Holscher (1973). "Interferometric Ellipsometry." *Journal of Physics E-Scientific Instruments* 6(9): 822-826.

Hazebroek, H. F. and W. M. Visser (1983). "Automated Laser Interferometric Ellipsometry and Precision Reflectometry." *Journal of Physics E-Scientific Instruments* 16(7): 654-661.

He, Z. Y., N. Mukohzaka, et al. (1997). "Selective image extraction by synthesis of the coherence function using two-dimensional optical lock-in amplifier with microchannel spatial light modulator." *Ieee Photonics Technology Letters* 9(4): 514-516.

Hee, M. R., J. A. Izatt, et al. (1993). "Femtosecond Transillumination Optical Coherence Tomography." *Optics Letters* 18(12): 950-952.

Hee, M. R., J. A. Izatt, et al. (1995). "Optical coherence tomography of the human retina." *Archives of Ophthalmology* 113(3): 325-32.

Hee, M. R., C. A. Puliafito, et al. (1998). "Topography of diabetic macular edema with optical coherence tomography." *Ophthalmology* 105(2): 360-70.

Hee, M. R., C. A. Puliafito, et al. (1995). "Quantitative assessment of macular edema with optical coherence tomography." *Archives of Ophthalmology* 113(8): 1019-29.

Hellmuth, T. and M. Welle (1998). "Simultaneous measurement of dispersion, spectrum, and distance with a fourier transform spectrometer." *Journal of Biomedical Optics* 3(1): 7-11.

Hemenger, R. P. (1989). "Birefringence of a medium of tenuous parallel cylinders." *Applied Optics* 28(18): 4030-4034.

Henry, M. (1981). "Fresnel-Arago Laws for Interference in Polarized-Light—Demonstration Experiment." *American Journal of Physics* 49(7): 690-691.

Herz, P. R., Y. Chen, et al. (2004). "Micromotor endoscope catheter for in vivo, ultrahigh-resolution optical coherence tomography." *Optics Letters* 29(19): 2261-2263.

Hirakawa, H., H. Iijima, et al. (1999). "Optical coherence tomography of cystoid macular edema associated with retinitis pigmentosa." *American Journal of Ophthalmology* 128(2): 185-91.

Hitzenberger, C. K., A. Baumgartner, et al. (1994). "Interferometric Measurement of Corneal Thickness with Micrometer Precision." *American Journal of Ophthalmology* 118(4): 468-476.

Hitzenberger, C. K., A. Baumgartner, et al. (1999). "Dispersion effects in partial coherence interferometry: Implications for intraocular ranging." *Journal of Biomedical Optics* 4(1): 144-151.

Hitzenberger, C. K., A. Baumgartner, et al. (1998). "Dispersion induced multiple signal peak splitting in partial coherence interferometry." *Optics Communications* 154(4): 179-185.

Hitzenberger, C. K., M. Danner, et al. (1999). "Measurement of the spatial coherence of superluminescent diodes." *Journal of Modern Optics* 46(12): 1763-1774.

Hitzenberger, C. K. and A. F. Fercher (1999). "Differential phase contrast in optical coherence tomography." *Optics Letters* 24(9): 622-624.

Hitzenberger, C. K., M. Sticker, et al. (2001). "Differential phase measurements in low-coherence interferometry without 2 pi ambiguity." *Optics Letters* 26(23): 1864-1866.

Hoeling, B. M., A. D. Fernandez, et al. (2000). "An optical coherence microscope for 3-dimensional imaging in developmental biology." *Optics Express* 6(7): 136-146.

Hoerauf, H., C. Scholz, et al. (2002). "Transscleral optical coherence tomography: a new imaging method for the anterior segment of the eye." *Archives of Ophthalmology* 120(6): 816-9.

Hoffmann, K., M. Happe, et al. (1998). "Optical coherence tomography (OCT) in dermatology." *Journal of Investigative Dermatology* 110(4): 583-583.

Hoh, S. T., D. S. Greenfield, et al. (2000). "Optical coherence tomography and scanning laser plarimetry in normal, ocular hypertensive, and glaucomatous eyes." *American Journal of Ophthalmology* 129(2): 129-35.

Hohenleutner, U., M. Hilbert, et al. (1995). "Epidermal Damage and Limited Coagulation Depth with the Flashlamp-Pumped Pulsed Dye-Laser—a Histochemical-Study." *Journal of Investigative Dermatology* 104(5): 798-802.

Holland, A. J. A., H. C. O. Martin, et al. (2002). "Laser Doppler imaging prediction of burn wound outcome in children." *Burns* 28(1): 11-17.

Hotate, K. and T. Okugawa (1994). "Optical Information-Processing by Synthesis of the Coherence Function." *Journal of Lightwave Technology* 12(7): 1247-1255.

Hourdakis, C. J. and A. Perris (1995). "A Monte-Carlo Estimation of Tissue Optical-Properties for Use in Laser Dosimetry." *Physics in Medicine and Biology* 40(3): 351-364.

Hu, Z., F. Li, et al. (2000). "Wavelength-tunable narrow-linewidth semiconductor fiber-ring laser." *IEEE Photonics Technology Letters* 12(8): 977-979.

Huang, F., W. Yang, et al. (2001). "Quadrature spectral interferometric detection and pulse shaping." *Optics Letters* 26(6): 382-384.

Huang, X. R. and R. W. Knighton (2002). "Linear birefringence of the retinal nerve fiber layer measured in vitro with a multispectral imaging micropolarimeter." *Journal of Biomedical Optics* 7(2): 199-204.

Huber, R., M. Wojtkowski, et al. (2005). "Amplified, frequency swept lasers for frequency domain reflectometry and OCT imaging: design and scaling principles." *Optics Express* 13(9): 3513-3528.

Hunter, D. G., J. C. Sandruck, et al. (1999). "Mathematical modeling of retinal birefringence scanning." *Journal of the Optical Society of America a-Optics Image Science and Vision* 16(9): 2103-2111.

Hurwitz, H. H. and R. C. Jones (1941). "A new calculus for the treatment of optical systems II. Proof of three general equivalence theorens." *Journal of the Optical Society of America* 31(7): 493-499.

Huttner, B., C. De Barros, et al. (1999). "Polarization-induced pulse spreading in birefringent optical fibers with zero differential group delay." *Optics Letters* 24(6): 370-372.

Huttner, B., B. Gisin, et al. (1999). "Distributed PMD measurement with a polarization-OTDR in optical fibers." *Journal of Lightwave Technology* 17(10): 1843-1848.

Huttner, B., J. Reecht, et al. (1998). "Local birefringence measurements in single-mode fibers with coherent optical frequency-domain reflectometry." Ieee Photonics Technology Letters 10(10): 1458-1460.

Hyde, S. C. W., N. P. Barry, et al. (1995). "Sub-100-Mu-M Depth-Resolved Holographic Imaging through Scattering Media in the near-Infrared." Optics Letters 20(22): 2330-2332.

Hyde, S. C. W., N. P. Barry, et al. (1995). "Depth-Resolved Holographic Imaging through Scattering Media by Photorefraction." Optics Letters 20(11): 1331-1333.

Iftimia, N. V., B. E. Bouma, et al. (2004). "Adaptive ranging for optical coherence tomography." Optics Express 12(17): 4025-4034.

Iida, T., N. Hagimura, et al. (2000). "Evaluation of central serous chorioretinopathy with optical coherence tomography." American Journal of Ophthalmology 129(1): 16-20.

Imai, M., H. Iijima, et al. (2001). "Optical coherence tomography of tractional macular elevations in eyes with proliferative diabetic retinopathy. [republished in Am J Ophthalmol. 2001 Sep. 132(3):458-61 ; 11530091.]." American Journal of Ophthalmology 132(1): 81-4.

Indebetouw, G. and P. Klysubun (2000). "Imaging through scattering media with depth resolution by use of low-coherence gating in spatiotemporal digital holography." Optics Letters 25(4): 212-214.

Ip, M. S., B. J. Baker, et al. (2002). "Anatomical outcomes of surgery for idiopathic macular hole as determined by optical coherence tomography." Archives of Ophthalmology 120(1): 29-35.

Ismail, R., V. Tanner, et al. (2002). "Optical coherence tomography imaging of severe commotio retinae and associated macular hole." British Journal of Ophthalmology 86(4): 473-4.

Izatt, J. A., M. R. Hee, et al. (1994). "Optical Coherence Microscopy in Scattering Media." Optics Letters 19(8): 590-592.

Izatt, J. A., M. R. Hee, et al. (1994). "Micrometer-scale resolution imaging of the anterior eye in vivo with optical coherence tomography." Archives of Ophthalmology 112 (12): 1584-9.

Izatt, J. A., M. D. Kulkami, et al. (1997). "In vivo bidirectional color Doppler flow imaging of picoliter blood volumes using optical coherence tomography." Optics Letters 22(18): 1439-1441.

Izatt, J. A., M. D. Kulkarni, et al. (1996). "Optical coherence tomography and microscopy in gastrointestinal tissues." IEEE Journal of Selected Topics in Quantum Electronics 2(4): 1017.

Jacques, S. L., J. S. Nelson, et al. (1993). "Pulsed Photothermal Radiometry of Port-Wine-Stain Lesions." Applied Optics 32(13): 2439-2446.

Jacques, S. L., J. R. Roman, et al. (2000). "Imaging superficial tissues with polarized light." Lasers in Surgery and Medicine 26(2): 119-129.

Jang, I. K., B. E. Bouma, et al. (2002). "Visualization of coronary atherosclerotic plaques in patients using optical coherence tomography: Comparison with intravascular ultrasound." Journal of the American College of Cardiology 39(4): 604-609.

Jang, I. K., B. D. MacNeill, et al. (2002). "In-vivo characterization of coronary plaques in patients with ST elevation acute myocardial infarction using optical coherence tomography (OCT)." Circulation 106(19): 698-698 3440 Suppl. S,.

Jang, I. K., G. J. Tearney, et al. (2000). "Comparison of optical coherence tomography and intravascular ultrasound for detection of coronary plaques with large lipid-core in living patients." Circulation 102(18): 509-509.

Jeng, J. C., A. Bridgeman, et al. (2003). "Laser Doppler imaging determines need for excision and grafting in advance of clinical judgment: a prospective blinded trial." Burns 29(7): 665-670.

Jesser, C. A., S. A. Boppart, et al. (1999). "High resolution imaging of transitional cell carcinoma with optical coherence tomography: feasibility for the evaluation of bladder pathology." British Journal of Radiology 72: 1170-1176.

Johnson, C. A., J. L. Keltner, et al. (2002). "Baseline visual field characteristics in the ocular hypertension treatment study." Ophthalmology 109(3): 432-7.

Jones, R. C. (1941). "A new calculus for the treatment of optical systems III. The Sohncke theory of optical activity." Journal of the Optical Society of America 31 (7): 500-503.

Jones, R. C. (1941). "A new calculus for the treatment of optical systems I. Description and discussion of the calculus." Journal of the Optical Society of America 31(7): 488-493.

Jones, R. C. (1942). "A new calculus for the treatment of optical systems. IV." Journal of the Optical Society of America 32(8): 486-493.

Jones, R. C. (1947). "A New Calculus for the Treatment of Optical Systems .6. Experimental Determination of the Matrix." Journal of the Optical Society of America 37(2): 110-112.

Jones, R. C. (1947). "A New Calculus for the Treatment of Optical Systems .5. A More General Formulation, and Description of Another Calculus." Journal of the Optical Society of America 37(2): 107-110.

Jones, R. C. (1948. "A New Calculus for the Treatment of Optical Systems .7. Properties of the N-Matrices." Journal of the Optical Society of America 38(8): 671-685.

Jones, R. C. (1956). "New Calculus for the Treatment of Optical Systems .8. Electomagnetic Theory." Journal of the Optical Society of America 46(2): 126-131.

Jopson, R. M., L. E. Nelson, et al. (1999). "Measurement of second-order polarization-mode dispersion vectors in optical fibers." Ieee Photonics Technology Letters 11 (9): 1153-1155.

Jost, B. M., A. V. Sergienko, et al. (1998). "Spatial correlations of spontaneously down-converted photon pairs detected with a single-photon-sensitive CCD camera." Optics Express 3(2): 81-88.

Kaplan, B., E. Compain, et al. (2000). "Phase-modulated Mueller ellipsometry characterization of scattering by latex sphere suspensions." Applied Optics 39 (4): 629-636.

Kass, M. A., D. K. Heuer, et al. (2002). "the Ocular Hypertension Treatment Study: a randomized trial determines that topical ocular hypotensive medication delays or prevents the onset of primary open-angle glaucoma." Archives of Ophthalmology 120(6): 701-13; discussion 829-30.

Kasuga, Y., J. Arai, et al. (2000). "Optical coherence tomography to confirm early closure of macular holes." American Journal of Ophthalmology 130(5): 675-6.

Kaufman, T., S. N. Lusthaus, et al. (1990). "Deep Partial Skin Thickness Burns—a Reproducible Animal-Model to Study Burn Wound-Healing." Burns 16(1): 13-16.

Kemp, N. J., J. Park, et al. (2005). "High-Sensitivity determination of birefringence in turbid media with enhanced polarization-sensitive optical coherence tomography." Journal of the Optical Society of America a-Optics Image Science and Vision 22(3): 552-560.

Kerrigan-Baumrind, L. A., H. A. Quigley, et al. (2000). "Number of ganglion cells in glaucoma eyes compared with threshold visual field tests in the same persons." Investigative Ophthalmology & Visual Science 41(3): 741-8.

Kesen, M. R., G. L. Spaeth, et al. (2002). "The Heidelberg Retina Tomograph vs clinical impression in the diagnosis of glaucoma." American Journal of Ophthalmology 133(5): 613-6.

Kienle, A. and R. Hibst (1995). "A New Optimal Wavelength for Treatment of Port-Wine Stains." Physics in Medicine and Biology 40(10): 1559-1576.

Kienle, A., L. Lilge, et al. (1996). "Spatially resolved absolute diffuse reflectance measurements for noninvasive determination of the optical scattering and absorption coefficients ob biological tissue." Applied Optics 35(13): 2304-2314.

Kim, B. Y. and S. S. Choi (1981). "Analysis and Measurement of Birefringence in Single-Mode Fibers Using the Backscattering Method." Optics Letters 6(11): 578-580.

Kimel, S., L. O. Svaasand, et al. (1994). "Differential Vascular-Response to Laser Photothermolysis." Journal of Investigative Dermatology 103(5): 693-700.

Kloppenberg, F. W. H., G. Beerthuizen, et al. (2001). "Perfusion of burn wounds assessed by Laser Doppler Imaging is related to burn depth and healing time." Burns 27(4): 359-363.

Knighton, R. W. and X. R. Huang (2002). "Analytical methods for scanning laser polarimetry." Optics Express 10(21): 1179-1189.

Knighton, R. W., X. R. Huang, et al. (2002). "Analytical model of scanning laser polarimetry for retinal nerve fiber layer assessment." Investigative Ophthalmology & Visual Science 43(2): 383-392.

Knuettel, A. R. S., Joseph M.: Shay, M.; Knutson, Jay R. (1994). "Stationary low-coherence light imaging and spectroscopy using a CCD camera." *Proc. SPIE*, vol. 2135: p. 239-250.

Knuttel, A. and M. Boehlau-Godau (2000). "Spatially confined and temporally resolved refractive index and scattering evaluation in human skin performed with optical coherence tomography." *Journal of Biomedical Optics* 5(1): 83-92.

Knuttel, A. and J. M. Schmitt (1993). "Stationary Depth-Profiling Reflectometer Based on Low-Coherence Interferometry." *Optics Communications* 102(3-4): 193-198.

Knuttel, A., J. M. Schmitt, et al. (1994). "Low-Coherence Reflectometry for Stationary Lateral and Depth Profiling with Acoustooptic Deflectors and a Ccd Camera." *Optics Letters* 19(4): 302-304.

Kobayashi, M., H. Hanafusa, et al. (1991). "Polarization-Independent Interferometric Optical-Time-Domain Reflectometer." *Journal of Lightwave Technology* 9(5): 623-628.

Kolios, M. C., M. D. Sherar, et al. (1995). "Large Blood-Vessel Cooling in Heated Tissues—a Numerical Study." *Physics in Medicine and Biology* 40(4): 477-494.

Koozekanani, D., K. Boyer, et al. (2001). "Retinal thickness measurements from optical coherence tomography using a Markov boundary model." *Ieee Transactions on Medical Imaging* 20(9): 900-916.

Kop, R. H. J. and R. Sprik (1995). "Phase-sensitive interferometry with ultrashort optical pulses." *Review of Scientific Instruments* 66(12): 5459-5463.

Kramer, R. Z., J. Bella, et al. (1999). "Sequence dependent conformational variations of collagen triple-helical structure." *Nature Structural Biology* 6(5): 454-7.

Kulkarni, M. D., T. G. van Leeuwen, et al. (1998). "Velocity-estimation accuracy and frame-rate limitations in color Doppler optical coherence tomography." *Optics Letters* 23(13): 1057-1059.

Kwon, Y. H., C. S. Kim, et al. (2001). "Rate of visual field loss and long-term visual outcome in primary open-angle glaucoma." *American Journal of Ophthalmology* 132(1): 47-56.

Kwong, K. F., D. Yankelevich, et al. (1993). "400-Hz Mechanical Scanning Optical Delay-Line." *Optics Letters* 18(7): 558-560.

Landers, J., I. Goldberg, et al. (2002). "Analysis of risk factors that may be associated with progression from ocular hypertension to primary open angle glaucoma." *Clin Experiment Ophthalmogy* 30(4): 242-7.

Laszlo, A. and A. Venetianer (1998). Heat resistance in mammalian cells: Lessons and challenges. *Stress of Life*. 851: 169-178.

Laszlo, A. and A. Venetianer (1998). "Heat resistance in mammalian cells: lessons and challenges. [Review] [52 refs]." *Annals of the New York Academy of Sciences* 851: 169-78.

Laufer, J., R. Simpson, et al. (1998). "Effect of temperature on the optical properties of ex vivo human dermis and subdermis." *Physics in Medicine and Biology* 43(9): 2479-2489.

Lederer, D. E., J. S. Schuman, et al. (2003). "Analysis of macular volume in normal and glaucomatous eyes using optical coherence tomography." *American Journal of Ophthalmology* 135(6): 838-843.

Lee, P. P., Z. W. Feldman, et al. (2003). "Longitudinal prevalence of major eye diseases." *Archives of Ophthalmology* 121(9): 1303-1310.

Lehrer, M. S., T. T. Sun, et al. (1998). "Strategies of epithelial repair: modulation of stem cell and transit amplifying cell proliferation." *Journal of Cell Sciences* 111(Pt 19): 2867-75.

Leibowitz, H. M., D. E. Krueger, et al. (1980). "The Framingham Eye Study monograph: An ophthalmological and epidemiological study of cataract, glaucoma, diabetic retinopathy, macular degeneration, and visual acuity in a general population of 2631 adults, 1973-1975." *Survey of Ophthalmology* 24(Suppl): 335-610.

Leitgeb, R., C. K. Hitzenberger, et al. (2003). "Performance of fourier domain vs. time domain optical coherence tomography." *Optics Express* 11(8): 889-894.

Leitgeb. R., L. F. Schmetterer, et al. (2002). "Flow velocity measurements by frequency domain short coherence interferometry." *Proc. SPIE* 4619: 16-21.

Leitgeb, R. A., W. Drexler, et al. (2004). "Ultrahigh resolution Fourier domain optical coherence tomography." *Optics Express* 12(10): 2156-2165.

Leitgeb, R. A., C. K. Hitzenberger, et al. (2003). "Phase-shifting algorithm to achieve high-speed long-depth-range probing by frequency-domain optical coherence tomography." *Optics Letters* 28(22): 2201-2203.

Leitgeb, R. A., L. Schmetterer, et al. (2003). "Real-time assessment of retinal blood flow with ultrafast acquisition by color Doppler Fourier domain optical coherence tomography." *Optics Express* 11(23): 3116-3121.

Leitgeb, R. A., L. Schmetterer, et al. (2004). "Real-time measurement of in vitro flow by Fourier-domain color Doppler optical coherence tomography." *Optics Letters* 29 (2): 171-173.

LeRoyBrehonnet, F. and B. LeJeune (1997). "Utilization of Mueller matrix formalism to obtain optical targets depolarization and polarization properties." *Progress in Quantum Electronics* 21(2): 109-151.

Leske, M. C., A. M. Connell, et al. (1995). "Risk factors for open-angle glaucoma. The Barbados Eye Study. [see comments]." *Archives of Ophthalmology* 113(7): 918-24.

Leske, M. C., A. M. Connell, et al. (2001). "Incidence of open-angle glaucoma: the Barbados Eye Studies. The Barbados Eye Studies Group. [see comments]." *Archives of Ophthalmology* 119(1): 89-95.

Leske, M. C., A. Heijl, et al. (1999). "Early Manifest Glaucoma Trial. Design and Baseline Data." *Ophthalmology* 106(11): 2144-2153.

Lewis, S. E., J. R. DeBoer, et al. (2005). "Sensitive, selective, and analytical improvements to a porous silicon gas sensor." *Sensors and Actuators B: Chemical* 110(1): 54-65.

Lexer, F., C. K. Hitzenberger, et al. (1999). "Dynamic coherent focus OCT with depth- independent transversal resolution." *Journal of Modern Optics* 46(3): 541-553.

Li, X., C. Chudoba, et al. (2000). "Imaging needle for optical coherence tomography." *Optics Letters* 25: 1520-1522.

Li, X., T. H. Ko, et al. (2001). "Intraluminal fiber-optic Doppler imaging catheter for structural and functional optical coherence tomography." *Optics Letters* 26: 1906-1908.

Liddington, M. I. and P. G. Shakespeare (1996). "Timing of the thermographic assessment of burns." *Burns* 22(1): 26-8.

Lindmo, T., D. J. Smithies, et al. (1998). "Accuracy and noise in optical Doppler tomography studied by Monte Carlo simulation." *Physics in Medicine and Biology* 43(10): 3045-3064.

Liu, J., X. Chen, et al. (1999). "New thermal wave aspects on burn evaluation of skin subjected to instantaneous heating." *IEEE Transactions on Biomedical Engineering* 46(4): 420-8.

Luke, D. G., R. McBride, et al. (1995). "Polarization mode dispersion minimization in fiber-wound piezoelectric cylinders." *Optics Letters* 20(24): 2550-2552.

MacNeill, B. D., I. K. Jang, et al. (2004). "Focal and multi-focal plaque distributions in patients with macrophage acute and stable presentations of coronary artery disease." *Journal of the American College of Cardiology* 44(5): 972-979.

Mahgerefteh, D. and C. R. Menyuk (1999). "Effect of first-order PMD compensation on the statistics of pulse broadening in a fiber with randomly varying birefringence." *Ieee Photonics Technology Letters* 11(3): 340-342.

Maitland, D. J. and J. T. Walsh, Jr. (1997). "Quantitative measurements of linear birefringence during heating of native collagen." *Lasers in Surgery & Medicine* 20 (3): 310-8.

Majaron, B., S. M. Srinivas, et al. (2000). "Deep coagulation of dermal collagen with repetitive Er : YAG laser irradiation." *Lasers in Surgery and Medicine* 26(2): 215-222.

Mansuripur, M. (1991). "Effects of High-Numerical-Aperture Focusing on the State of Polarization in Optical and Magnetooptic Data-Storage Systems." *Applied Optics* 30(22): 3154-3162.

Marshall, G. W., S. J. Marshall, et al. (1997). "The dentin substrate: structure and properties related to bonding." *Journal of Dentistry* 25(6): 441-458.

Martin, P. (1997). "Wound healing—Aiming for perfect skin regeneration." *Science* 276 (5309): 75-81.

Martinez, O. E. (1987). "3000 Times Grating Compressor with Positive Group-Velocity Dispersion— Application to Fiber Compensation in 1.3-1.6 Mu-M Region." *Ieee Journal of Quantum Electronics* 23(1): 59-64.

Martinez, O. E., J. P. Gordon, et al. (1984). "Negative Group-Velocity Dispersion Using Refraction." *Journal of the Optical Society of America a-Optics Image Science and Vision* 1(10): 1003-1006.

McKinney, J. D., M. A. Webster, et al. (2000). "Characterization and imaging in optically scattering media by use of laser speckle and a variable-coherence source." *Optics Letters* 25(1): 4-6.

Miglior, S., M. Casula, et al. (2001). "Clinical ability of Heidelberg retinal tomograph examination to detect glaucomatous visual field changes." *Ophthalmology* 108 (9): 1621-7.

Milner, T. E., D. M. Goodman, et al. (1996). "Imaging laser heated subsurface chromophores in biological materials: Determination of lateral physical dimensions." *Physics in Medicine and Biology* 41(1): 31-44.

Milner, T. E., D. M. Goodman, et al. (1995). "Depth Profiling of Laser-Heated Chromophores in Biological Tissues by Pulsed Photothermal Radiometry." *Journal of the Optical Society of America a-Optics Image Science and Vision* 12 (7): 1479-1488.

Milner, T. E., D. J. Smities, et al. (1996). "Depth determination of chromophores in human skin by pulsed photothermal radiometry." *Applied Optics* 35(19): 3379-3382.

Mishchenko, M. I. and J. W. Hovenier (1995). "Depolarization of Light Backscattered by Randomly Oriented Nonspherical Particles." *Optics Letters* 20(12): 1356-&.

Mistlberger, A., J. M. Liebmann, et al. (1999). "Heidelberg retina tomography an doptical coherence tomography in normal, ocular-hypertensive, and glaucomatous eyes." *Ophthalmology* 106(10): 2027-32.

Mitsui, T. (1999). "High-speed detection of ballistic photons propagating through suspensions using spectral interferometry." *Japanese Journal of Applied Physics* Part 1-Regular Papers Short Notes & Review Papers 38(5 A): 2978-2982.

Molteno, A. C., N. J. Bosma, et al. (1999). "Otago glaucoma surgery outcome study: long-term results of trabeculectomy—1976 to 1995." *Ophthalmology* 106(9): 1742-50.

Morgner, U., W. Drexler, et al. (2000). "Spectroscopic optical coherence tomography." *Optics Letters* 25(2): 111-113.

Morgner, U., F. X. Kartner, et al. (1999). "Sub-two-cycle pulses from a Kerr-lens mode-locked Ti : sapphire laser (vol 24, p. 411, 1999)." *Optics Letters* 24(13): 920-920.

Mourant, J. R., A. H. Hielscher, et al. (1998). "Evidence of intrinsic differences in the light scattering properties of tumorigenic and nontumorigenic cells." *Cancer Cytopathology* 84(6): 366-374.

Muller, M., J. Squier, et al. (1998). "Dispersion pre-compensation of 15 femtosecond optical pulses for high-numerical-aperture objectives." *Journal of Microscopy-Oxford* 191: 141-150.

Muscat, S., N. McKay, et al. (2002). "Repeatability and reproducibility of corneal thickness measurements by optical coherence tomography." *Investigative Ophthalmology & Visual Science* 43(6): 1791-5.

Musch, D. C., P. R. Lichter, et al. (1999). "The Collaborative Initial Glaucoma Treatment Study. Study Design, Methods, and Baseline Characteristics of Enrolled Patients." *Ophthalmology* 106: 653-662.

Neerken, S., Lucassen, G.W., Bisschop, M.A., Lenderink, E., Nuijs, T.A.M. (2004). "Characterization of age-related effects in human skin: A comparative study that applies confocal laser scanning microscopy and optical coherence tomography." *Journal of Biomedical Optics* 9(2): 274-281.

Nelson, J. S., K. M. Kelly, et al. (2001). "Imaging blood flow in human port-wine stain in situ and in real time using optical Doppler tomography." *Archives of Dermatology* 137(6): 741-744.

Newson, T. P., F. Farahi, et al. (1988). "Combined Interferometric and Polarimetric Fiber Optic Temperature Sensor with a Short Coherence Length Source." *Optics Communications* 68(3): 161-165.

November, L. J. (1993). "Recovery of the Matrix Operators in the Similarity and Congruency Transformations—Applications in Polarimetry." *Journal of the Optical Society of America a-Optics Image Science and Vision* 10(4): 719-739.

Oh, W. Y., S. H. Yun, et al. (2005). "Wide tuning range wavelength-swept laser with two semiconductor optical amplifiers." *Ieee Photonics Technology Letters* 17(3): 678-680.

Oka, K. and T. Kato (1999). "Spectroscopic polarimetry with a channeled spectrum." *Optics Letters* 24(21): 1475-1477.

Okugawa, T. and K. Rotate (1996). "Real-time optical image processing by synthesis of the coherence function using real-time holography." *Ieee Photonics Technology Letters* 8(2): 257-259.

Oshima, M., R. Torii, et al. (2001). "Finite element simulation of blood flow in the cerebral artery." *Computer Methods in Applied Mechanics and Engineering* 191 (6-7): 661-671.

Pan, Y. T., H. K. Xie, et al. (2001). "Endoscopic optical coherence tomography based on a microelectromechanical mirror." *Optics Letters* 26(24): 1966-1968.

Parisi, V., G. Manni, et al. (2001). "Correlation between optical coherence tomography, pattern electroretinogram, and visual evoked potentials in open-angle glaucoma patients." *Ophthalmology* 108(5): 905-12.

Park, B. H., M. C. Pierce, et al. (2005). "Real-time fiber-based multi-functional spectral-domain optical coherence tomography at 1.3 mu m." *Optics Express* 13(11): 3931-3944.

Park, D. H., . W. Hwang, et al. (1998). "Use of laser Doppler flowmetry for estimation of the depth of burns." *Plastic and Reconstructive Surgery* 101(6): 1516-1523.

Pendry, J. B., A. J. Holden, et al. (1999). "Magnetism from conductors and enhanced nonlinear phenomena." *Ieee Transactions on Microwave Theory and Techniques* 47(11): 2075-2084.

Penninckx, D. and V. Morenas (1999). "Jones matrix of polarization mode dispersion." *Optics Letters* 24(13): 875-877.

Pierce, M. C., M. Shishkov, et al. (2005). "Effects of sample arm motion in endoscopic polarization-sensitive optical coherence tomography." *Optics Express* 13(15): 5739-5749.

Pircher, M., E. Gotzinger, et al. (2003). "Measurement and imaging of water concentration in human cornea with differential absorption optical coherence tomography." *Optics Express* 11(18): 2190-2197.

Pircher, M., E. Gotzinger, et al. (2003). "Speckle reduction in optical coherence tomography by frequency compounding." *Journal of Biomedical Optics* 8(3): 565-569.

Podoleanu, A. G., G. M. Dobre, et al. (1998). "En-face coherence imaging using galvanometer scanner modulation." *Optics Letters* 23(3): 147-149.

Podoleanu, A. G. and D. A. Jackson (1999). "Noise analysis of a combined optical coherence tomograph and a confocal scanning ophthalmoscope." *Applied Optics* 38(10): 2116-2127.

Podoleanu, A. G., J. A. Rogers, et al. (2000). "Three dimensional OCT images from retina and skin." *Optics Express* 7(9): 292-298.

Podoleanu, A. G., M. Seeger, et al. (1998). "Transversal and longitudinal images from the retina of the living eye using low coherence reflectometry." *Journal of Biomedical Optics* 3(1): 12-20.

Poole, C. D. (1988). "Statistical Treatment of Polarization Dispersion in Single-Mode Fiber." *Optics Letters* 13(8): 687-689.

Povazay, B., K. Bizheva, et al. (2002). "Submicrometer axial resolution optical coherence tomography." *Optics Letters* 27(20): 1800-1802.

Qi, B., A. P. Himmer, et al. (2004). "Dynamic focus control in high-speed optical coherence tomography based on a microelectromechanical mirror." *Optics Communications* 232(1-6): 123-128.

Radhakrishnan, S., A. M. Rollins, et al. (2001). "Real-time optical coherence tomography of the anterior segment at 1310 nm." *Archives of Ophthalmology* 119(8): 1179-1185.

Rogers, A. J. (1981). "Polarization-Optical Time Domain Reflectometry—a Technique for the Measurement of Field Distributions." Applied Optics 20(6): 1060-1074.

Rollins, A. M. and J. A. Izatt (1999). "Optimal interferometer designs for optical coherence tomography." *Optics Letters* 24(21): 1484-1486.

Rollins, A. M., R. Ung-arunyawee, et al. (1999). "Real-time in vivo imaging of human gastrointestinal ultrastructure by use of endoscopic optical coherence tomography with a novel efficient interferometer design." *Optics Letters* 24(19): 1358-1360.

Rollins, A. M., S. Yazdanfar, et al. (2002). "Real-time in vivo colors Doppler optical coherence tomography." *Journal of Biomedical Optics* 7(1): 123-129.

Rollins, A. M., S. Yazdanfar, et al. (2000). "Imaging of human retinal hemodynamics using color Doppler optical coherence tomography." *Investigative Ophthalmology & Visual Science* 41(4): S548-S548.

Sandoz, P. (1997). "Wavelet transform as a processing tool in white-light interferometry." *Optics Letters* 22(14): 1065-1067.

Sankaran, V., M. J. Everett, et al. (1999). "Comparison of polarized-light propagation in biological tissue and phantoms." *Optics Letters* 24(15): 1044-1046.

Sankaran, V., J. T. Walsh, et al. (2000). "Polarized light propagation through tissue phanto, ehms containing densely packed scatterers." *Optics Letters* 25(4): 239-241.

Sarunic, M. V., M. A. Choma, et al. (2005). "Instantaneous complex conjugate resolved spectral domain and swept-source OCT using 3x3 fiber couplers." *Optics Express* 13(3): 957-967.

Sathyam, U. S., B. W. Colston, et al. (1999). "Evaluation of optical coherence quantitation of analytes in turbid media by use of two wavelengths." *Applied Optics* 38(10): 2097-2104.

Schmitt, J. M. (1997). "Array detection for speckle reduction in optical coherence microscopy." *Physics in Medicine and Biology* 42(7): 1427-1439.

Schmitt, J. M. (1999). "Optical coherence tomography (OCT): A review." *Ieee Journal of Selected Topics in Quantum Electronics* 5(4): 1205-1215.

Schmitt, J. M. and A. Knuttel (1997). "Model of optical coherence tomography of heterogeneous tissue." *Journal of the Optical Society of America a-Optics Image Science and Vision* 14(6): 1231-1242.

Schmitt, J. M., S. L. Lee, et al. (1997). "An optical coherence microscope with enhanced resolving power in thick tissue." *Optics Communications* 142(4-6): 203-207.

Schmitt, J. M., S. H. Xiang, et al. (1998). "Differential absorption imaging with optical coherence tomography." *Journal of the Optical Society of America a-Optics Image Science and Vision* 15(9): 2288-2296.

Schmitt, J. M., S. H. Xiang, et al. (1999). "Speckle in optical coherence tomography." *Journal of Biomedical Optics* 4(1): 95-105.

Schmitt, J. M., M. J. Yadlowsky, et al. (1995). "Subsurface Imaging of Living Skin with Optical Coherence Microscopy." *Dermatology* 191(2): 93-98.

Shi, H., J. Finlay, et al. (1997). "Multiwavelength 10-GHz picosecond pulse generation from a single-stripe semiconductor diode laser." *Ieee Photonics Technology Letters* 9(11): 1439-1441.

Shi, H., I. Nitta, et al. (1999). "Demonstration of phase correlation in multiwavelength mode-locked semiconductor diode lasers." *Optics Letters* 24(4): 238-240.

Simon, R. (1982). "The Connection between Mueller and Jones Matrices of Polarization Optics." *Optics Communications* 42(5): 293-297.

Smith, P. J. M., E.M.; Taylor, C.M.; Selviah, D.R.; Day, S.E.; Commander, L.G. "Variable-Focus Microlenses as a Potential Technology for Endoscopy.".

Smithies, D. J., T. Lindmo, et al. (1998). "Signal attenuation and localization in optical coherence tomgraphy studied by Monte Carlo simulation." *Physics in Medicine and Biology* 43(10): 3025-3044.

Sorin, W. V. and D. F. Gray (1992). "Simultaneous Thickness and Group Index Measurement Using Optical Low-Coherence Reflectometry." *Ieee Photonics Technology Letters* 4(1): 105-107.

Sticker, M., C. K. Hitzenberger, et al. (2001). "Quantitative differential phase measurement and imaging in transparent and turbid media by optical coherence tomography." *Optics Letters* 26(8): 518-520.

Sticker, M., M. Pircher, et al. (2002). "En face imaging of single cell layers by differential phase-contrast optical coherence microscopy." *Optics Letters* 27(13): 1126-1128.

Stoller, P., B. M. Kim, et al. (2002). "Polarization-dependent optical second-harmonic imaging of a rat-tail tendon." *Journal of Biomedical Optics* 7(2): 205-214.

Sun, C. S. (2003). "Multiplexing of fiber-optic acoustic sensors in a Michelson interferometer configuration." *Optics Letters* 28(12): 1001-1003.

Swanson, E. A., J. A. Izatt, et al. (1993). "In-Vivo Retinal Imaging by Optical Coherence Tomography." *Optics Letters* 18(21): 1864-1866.

Takada, K., A. Himeno, et al. (1991). "Phase-Noise and Shot-Noise Limited Operations of Low Coherence Optical-Time Domain Reflectometry." *Applied Physics Letters* 59(20): 2483-2485.

Takenaka, H. (1973). "Unified Formalism for Polarization Optics by Using Group-Theory I (Theory)." *Japanese Journal of Applied Physics* 12(2): 226-231.

Tanno, N., T. Ichimura, et al. (1994). "Optical Multimode Frequency-Domain Reflectometer." *Optics Letters* 19(8): 587-589.

Tan-no, N., T. Ichimura, et al. (1994). "Optical Multimode Frequency-Domain Reflectometer." *Optics Letters* 19(8): 587-589.

Targowski, P., M. Wojtkowski, et al. (2004). "Complex spectral OCT in human eye imaging in vivo." *Optics Communications* 229(1-6): 79-84.

Tearney, G. J., S. A. Boppart, et al. (1996). "Scanning single-mode fiber optic catheter- endoscope for optical coherence tomography (vol. 21, p. 543, 1996)." *Optics Letters* 21(12): 912-912.

Tearney, G. J., B. E. Bouma, et al. (1996). "Rapid acquisition of in vivo biological images by use of optical coherence tomography." *Optics Letters* 21(17): 1408-1410.

Tearney, G. J., B. E. Bouma, et al. (1997). "In vivo endoscopic optical biopsy with optical coherence tomography." *Science* 276(5321): 2037-2039.

Tearney, G. J., M. E. Brezinski, et al. (1996). "Catheter-based optical imaging of a human coronary artery." *Circulation* 94(11): 3013-3013.

Tearney, G. J., M. E. Brezinski, et al. (1997). "In vivo endoscopic optical biopsy with optical coherence tomography." *Science* 276(5321): 2037-9.

Tearney, G. J., M. E. Brezinski, et al. (1997). "Optical biopsy in human gastrointestinal tissue using optical coherence tomography." *American Journal of Gastroenterology* 92(10): 1800-1804.

Tearney, G. J., M. E. Brezinski, et al. (1995). "Determination of the refractive index of highly scattering human tissue by optical coherence tomography." *Optics Letters* 20(21): 2258-2260.

Tearney, G. J., I. K. Jang, et al. (2000). "Porcine coronary imaging in vivo by optical coherence tomography." *Acta Cardiologica* 55(4): 233-237.

Tearney, G. J., R. H. Webb, et al. (1998). "Spectrally encoded confocal microscopy." *Optics Letters* 23(15): 1152-1154.

Tearney, G. J., H. Yabushita, et al. (2003). "Quantification of macrophage content in atherosclerotic plaques by optical coherence tomography." *Circulation* 107(1): 113-119.

Tower, T. T. and R. T. Tranquillo (2001). "Alignment maps of tissues: I. Microscopic elliptical polarimetry." *Biophysical Journal* 81(5): 2954-2963.

Tower, T. T. and R. T. Tranquillo (2001). "Alignment maps of tissues: II. Fast harmonic analysis for imaging." *Biophysical Journal* 81(5): 2964-2971.

Troy, T. L. and S. N. Thennadil (2001). "Optical properties of human skin in the near infrared wavelength range of 1000 to 2200 nm." *Journal of Biomedical Optics* 6 (2): 167-176.

Vabre, L., A. Dubois, et al. (2002). "Thermal-light full-field optical coherence tomography." *Optics Letters* 27(7): 530-532.

Vakhtin, A. B., D. J. Kane, et al. (2003). "Common-path interferometer for frequency-domain optical coherence tomography." *Applied Optics* 42(34): 6953-6958.

Vakhtin, A. B., K. A. Peterson, et al. (2003). "Differential spectral interferometry: an imaging technique for biomedical applications." *Optics Letters* 28(15): 1332-1334.

Vakoc, B. J., S. H. Yun, et al. (2005). "Phase-resolved optical frequency domain imaging." *Optics Express* 13(14): 5483-5493.

van Leeuwen, T. G., M. D. Kulkarni, et al. (1999). "High-flow-velocity and shear-rate imaging by use of color Doppler optical coherence tomography." *Optics Letters* 24(22): 1584-1586.

Vansteenkiste, N., P. Vignolo, et al. (1993). "Optical Reversibility Theorems for Polarization—Application to Remote-Control of Polarization." *Journal of the Optical Society of America a-Optics Image Science and Vision* 10(10): 2240-2245.

Vargas, O., E. K. Chan, et al. (1999). "Use of an agent to reduce scattering in skin." *Lasers in Surgery and Medicine* 24(2): 133-141.

Wang, R. K. (1999). "Resolution improved optical coherence-gated tomography for imaging through biological tissues." *Journal of Modern Optics* 46(13): 1905-1912.

Wang, X. J., T. E. Milner, et al. (1997). "Measurement of fluid-flow-velocity profile in turbid media by the use of optical Doppler tomography." *Applied Optics* 36(1): 144-149.

Wang, X. J., T. E. Milner, et al. (1995). "Characterization of Fluid-Flow Velocity by Optical Doppler Tomography." *Optics Letters* 20(11): 1337-1339.

Wang, Y. M., J. S. Nelson, et al. (2003). "Optimal wavelength for ultrahigh-resolution optical coherence tomography." *Optics Express* 11(12): 1411-1417.

Wang, Y. M., Y. H. Zhao, et al. (2003). "Ultrahigh-resolution optical coherence tomography by broadband continuum generation from a photonic crystal fiber." *Optics Letters* 28(3): 182-184.

Watkins, L. R., S. M. Tan, et al. (1999). "Determination of interferometer phase distributions by use of wavelets." *Optics Letters* 24(13): 905-907.

Wetzel, J. (2001). "Optical coherence tomography in dermatology: a review." *Skin Research and Technology* 7(1): 1-9.

Wentworth, R. H. (1989). "Theoretical Noise Performance of Coherence-Multiplexed Interferometric Sensors." *Journal of Lightwave Technology* 7(6): 941-956.

Westphal, V., A. M. Rollins, et al. (2002). "Correction of geometric and refractive image distortions in optical coherence tomography applying Fermat's principle." *Optics Express* 10(9): 397-404.

Westphal, V., S. Yazdanfar, et al. (2002). "Real-time, high velocity-resolution color Doppler optical coherence tomography." *Optics Letters* 27(1): 34-36.

Williams, P. A. (1999). "Rotating-wave-plate Stokes polarimeter for differential group delay measurements of polarization-mode dispersion." *Applied Optics* 38(31): 6508-6515.

Wojtkowski, M., T. Bajraszewski, et al. (2003). "Real-time in vivo imaging by high-speed spectral optical coherence tomography." *Optics Letters* 28(19): 1745-1747.

Wojtkowski, M., A. Kowalczyk, et al. (2002). "Full range complex spectral optical coherence tomography technique in eye imaging." *Optics Letters* 27(16): 1415-1417.

Wojtkowski, M., R. Leitgeb, et al. (2002). "In vivo human retinal imaging by fourier domain optical coherence tomography." *Journal of Biomedical Optics* 7(3): 457-463.

Wojtkowski, M., R. Leitgeb, et al. (2002). "Fourier domain OCT imaging of the human eye in vivo." *Proc. SPIE* 4619: 230-236.

Wojtkowski, M., V. J. Srinivasan, et al. (2004). "Ultrahigh-resolution, high-speed, Fourier domain optical coherence tomography and methods for dispersion compensation." *Optics Express* 12(11): 2404-2422.

Wong, B. J. F., Y. H. Zhao, et al. (2004). "Imaging the internal structure of the rat cochlea using optical coherence tomography at 0.827 mu m and 1.3 mu m." *Otolaryngology-Head and Neck Surgery* 130(3): 334-338.

Yabushita, H. B., B.E.; Houser, S.L.; Aretz, H.T.; Jang, I.; Schlendorf, K.H.; Kauffman, C.R.; Shishkov, M.; Halpern, E.F.; Tearney, G.J. "Measurement of Thin Fibrous Caps in Atherosclerotic Plaques by Optical Coherence Tomography.".

Yang, C., A. Wax, et al. (2001). "Phase-dispersion optical tomography." *Optics Letters* 26(10): 686-688.

Yang, C., A. Wax, et al. (2001). "Phase-referenced interferometer with subwavelength and subhertz sensitivity applied to the study of cell membrane dynamics." *Optics Letters* 26(16): 1271-1273.

Yang, C. H., A. Wax, et al. (2001). "Phase-dispersion optical tomography." *Optics Letters* 26(10): 686-688.

Yang, C. H., A. Wax, et al. (2000). "Interferometric phase-dispersion microscopy." *Optics Letters* 25(20): 1526-1528.

Yang, V. X. D., M. L. Gordon, et al. (2002). "Improved phase-resolved optical Doppler tomography using the Kasai velocity estimator and histogram segmentation." *Optics Communications* 208(4-6): 209-214.

Yang, V. X. D., M. L. Gordon, et al. (2003). "High speed, wide velocity dynamic range Doppler optical coherence tomography (Part I): System design, signal processing, and performance." *Optics Express* 11(7): 794-809.

Yang, V. X. D., M. L. Gordon, et al. (2003). "High speed, wide velocity dynamic range Doppler optical coherence tomography (Part II): Imaging in vivo cardiac dynamics of Xenopus laevis." *Optics Express* 11(14): 1650-1658.

Yang, V. X. D., M. L. Gordon, et al. (2003). "High speed, wide velocity dynamic range Doppler optical coherence tomography (Part III): in vivo endoscopic imaging of blood flow in the rat and human gastrointestinal tracts." *Optics Express* 11(19): 2416-2424.

Yang, V. X. D., B. Qi, et al. (2003). "In vivo feasibility of endoscopic catheter-based Doppler optical coherence tomography." *Gastroenterology* 124(4): A49-A50.

Yao, G. and L. H. V. Wang (2000). "Theoretical and experimental studies of ultrasound-modulated optical tomography in biological tissue." *Applied Optics* 39(4): 659-664.

Yazdanfar, S. and J. A. Izatt (2002). "Self-referenced Doppler optical coherence tomography." *Optics Letters* 27(23): 2085-2087.

Yazdanfar, S., M. D. Kulkarni, et al. (1997). "High resolution imaging of in vivo cardiac dynamics using color Doppler optical coherence tomography." *Optics Express* 1 (13) : 424-431.

Yazdanfar, S., A. M. Rollins, et al. (2000). "Imaging and velocimetry of the human retinal circulation with color Doppler optical coherence tomography." *Optics Letters* 25(19): 1448-1450.

Yazdanfar, S., A. M. Rollins, et al. (2000). "Noninvasive imaging and velocimetry of human retinal blood flow using color Doppler optical coherence tomography." *Investigative Ophthalmology & Visual Science* 41(4): S548-S548.

Yazdanfar, S., A. M. Rollins, et al. (2003). "In vivo imaging of human retinal flow dynamics by color Doppler optical coherence tomography." *Archives of Ophthalmoloqy* 121(2): 235-239.

Yazdanfar, S., C. H. Yang, et al. (2005). "Frequency estimation precision in Doppler optical coherence tomography using the Cramer-Rao lower bound." *Optics Express* 13(2): 410-416.

Yun, S. H., C. Boudoux, et al. (2004). "Extended-cavity semiconductor wavelength- swept laser for biomedical imaging." *Ieee Photonics Technology Letters* 16(1): 293-295.

Yun, S. H., C. Boudoux, et al. (2003). "High-speed wavelength-swept semiconductor laser with a polygon-scanner-based wavelength filter." *Optics Letters* 28(20): 1981-1983.

Yun, S. H., G. J. Tearney, et al. (2004). "Pulsed-source and swept-source spectral- domain optical coherence tomography with reduced motion artifacts." *Optics Express* 12(23): 5614-5624.

Yun, S. H., G. J. Tearney, et al. (2004). "Removing the depth-degeneracy in optical frequency domain imaging with frequency shifting." *Optics Express* 12(20): 4822-4828.

Yun, S. H., G. J. Tearney, et al. (2004). "Motion artifacts in optical coherence tomography with frequency-domain ranging." *Optics Express* 12(13): 2977-2998.

Zhang, J., J. S. Nelson, et al. (2005). "Removal of a mirror image and enhancement of the signal-to-noise ratio in Fourier-domain optical coherence tomography using an electro-optic phase modulator." *Optics Letters* 30(2): 147-149.

Zhang, Y., M. Sato, et al. (2001). "Numerical investigations of optimal synthesis of several low coherence sources for resolution improvement." *Optics Communications* 192(3-6): 183-192.

Zhang, Y., M. Sato, et al. (2001). "Resolution improvement in optical coherence tomography by optimal synthesis of light-emitting diodes." *Optics Letters* 26(4): 205-207.

Zhao, Y., Z. Chen, et al. (2002). "Real-time phase-resolved functional optical coherence tomography by use of optical Hilbert transformation." *Optics Letters* 27(2): 98-100.

Zhao, Y. H., Z. P. Chen, et al. (2000). "Doppler standard deviation imaging for clinical monitoring of in vivo human skin blood flow." *Optics Letters* 25(18): 1358-1360.

Zhao, Y. H., Z. P. Chen, et al. (2000). "Phase-resolved optical coherence tomography and optical Doppler tomography for imaging blood flow in human skin with fast scanning speed and high velocity sensitivity." *Optics Letters* 25(2): 114-116.

Zhou, D., P. R. Prucnal, et al. (1998). "A widely tunable narrow linewidth semiconductor fiber ring laser." *IEEE Photonics Technology Letters* 10(6): 781-783.

Zuluaga, A. F. and R. Richards-Kortum (1999). "Spatially resolved spectral interferometry for determination of subsurface structure." *Optics Letters* 24(8): 519-521.

Zvyagin, A. V., J. B. FitzGerald, et al. (2000). "Real-time detection technique for Doppler optical coherence tomography." *Optics Letters* 25(22): 1645-1647.

Marc Nikles et al., "Brillouin gain spectrum characterization in single-mode optical fibers", *Journal of Lightwave Technology* 1997, 15 (10): 1842-1851.

Tsuyoshi Sonehara et al., "Forced Brillouin Spectroscopy Using Frequency-Tunable Continuous-Wave Lasers", *Physical Review Letters* 1995, 75 (23): 4234-4237.

Hajime Tanaka et al., "New Method of Superheterodyne Light Beating Spectroscopy for Brillouin-Scattering Using Frequency-Tunable Lasers", *Physical Review Letters* 1995, 74 (9): 1609-1612.

Webb RH et al. "Confocal Scanning Laser Ophthalmoscope", *Applied Optics* 1987, 26 (8): 1492-1499.

Andreas Zumbusch et al. "Three-dimensional vibrational imaging by coherent anti-Stokes Raman scattering", *Physical Review Letters* 1999, 82 (20): 4142-4145.

Katrin Kneipp et al., "Single molecule detection using surface-enhanced Raman scattering (SERS)", *Physical Review Letters* 1997, 78 (9): 1667-1670.

K.J. Koski et al., "Brillouin imaging" *Applied Physics Letters* 87, 2005.

International Written Opinion for International Patent application No. PCT/US2005/043951.

Erdelyi et al. "Generation of diffraction-free beams for applications in optical microlithography", J. Vac. Sci. Technol. B 15 (12), Mar./Apr. 1997, pp. 287-292.

Internation Search Report for Internation Patent application No. PCT/US2005/023664.

International Written Opinion for International Patent application No. PCT/US2005/023664.

Tearney et al., "Spectrally encoded miniature endoscopy" Optical Society of America; Optical Letters vol. 27, No. 6, Mar. 15, 2002; pp. 412-414.

Yelin et al., "Double-clad Fiber for Endoscopy" Optical Society of America; Optical Letters vol. 29, No. 20, Oct. 16, 2005; pp. 2408-2410.

International Search Report for International Patent application No. PCT/US2001/049704.

International Search Report for International Patent application No. PCT/US2004/039454.

International Written Opinion for International Patent application No. PCT/US2004/039454.

PCT International Preliminary Report on Patentability for International Application No. PCT/US2004/038404 dated Jun. 2, 2006.

Notice of Reasons for Rejection and English translation for Japanese Patent Application No. 2002-538830.

* cited by examiner

OPTICAL METHODS FOR TISSUE ANALYSIS

CROSS-REFERENCE TO RELATED APPLICATION

This application claims benefit of priority from U.S. Provisional Patent Application Ser. No. 60/244,255, filed on Oct. 30, 2000, which is incorporated herein by reference in its entirety.

TECHNICAL FIELD

The invention relates to tissue analysis, and more particularly to characterizing tissue by analyzing speckle patterns formed by light reflected from tissue.

BACKGROUND

"Speckle" is an interference phenomenon that occurs when coherent light (e.g., laser light) is reflected from a rough or multiply scattering sample onto a detection plane. Due to scattering of photons from and within the sample, different photons travel different distances to the detection plane. As a result, the light reflected or backscattered from the sample, if spatially and temporally coherent, interferes at the detection plane, producing a grainy pattern known as "speckle."

Researchers have used speckle pattern analysis to study dynamic movement of tissue in vivo. For example, speckle has been used to measure vibrations of tissue, V. Tuchin et al., "Speckle interferometry in the measurements of biotissues vibrations," *SPIE*, 1647: 125 (1992), and to measure strain in vascular and cortical tissue in response to forced movement of the tissue, Sean J. Kirpatrick et al., "Laser Speckle Microstrain Measurement in Vascular Tissue," *SPIE*, 3598: 121–128 (1999); and Sean J. Kirkpatrick and Brent W. Brooks, "Micromechanical Behavior of Cortical Bone as Inferred from Laser Speckle Data," *J. Biomedical Materials Research*, 39(3): 373–79 (1998). Researchers have also used speckle to study blood flow and lymph flow. B. Ruth, "Blood Flow Determination by the Laser Speckle Method," *Int'l J. Microcirc: Clinical and Experimental*, 9(1): 21–45 (1990); and A. A. Bednov et al., "Investigation of Statistical Properties of Lymph Flow Dynamics Using Speckle-Microscopy," *SPIE*, 2981: 181–90 (1997).

SUMMARY

The invention is based on the discovery that tissues can be analyzed in vivo using laser speckle to measure microscopic motion, e.g., Brownian motion, of structures and characteristics within the tissue.

In general, the invention features a method of analyzing tissue, e.g., in vivo, by illuminating a tissue with coherent light, such as laser light, or partially coherent light; receiving light reflected from the tissue at a detector to form a series of speckle patterns; and analyzing changes in the speckle patterns at time intervals sufficient to measure changes caused by motion of objects within the tissue on a microscopic scale, e.g., less than about 1 mm (e.g., less than about 500 or 100 microns), such as Brownian motion of molecules or macromolecules, or motion of cells or cellular organelles, or other non-random forms of motion such as lymph or intracellular transmembrane flow, while eliminating motion on a macroscopic scale, e.g., greater than about 1 mm.

For example, the speckle patterns can be measured at a near field or at a far field and imaged onto the detector. "Near field" is measurement of the speckle distribution less than one wavelength of light from the surface of a tissue, while "far field" speckle is the interference pattern formed greater than one wavelength of light from the surface. The method can further include compensating for macroscopic or extrinsic motion, such as a heartbeat, patient motion, or peristalsis, to isolate the microscopic, e.g., Brownian, motion.

In this method, the illuminating step can include providing an invasive device coupled to a light source, passing the device into a patient, placing the device in proximity to the tissue, and shining coherent light or partially coherent light from the light source onto the tissue.

The invasive device can be, e.g., a catheter, an endoscope, or a laparoscope. The device can be placed in direct contact with the tissue (to measure a near field speckle pattern) or may be a given distance from the tissue (to measure a far field or near field speckle pattern). The device can include a catheter having a first fiber (or fiber array or bundle) that transmits light from the light source to the tissue, and a fiber array or single fiber that receives light remitted from the tissue. The fiber arrays can be one or two-dimensional. The analyzing step can include comparing each of the series of speckle patterns to a series of reference speckle patterns, and quantifying the temporal correlation differences between the patterns and the reference patterns. For example, the analyzing step can include digitizing each of the speckle patterns as a function of time and space, and the quantifying step can include evaluating a cross-correlation between the patterns and the reference patterns. The analyzing step can further include determining a decorrelation rate for the speckle patterns, or analyzing spatial characteristics of the speckle pattern to deduce structural and/or biomechanical characteristics of the tissue. Biomechanical characteristics can include, for example, compliance, elasticity, stress, strain, and viscosity. In these methods, speckle pattern data is a snapshot taken at a specific point in time. Speckle pattern correlation data is a measurement of cross-correlation of the speckle pattern as a function of time.

In variations, the method can include illuminating multiple locations of the tissue in succession, forming a separate series of speckle patterns for each respective location of the tissue, and then analyzing each separate series of speckle patterns and comparing the separate series to deduce structural and/or biomechanical differences between the respective locations of the tissue.

In certain embodiments, the method includes gathering reflected light at a light receptor and transmitting the gathered light to the detector, and compensating for macroscopic motion by coupling the receptor to the tissue. Compensating for macroscopic motion can also be done by excluding changes in the speckle patterns caused by non-random motion during the analysis step. Macroscopic or extrinsic motion can also result, for example, from blood flowing between the tissue and the reflector. In those cases, the compensating step can include replacing the blood with a transparent solution and/or eliminating correlated speckle pattern information corresponding to directional blood flow.

In another embodiment, the invention features a method of analyzing a tissue structure, e.g., for determining the susceptibility to rupture of an atherosclerotic plaque having a lipid pool and a fibrous cap. The method includes illuminating the tissue structure, e.g., plaque, with coherent or partially coherent light; receiving light reflected from the tissue structure at a detector to form a series of speckle patterns; gathering speckle pattern data at time intervals sufficient to measure microscopic motion, e.g., Brownian motion or other forms of microscopic motion, within the tissue structure or tissue adjacent the tissue structure, such as a lipid pool; and assessing the tissue structure, e.g., assessing a plaque's vulnerability to rupture from the amount of Brownian motion.

The method can further include analyzing spatial characteristics of the speckle pattern data to determine structural and/or biomechanical characteristics of the tissue structure, e.g., plaque, for example, by assessing the thickness of the tissue structure, e.g., fibrous cap. The thickness of the tissue can be determined by measuring the spatial and temporal decorrelation of the speckle pattern as a function of distance from the incident beam entry point. Near the beam entry point, the speckle pattern will be more stationary. Far away from the bean entry point, the speckle pattern will decorrelate more rapidly. The location of the transition is an indication of thickness. Other methods for determining thickness are described herein. A plaque is considered vulnerable to rupture if the thickness of the fibrous cap is less than about 60 microns. The method can also be used to assess the viscosity of the lipid pool, wherein the plaque is considered vulnerable to rupture if the viscosity of the lipid pool has a time constant of less than about 200 milliseconds, and considered likely to rupture if the viscosity of the lipid pool has a time constant of less than about 100 milliseconds.

The invention also includes a method of detecting a vulnerable atherosclerotic plaque having a lipid pool and a fibrous cap within a blood vessel by illuminating a segment of the blood vessel in vivo with coherent or partially coherent light; receiving light reflected from the interior vessel wall of the segment at a detector to form a series of speckle patterns; gathering speckle pattern data at time intervals sufficient to measure microscopic, e.g., Brownian, motion within the interior vessel wall; and comparing the speckle pattern correlation data to a known speckle pattern time correlation data. One means for comparing the measured speckle pattern correlation data with a reference speckle pattern correlation data is by the time constant, or the time it takes for the speckle pattern to decorrelate by 1/e. For example, the decorrelation time constant for any given segment of vessel may be measured and compared to known time constants for normal vessels, atherosclerotic vessels, lipid pools with thick fibrous caps and lipid pools with thin fibrous caps (vulnerable plaques). If the time constant indicates the presence of a lipid pool ($\tau$<100 ms), with a thin fibrous cap, spatial characteristics of the speckle pattern data can be further analyzed to determine structural characteristics of the plaque as described herein. In addition, the first (mean) and second (standard deviation) of the probability distribution function pattern (histogram) of the speckle pattern is unique for different plaque types.

In another aspect, the invention features a fiber optic probe for detecting speckle patterns in a sample. The probe includes a catheter including a rotatable inner shaft and a transparent outer sheath; a fiber array or single fiber housed within the shaft and comprising one or more first optical fibers for transmitting incident light to the sample, and one or more second optical fibers for transmitting light remitted from the sample; and a mirror arranged near a distal end of the shaft to reflect light passing through the fiber array onto a sample outside the transparent outer sheath and back from the sample through the fiber array. The fiber array can include one (or several) incident light transmitting fiber, one (or more) remitted light transmitting fiber, and the incident light transmitting fiber can be selected from the array, and thereafter a different fiber can be selected, e.g., in series, to scan the incident light across the sample without moving the probe.

The beam emanating from the one or more first optical fibers can be focused onto the tissue by a lens, and the speckle pattern can be imaged onto the detection fiber array or onto a single detection fiber by a lens. In some embodiments, the shaft can rotate 360 degrees within the sheath, and an inflatable balloon can be connected to the sheath.

The invention further includes an optical system for detecting speckle patterns in a sample. The system has a fiber optic probe as described herein; a coherent or partially coherent light source connected to the central optical fiber within the fiber array; a detector to receive light remitted from the sample; and a processor to process the remitted light and to analyze speckle patterns remitted from the sample. For example, the processor can include reference speckle pattern time constants or a whole library of reference speckle pattern time constants, or reference speckle pattern correlation curves, e.g., for healthy and diseased tissue. The system can also include an analog-digital converter to convert the analog remitted light into a digital signal.

As used herein, "tissue" means any biological structure in or on a body. Tissue includes aggregates of cells, growths, and deposits such as plaque that may contain lipids or other components. Specific components of plaques that can be investigated include lipid pools, calcifications, fibrous regions, and fibrous caps.

"Speckle" is an interference phenomenon that occurs when coherent or partially coherent light is reflected from a rough or multiply scattering sample onto a detection plane. A "speckle pattern" is the intensity pattern that results from interference.

"Brownian motion" is the random motion of cells, molecules, and other subcomponents within tissue.

"Coherence" is the property of light that allows interference of two or more optical waves. "Partial coherence" refers to waves that can interfere with each other if the path traveled by each wave is equivalent to or within the temporal coherence length of the light at any given point in the specimen.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and are not intended to be limiting.

Other features and advantages of the invention will be apparent from the following detailed description and from the claims.

DETAILED DESCRIPTION

Figure 1:
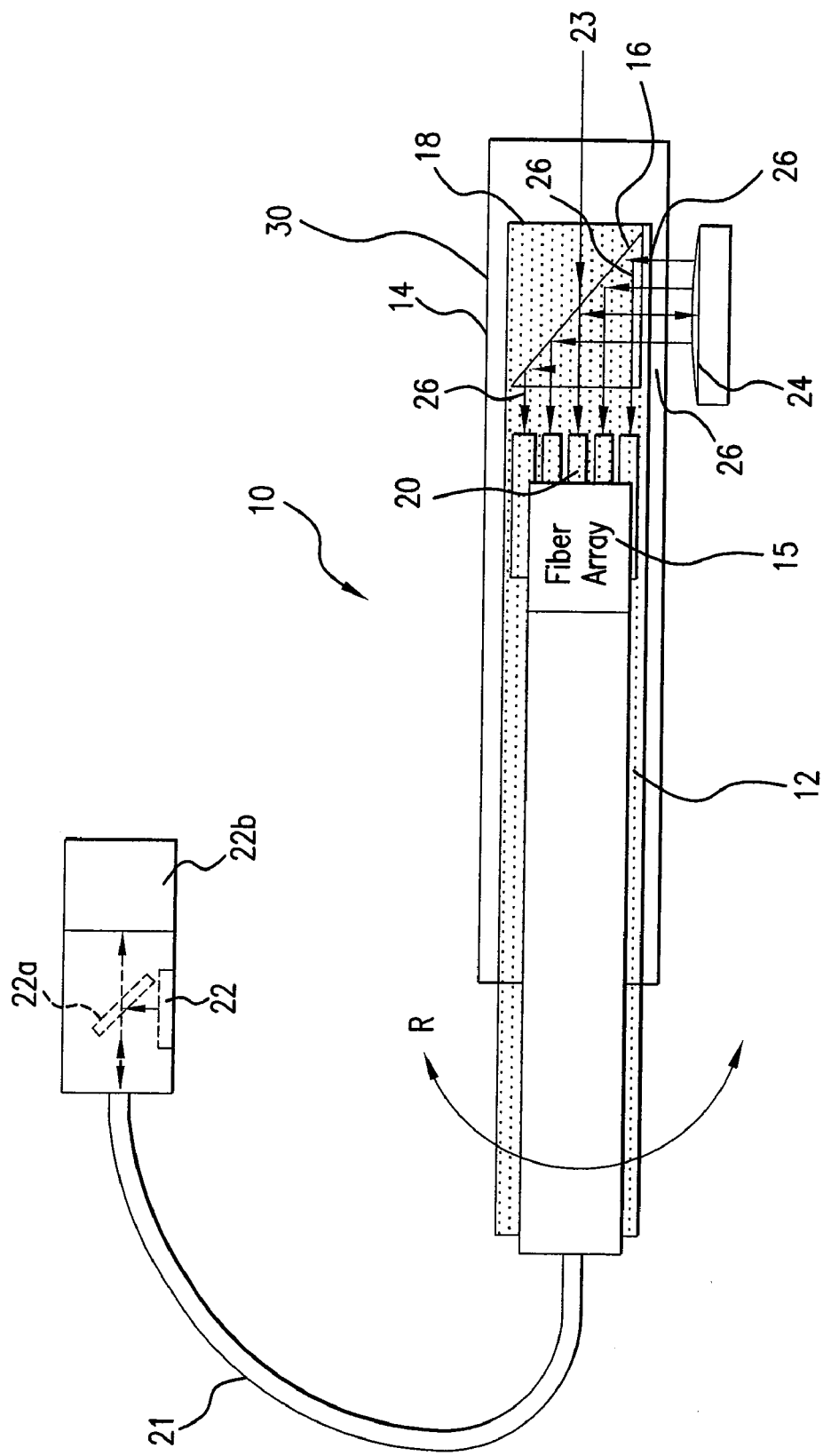
FIG. 1 is a cross-sectional schematic of an optical catheter for gathering speckle data from tissue in vivo.

At a microscopic level, most tissue is not static. Individual cells move within intercellular fluids, cellular organelles move within cells, and large molecules move back and forth between cells. In non-cellular tissue deposits such as plaques, components such as proteins, lipids, and other molecules also exhibit local motion. These local microscopic motions include "Brownian motion" and are essentially random in nature. Measuring and characterizing the microscopic motion of tissues can provide useful information about the structure, composition, biomechanical characteristics, and stability of the tissue.

The invention relates to using laser speckle to measure microscopic motion, including Brownian motion, of tissue in vivo to gather information about the tissue. In general, coherent or partially coherent light is reflected from a tissue to form a speckle pattern at a detector. Due to motion of reflectors within the tissue, the speckle pattern changes over time or is "decorrelated." By monitoring the rate of decorrelation, while compensating for "extrinsic," macroscopic motion of the tissue, microscopic motion in the tissue can be isolated and measured. The partially coherent light can provide more information about optical properties of the tissue than completely coherent light.

In some embodiments of the invention, speckle analysis is used to measure microscopic, e.g., Brownian, motion in atherosclerotic plaques to detect plaques that are vulnerable to rupture, and, more specifically, to determine the plaque's vulnerability to rupture. In these embodiments, a modified optical catheter (probe) or other instrument is inserted into a blood vessel (e.g., artery) to locate these plaques, and once a plaque is located, the probe is moved into the proximity of the specific atherosclerotic plaque. Light reflected from the interior wall of the blood vessels, and/or from a plaque, is collected and transmitted to a detector, where a speckle pattern is formed. The speckle patterns of normal tissue and plaque tissue (especially vulnerable plaque tissue) are different, and these differences can be used to detect the plaques. Thereafter, e.g., while compensating for macroscopic motion of the plaque, the speckle pattern is monitored over time to calculate the pattern's rate of decorrelation. From this decorrelation rate, the degree of microscopic motion in the plaque, and therefore the plaque's vulnerability to rupture, can be assessed.

I. Atherosclerotic Plaques

Rupture of an atherosclerotic plaque can lead to acute myocardial infarction, which is a leading cause of death in industrialized countries. When an atherosclerotic plaque ruptures, lipids from the plaque enter the vessel lumen, potentially causing thrombosis, arterial occlusion, myocardial ischemia, and infarction.

According to recent research, plaques vulnerable to rupture generally have a thin, unstable, fibrous cap and a compliant, or less "viscous," lipid pool. See, e.g., Virmani et al., "Lesions from sudden coronary death: A comprehensive morphological classification scheme for atherosclerotic lesions," Arterioscler. Thromb. Vasc. Bio., 20:1262–75 (2000) and Lee et al., "The Unstable Atheroma," Arteriosclerosis, Thrombosis & Vascular Biology, 17:1859–67 (1997). The less viscous lipid pool applies force to the fibrous cap, compromising the cap and causing rupture. The greater the Brownian motion in the lipid pool, the lower the "viscosity" of the pool, and the more likely the plaque will rupture. Assessing Brownian motion in the lipid pool and measuring the thickness of the fibrous cap in vivo, therefore, helps to identify plaques likely to rupture, allowing intervention.

II. Speckle Image Formation

Referring to FIG. 1, a specially modified optical catheter 10 includes a rotatable inner shaft 12 and a transparent outer sheath 14. The inner shaft 12 houses a fiber array 15 and a mirror 16 near its distal end 18. A central fiber 20 in the fiber array connects to a fixed optical fiber 21 that extends from the catheter proximally to a light source 22.

In operation, coherent light, such as laser light, from light source 22 is transmitted via beam-splitter 22a, through the fixed optical fiber 21 and central fiber 20 and onto center 23 of mirror 16. From mirror 16, the light is reflected to a tissue sample 24, such as a layer of static tissue over a layer of moving tissue, such as an atherosclerotic plaque. Outer sheath 14 can be placed directly in contact with sample 24 (near field), or can be positioned a short distance, e.g., 1 mm to 10 cm away from the sample (far field). Light enters sample 24, where it is reflected by molecules, cellular debris, proteins, compounds (e.g., cholesterol crystals), and cellular microstructures (such as organelles, microtubules) within the sample. Light remitted from the sample (arrows 26) reflects from mirror 16 to the fibers of array 15, and is then transmitted by array 15 to a planar charge-coupled device (CCD), or a linear or two-dimensional detector 22b, via a beam-splitter 22a, e.g., located within light source 22. There may be one or multiple fibers for detection and illumination and detection may occur from the same fiber. Alternatively, illumination may occur through a fiber array where each fiber is selectively illuminated to generate multiple speckle patterns as a function of position on the sample. This method can provide a scanning of the incident light across a sample while keeping the probe stationary by illuminating one fiber after another in series.

Due to interference, a speckle pattern forms at the CCD detector. The resulting speckle pattern is then digitized by an analog-digital converter, and analyzed using the procedures described in the analysis section below.

The entire shaft 12 can rotate 360 degrees in the direction of arrow R, allowing catheter 10 to gather images around the entire circumference of a sample. For example, catheter 10 can gather images of a plaque around the circumference of a vessel wall.

Since only a few fibers are required to gather adequate speckle data, the diameter of the catheter can be less than 500 μm. Larger diameters are also possible.

Many other types of instruments can be used to gather speckle data. For example, the optics of catheter 10 can be integrated into other types of instruments, such as endoscopes or laparoscopes. The optics can also form a standalone unit passed into the accessory port of standard endoscopes or laparoscopes, or integrated into another type of catheter, such as dual-purpose intravascular ultrasound catheter.

The optics can also include a lens that focuses the remitted light 26 onto the distal ends of the fibers in array 15. The lens would allow formation of a "near field image" (near the sample sight less than one wavelength) rather than a "far field image" (at the detector set more than a wavelength away from the surface of the tissue).

The catheter can include a polarization filter to remove all but a certain type of polarized light. For example, a cross-polarized filter would allow only light having a polarization perpendicular to the incident light to reach the detector, while a parallel polarized filter would allow only light having the same polarization as the incident light to pass. Since multiply scattered light is less likely to retain its initial polarization than single scattered light, polarization filters can be used to bias the data toward multiply scattered or single scattered light. Such bias can be used to deduce information about the structure of the sample, since light which has penetrated deeper into the sample will be more highly scattered than light reflected from the surface or remitted from near the surface.

Instead of a CCD, the detector can be, e.g., a photographic plate, an array of photodetectors, or a single detector. The light source can illuminate the sample with continuous light or synchronized pulses.

Rather than transmitting the light to the sample through optical fibers, it is also possible to shine light onto a sample in free space. For example, in an open surgical procedure, coherent light in free space could be directed onto a sample with mirrors, and the remitted light then directed to a fiber array. In such free space embodiments, the light source can be, e.g., as far as one meter, or more, away from the sample.

III. Isolation of Microscopic Motion

To simplify determining the viscosity of a moving tissue or liquid (e.g., a plaque's lipid pool) under a static tissue (e.g., a plaque cap) from changes in a speckle pattern, the temporal changes in the pattern should indicate movement of reflectors within the plaque, but not indicate movement of the plaque itself or movement of reflectors between the detector and the plaque. In other words, the changes in the plaque's speckle pattern preferably reflect microscopic or Brownian motion, but not macroscopic motion.

To isolate microscopic motion, data is gathered: (1) at time intervals sufficient to detect microscopic motion; and (2) in a manner that compensates for macroscopic (e.g., extrinsic) motion.

For a time interval to be sufficient to detect microscopic Brownian motion, the interval must be long enough to allow for movement of reflectors in the tissue, such as a lipid pool, but short enough that the random Brownian movements do not cancel out. For atherosclerotic plaque, an appropriate time interval is about 1–200 ms. Shorter time periods may also be possible. If the time intervals are longer, then changes in the speckle pattern may not adequately differentiate rapid Brownian movement (indicating low viscosity) from slower Brownian movement (indicating high viscosity).

In the atherosclerotic plaque and other examples, two common sources of macroscopic motion are gross movement of the vessel lumen and plaque tissue due to heartbeats, and blood flow between the plaque and the catheter. Patient movement can also be an issue.

Figure 2A:
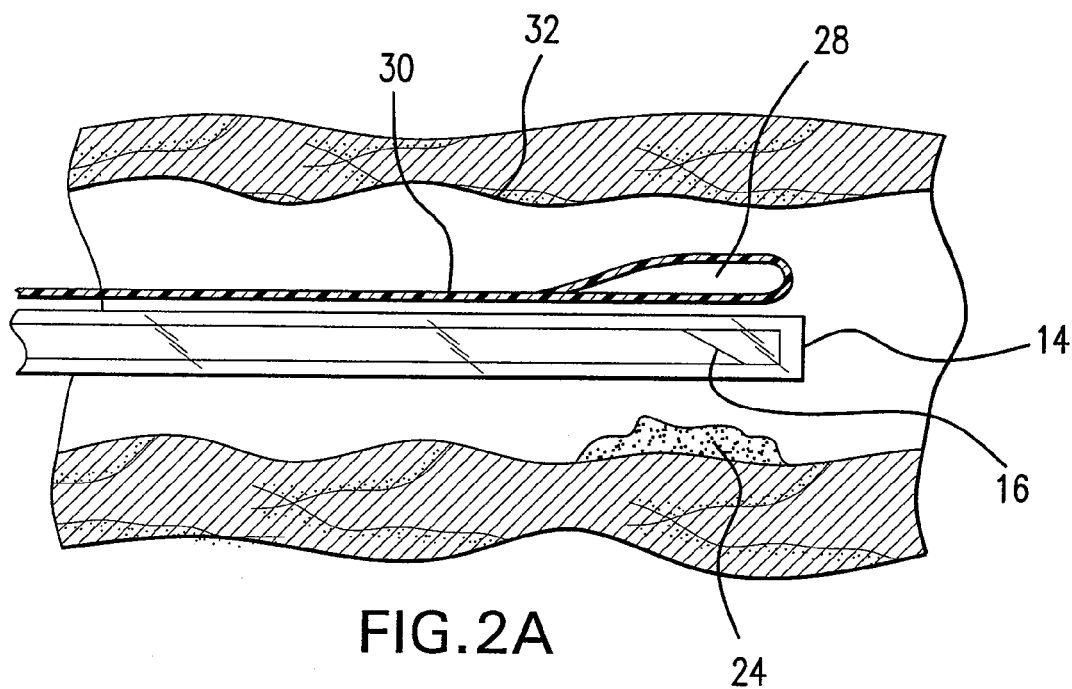
FIG. 2A is a cross-sectional schematic illustrating the catheter of FIG. 1, with an attached angioplasty balloon, inserted within a blood vessel, with the balloon deflated.
Figure 2B:
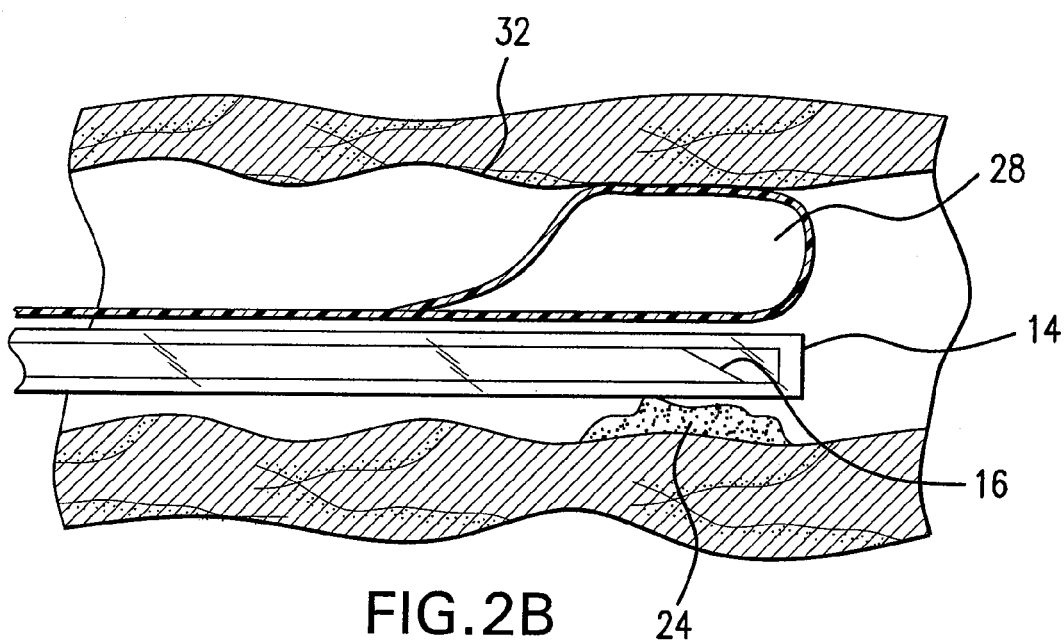
FIG. 2B is a cross-sectional schematic illustrating the catheter of FIG. 1, with an attached angioplasty balloon, inserted within a blood vessel, with the balloon inflated.

To compensate for gross motion of a target tissue (e.g., a plaque) due to heartbeats, at least two alternatives are possible. First, the fiber array 15 can be coupled to the plaque tissue using, e.g., an angioplasty balloon. This technique also compensates for minor patient movements. Referring to FIG. 2A, in one embodiment, a balloon 28 is attached to outer sheath 14, on a far side 30 of the catheter. Once the catheter is positioned within a blood vessel in proximity to the plaque, the balloon is inflated. Referring to FIG. 2B, the inflated balloon abuts the vessel wall 32, and presses the catheter against plaque 24, such that a distal region of outer shaft 14 is in direct contact with the plaque. With the catheter coupled to plaque 24 as shown in FIG. 2B, fiber array 15 will move with the plaque when the heart beats, and the gross motion of the plaque will not significantly affect the speckle pattern.

Other methods of coupling the catheter to the plaque are also possible. For example, instead of placing the balloon to the side of the catheter, the balloon can surround the catheter. In this arrangement, a transparent balloon surrounds outer sheath 14, but is also attached to the sheath. When the balloon is inflated, the balloon is squeezed between plaque 24 and wall 32 of the vessel. The balloon, therefore will be in direct contact with the plaque, and will move with the plaque when the heart beats. Since the balloon is attached to shaft 14, and shaft 14 is coupled to array 15, movement of the vessel wall will not significantly affect the speckle pattern. Additional methods of coupling the catheter to tissue can also be used, including methods that do not employ an angioplasty balloon.

A second method of compensating for movement caused by heartbeats is to gather data between heartbeats. In this method, data is gathered during the relatively still PR interval of the diastole of the heartbeat (when the left ventricle is filling with blood). The PR interval lasts for about 0.12–0.2 seconds, providing sufficient time to detect Brownian motion. To insure that data is gathered during diastole, the timing can be computer-controlled or the detector can be linked to an ECG signal, and programmed to gather data only during the PR interval. Similar techniques can be used to compensate for other bodily movements such as peristalsis.

To compensate for blood flow between the catheter and the plaque, the catheter can be placed in direct contact with the plaque tissue, as described above, thereby preventing blood from flowing between the detector and the plaque. Alternatively, blood flowing between the plaque and the catheter can be removed and replaced with clear saline solution or other clear solutions such as optically transparent blood substitutes.

Finally, rather than compensating for macroscopic motion while gathering data, one can compensate for this motion during the analysis phase by mathematically excluding the macroscopic (extrinsic) motion from the analysis, as described below.

IV. Analysis of Speckle Data

Figure 3:
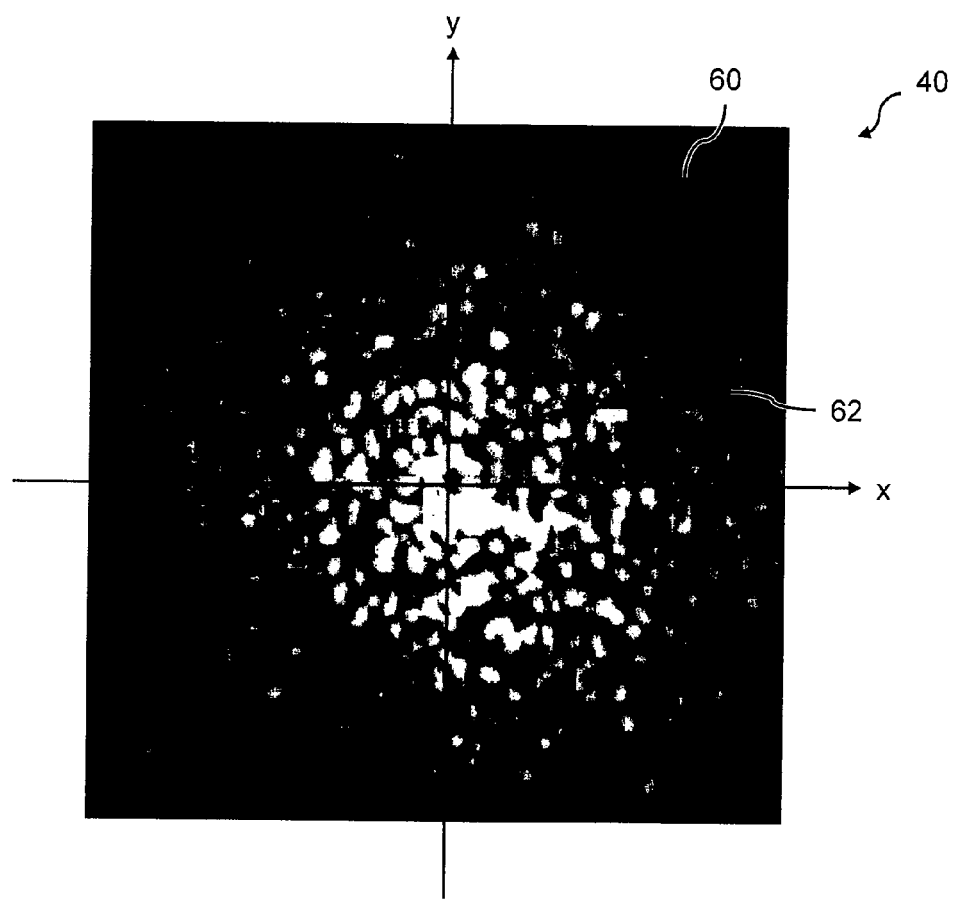
FIG. 3 is a speckle pattern produced from a cadaveric human aorta using incident light of $\lambda=632.8$ nm.

FIG. 3 illustrates a typical speckle pattern 40 formed by reflecting light from the wall of a healthy blood vessel. X and Y coordinates overlay pattern 40 to facilitate mathematical description of the pattern. The pattern includes dark patches, where destructive interference dominates, and brighter patches, where constructive interference dominates. Very subtle movements of reflectors within the multiply scattering sample alter the speckle pattern.

By analyzing a series of speckle patterns formed from light reflected from a plaque, one can estimate: (a) the viscosity of a plaque's lipid pool; and (b) the thickness of plaque's fibrous cap. From either or both of these types of data, the plaque's vulnerability to rupture can be assessed.

A. Determining Viscosity of a Plaque's Lipid Pool

There are a number of methods of analyzing speckle data to determine the viscosity of a plaque's lipid pool. By way of example, one method is described in detail in this section and in the Example section below. This method includes: (1) gathering a series of speckle images at short, discrete time intervals; (2) eliminating diffuse reflectance from the data; (3) creating cross-correlation images comparing the speckle images in the series; (4) calculating the maximum correlation between each pair of images to create a one-dimensional data set over time; (5) calculating the rate of decorrelation from the data set; and (6) from the rate of decorrelation, assessing the plaque's viscosity and vulnerability to rupture.

First, using the detection system described above, a series of speckle images are gathered for a plaque at discrete intervals over a period of time. For example, speckle images can be gathered, e.g., at intervals of every 1, 5, 10, 20, or 30 ms for a time period of, e.g., 200 ms. In general, the shorter the time intervals, the shorter the time period over which data can be gathered. For longer time intervals, such as 30 ms, data can be gathered for, e.g., 1–2 seconds.

Second, to isolate the speckle pattern, the background, non-coherent diffuse reflectance is eliminated from the images. A number of techniques can be used to eliminate the tissue's diffuse reflectance. For example, the raw data speckle images can be converted to edge images. Edge images are spatial derivatives of the raw data images; an edge image (high pass filter) reflects the change in intensity of an image as a function of space, at all points in the image, rather than the intensity itself. Known techniques of edge detection include convolution of the image by a kernel (e.g., Sobel or Robert), Morph gradient (subtraction of an eroded, dilated, closed, or opened image by its original), or high pass filtering. Other methods of eliminating background diffuse reflectance include homomorphic filtering, local histogram equalization, or using an optical setup with a small aperture. All of these techniques are well known, and are described, e.g., in Gonzalez, R. C. and Wintz, P., "Digital Image Processing" (Addison-Wesley Publishing Company, Reading Mass., 1987) and Jain, Anil, K., "Fundamentals of Digital Image Processing" (Prentice Hall, Englewood Cliffs, N.J., 1987).

After eliminating the non-coherent background reflectance, each speckle image (or edge image) is compared to a reference image in the series (e.g., the t=0 image) to create a series of cross-correlation images. The cross-correlation images reflect the degree of correlation between the two images as a function of space. From each cross-correlation image, the maximum correlation peak (i.e., the amount of correlation at the point of maximum correlation) is determined using the equation:

$$g(t) = \max[\int\int I(x,y,0)I(x+x',y+y',t)dx'dy'] \quad (1)$$

where g(t) is the cross-correlation function, I(x, y) is intensity of the interference at a point (x, y) in the pattern, and t is time. Two-dimensional cross-correlation functions are described generally in Jae S. Lim, "Two-Dimensional Signal Processing" (Prentice Hall, Englewood Cliffs, N.J., 1990) and Jain, Anil, K., "Fundamentals of Digital Image Processing" (Prentice Hall, Englewood Cliffs, N.J., 1987).

By performing the maximum correlation calculations, the cross-correlation images are reduced to a one-dimensional data set as a function of time (i.e., a series of correlation values, each value associated with a time t). From this series of correlation values, a time constant, $\tau$, is calculated, where $\tau$ represents the rate of decorrelation. The time constant is the amount of time it takes g(t) to reach (1/e)g(0).

The max function of equation (1) is not the only possible mechanism for reducing the cross-correlation images to a number. For example, image comparisons can be reduced to a representative value by evaluating the cross-correlation function:

$$g(x,y,t) = \int\int I(x,y,0)I(x+x',y+y',t)dx'dy' \quad (2)$$

at a point, such as x=y=0. However, using a point to reduce the image to a value, rather than a max function, would not compensate for the "memory effect" of first order correlation of speckle patterns in turbid media. This "memory effect" is described in Feng et al., Science 251: 633–39 (1991). Advantages to using a point are that a minimum number of fibers and detectors can be used.

From the rate of decorrelation, represented by time constant $\tau$, the viscosity of the plaque's lipid pool can be assessed. In general, the larger $\tau$, the lower the Brownian motion in the lipid pool, and the greater the pool's viscosity. On the other hand, the smaller $\tau$, the greater the Brownian motion in the lipid pool, and the lower the viscosity. The lower the viscosity, the more stresses are exerted on the cap, making the plaque more vulnerable This information, the viscosity of the plaque's lipid pool, can be used to identify plaques likely or vulnerable to rupture. Specifically, if T is about 40–100 ms or lower, then the plaque is likely to rupture, and intervention is warranted. If the plaque $\tau$ is about 100–200 ms, then the plaque is somewhat vulnerable, but not yet likely to rupture, and should be monitored over time. If the plaque $\tau$ is about 200–300 ms, then the plaque is less vulnerable. Non-plaque covered, healthy vessel wall generally has a time constant greater than 300 ms or 500 ms.

B. Determining Thickness of a Tissue Structure Such as a Plaque's Fibrous Cap In addition to determining the viscosity of the lipid pool in the plaque, the speckle data can be analyzed to deduce spatial characteristics of the plaque, including the thickness of the fibrous cap, or the thickness of any tissue structure or tissue layer for that matter. As discussed above, a thin fibrous cap is another indication that a plaque is vulnerable to rupture. The combination of data relating to viscosity and cap thickness provides the most accurate assessment of plaque vulnerability, although the two characteristics can be assessed and analyzed independently.

Figure 4:
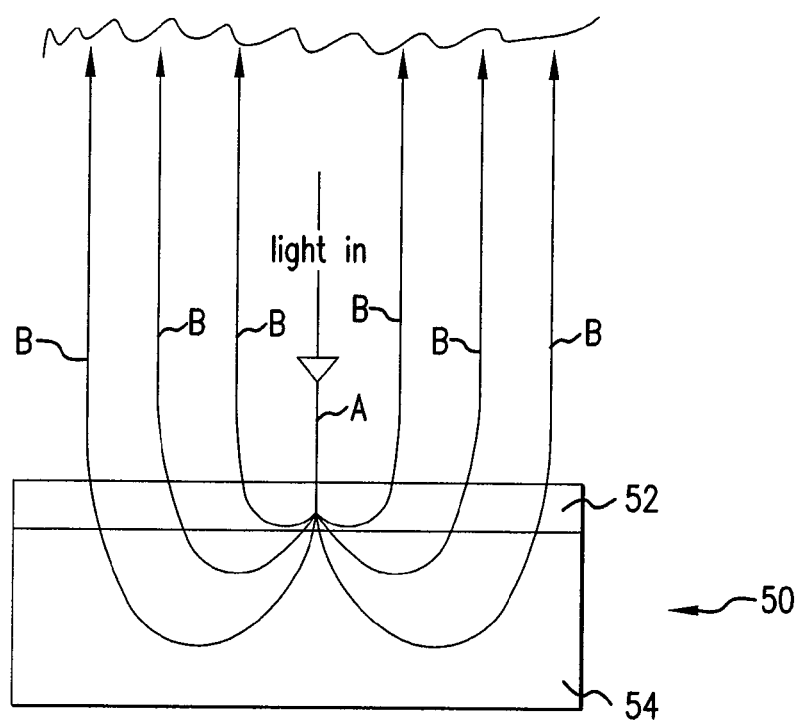
FIG. 4 is a schematic illustrating reflectance of incident light from an atherosclerotic plaque.

Referring to FIG. 4, a typical plaque 50 includes a fibrous cap 52 and a lipid pool 54. Photons that enter plaque 50 (arrow A) are internally scattered by reflectors within the plaque, such as collagen in fibrous cap 52 and lipids in pool 54. The various photons, therefore, exit the plaque at different locations (arrows B). As a result, the speckle pattern (see FIG. 2) has a diameter considerably larger than the width of the original light beam.

The thickness of fibrous cap 52 can be deduced by comparing different regions of the resulting speckle pattern. Referring again to FIG. 3, light forming intensity signals in the outer portion 60 of the pattern traveled greater distances than light forming signals near the center 62 of the pattern. Thus, outer portion 60 of the pattern is formed by photons that, on average, penetrated deeper into the plaque than photons forming center 62. By calculating separate time constants for separate regions of the speckle pattern, the viscosity of the plaque at different depths can be determined. Since the fibrous cap generally exhibits less Brownian motion than the lipid pool, the thickness of the fibrous cap can be estimated from spatially dependent data.

To estimate the thickness of the fibrous cap, separate max cross-correlation functions are described for separate, small regions of the pattern. Each region is defined by a window, w, centered at $(x_o, y_o)$:

$$g(x_o,y_o,t)=\max[\int\int w(x'-x_o,y'-y_o)\, I(x,y,0)I(x+x',y+y',t)\, dx'dy'] \quad (3)$$

Time constants are then calculated from the cross-correlation data for each window, in the manner described above. The variation of $\tau$ as a function of the distance from the center of the speckle pattern (i.e., as a function of $(x_o^2+y_o^2)^{1/2}$) can then be analyzed to determine the thickness of the fibrous cap. Plaque cap thickness of less than about 60 μm is considered to be vulnerable, but this number can vary to some extent depending on the specific patient.

In general, the thickness of any tissue structure, e.g., a tissue layer that overlies or is adjacent to a different tissue, e.g., a plaque fibrous cap over a lipid pool, can be measured using the following algorithm:

1. Measure the decorrelation time constant $\tau$ as a function of $r=(x_o^2+y_o^2)^{1/2}$ 2. Measure the optical properties (e.g., effective attenuation coefficient $\mu_{\mathit{eff}}$) of the tissue layer by computing the first and second order statistics of a speckle probability distribution function (PDF)(histogram), or by using diffuse reflectance spectrophotometry.

3. Compare $\tau(r)$ and the optical properties (e.g., $\mu_{\mathit{eff}}$) to previously computed Monte Carlo or Diffusion theory simulations of $\tau(r)$ and $\mu_{\mathit{eff}}$ as a function of tissue layer thickness. Alternatively, if $r_0$ is defined as the cutoff between static and non-stationary speckle, $r_0$ and $\mu_{\mathit{eff}}$ may be used as inputs to a look-up table containing tissue layer thickness values.

C. Mathematical Compensation for Macroscopic Motion

In addition to providing information about the structural features of a tissue such as a plaque, separately analyzing different regions of a speckle pattern also allows decorrelation caused by macroscopic motion to be identified and removed from the analysis. In general, macroscopic motion caused by gross movement of the plaque tissue or blood flow will be directional, non-random, and global. By contrast, Brownian motion will be non-directional and non-uniform (or random). Thus, by calculating separate decorrelation functions for different regions of the speckle pattern, decorrelation due to extrinsic motion can be identified and subtracted from the functions, allowing isolation of random, Brownian motion. For example, the position of maximums of cross-correlation functions will shift along a vector $\overline{v}$, which relates extrinsic motion of the sample with respect to the catheter or detection. Brownian motion will decorrelate the speckle patterns in many random directions, and will result in a broadening of the cross-correlation peak and a decrease in correlation maximum above that predicted by linear motion. These two behaviors for intrinsic and extrinsic linear motion should be separable from the cross-correlation function.

V. Additional Imaging Methods

In a simplified system, the rate of decorrelation can be estimated from single pixel speckle images, rather than full, two-dimensional speckle patterns. In this system, a catheter with a single optical fiber could transmit data to a single detector, such as a photodiode. The speckle data gathered would be intensity at the spot as a function of time. From this data, a rate of decorrelation can be calculated directly or only as a function of time as opposed to space, without any spatial cross-correlation analysis.

Imaging methods that detect single scattered light, such as optical coherence tomography (OCT) and confocal microscopy, can also be used. While these imaging methods are less sensitive to speckle modulation than the multiple scattering methods described above, they have the advantage of allowing localization of data to a single point within the sample. Such localization would allow measurement of biomechanical properties of the tissue in three dimensions. In addition, in methods that use heterodyne detection, such as OCT, motion of the scatterers can produce a Doppler shift on the returned light. The Doppler shift can provide a further basis for measuring viscosity in the sample. For Brownian motion the velocities would be distributed over a range of velocities and directions causing multiple Doppler shifts and a broadening of the frequency bandwidth distribution. The mathematics for OCT and confocal microscopy based imaging techniques would be substantially similar to the mathematics described above.

EXAMPLE

In this example, speckle images formed by reflecting laser light from a cadaveric atherosclerotic plaque in a human aorta were analyzed to assess the plaque's viscosity. A portion of normal aorta was also analyzed for comparison.

Figure 5:
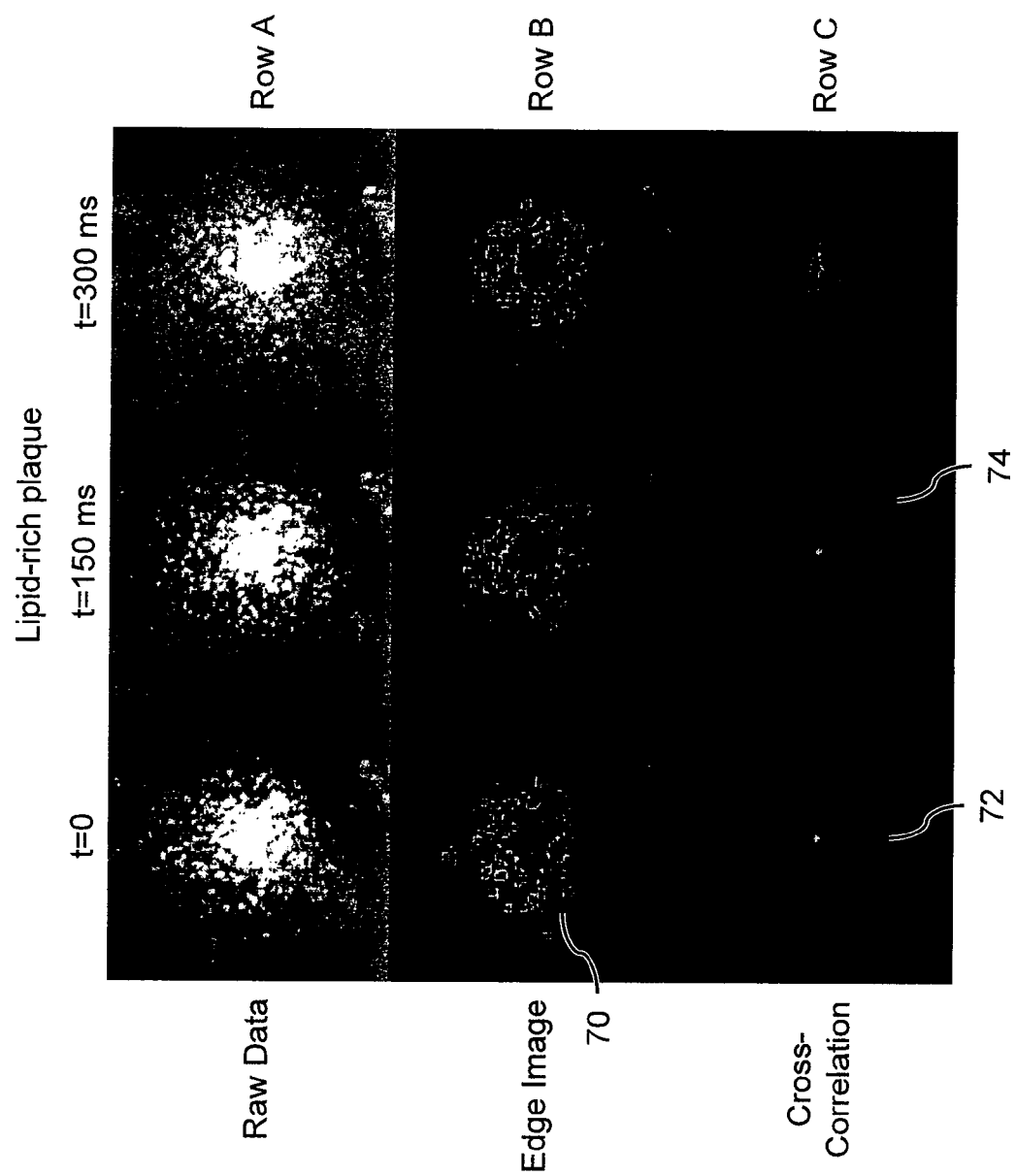
FIG. 5 is representative raw data speckle images, edge images, and cross-correlation images used to assess the viscosity of a lipid-rich, atherosclerotic plaque in a human aorta.

At a temperature of 37° C., light from a helium-neon laser ($\lambda$=632.8 nm) was shined on a cadaveric aortic plaque for two seconds. Light reflected from the plaque was received at a CCD camera with a shutter speed of 30 frames per second, through a cross-polarization filter. During the two seconds, the CCD camera recorded a series of 60 speckle images at intervals of 33 ms. Three of the 60 raw data images, corresponding to times t=0, t=150 ms, and t=300 ms, are shown in row A of FIG. 5.

Using IPLab® Spectrum® imaging software, edge detection was performed on the 60 raw speckle images, generating 60 edge images. The three edge images for times t=0, t=150 ms, and t=300 ms are shown in row B of FIG. 5. As discussed above, the edge images reflect the spatial derivative of the raw speckle images (i.e., the light patches in the edge images of row B are locations where the intensity is changing as a function of space).

Using the same software, each of the 60 edge images was then compared to the t=0 edge image 70 to form 60 cross-correlation images. Each cross-correlation image was generated by multiplying the Fourier transform of the reference image 70 by the complex conjugate of the Fourier transform of the image in question, and then calculating an inverse Fourier transform of the product. For example, referring to row C of FIG. 5, image 72 is an autocorrelation of the t=0 edge image. Image 72 was formed by multiplying the Fourier transform of reference image 70 by the complex conjugate of the Fourier transform of image 70, and then calculating the inverse Fourier transform of the product. Image 74 was formed by multiplying the Fourier transform of image 70 by the complex conjugate of the Fourier transform of the t=150 ms edge image, and then calculating the inverse Fourier transform of the product.

Each cross-correlation image represents the degree of correlation between the corresponding edge image and the reference edge image 70 (i.e., brighter spots are locations where there is a higher degree of correlation than at darker spots).

From each cross-correlation image, the maximum cross-correlation peak (i.e., the correlation at the maximum point of correlation) was calculated using equation (1). The resulting data set included 60 cross-correlation values, each value associated with a time t.

Figure 6:
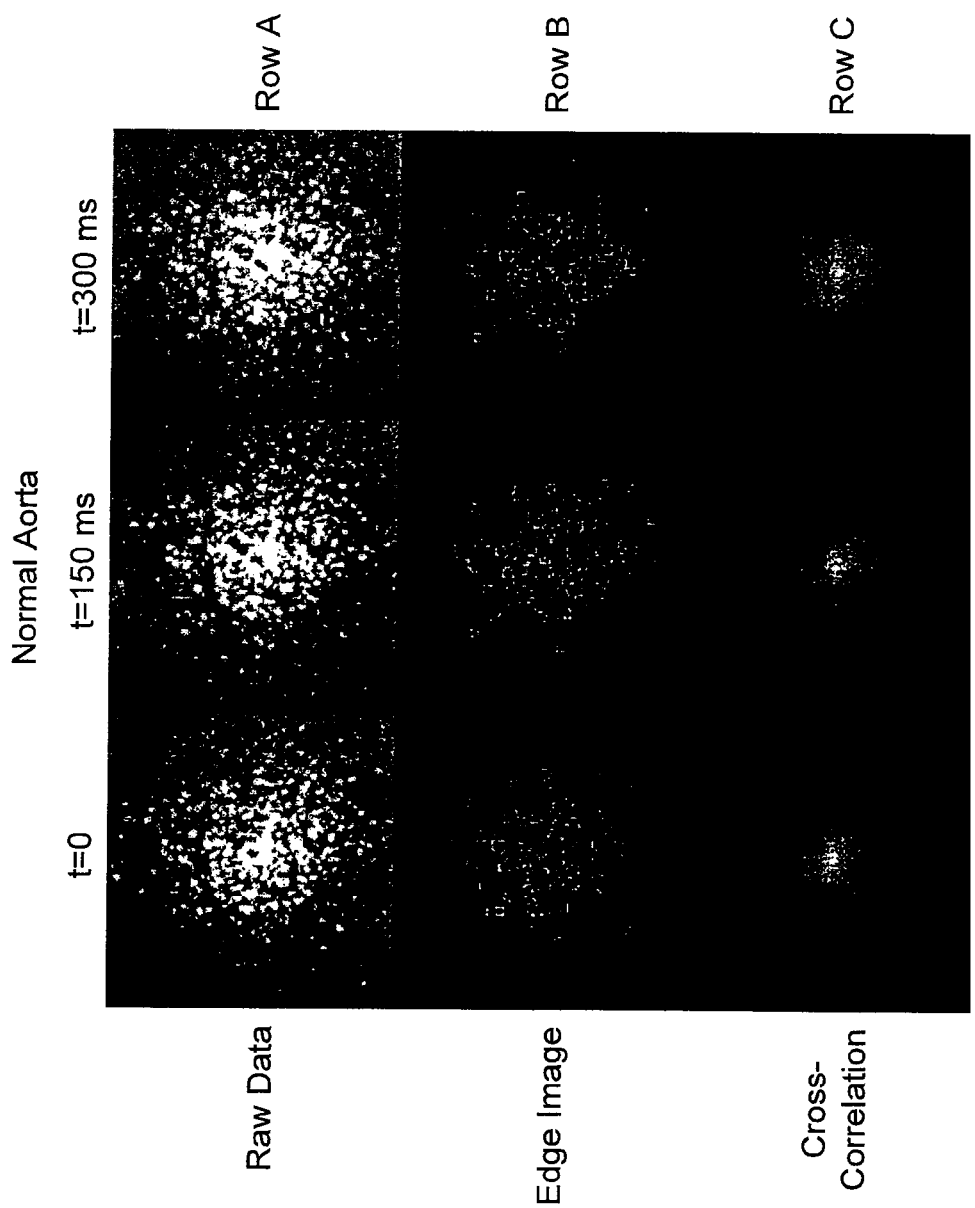
FIG. 6 is representative raw data speckle images, edge images, and cross-correlation images used to assess the viscosity of normal human aorta tissue.

A set of images of normal aorta tissue is shown in FIG. 6. These images are comparable to the set of images in FIG. 5 for a lipid-rich plaque in the same aorta and were imaged and processed in the same manner.

Figure 7:
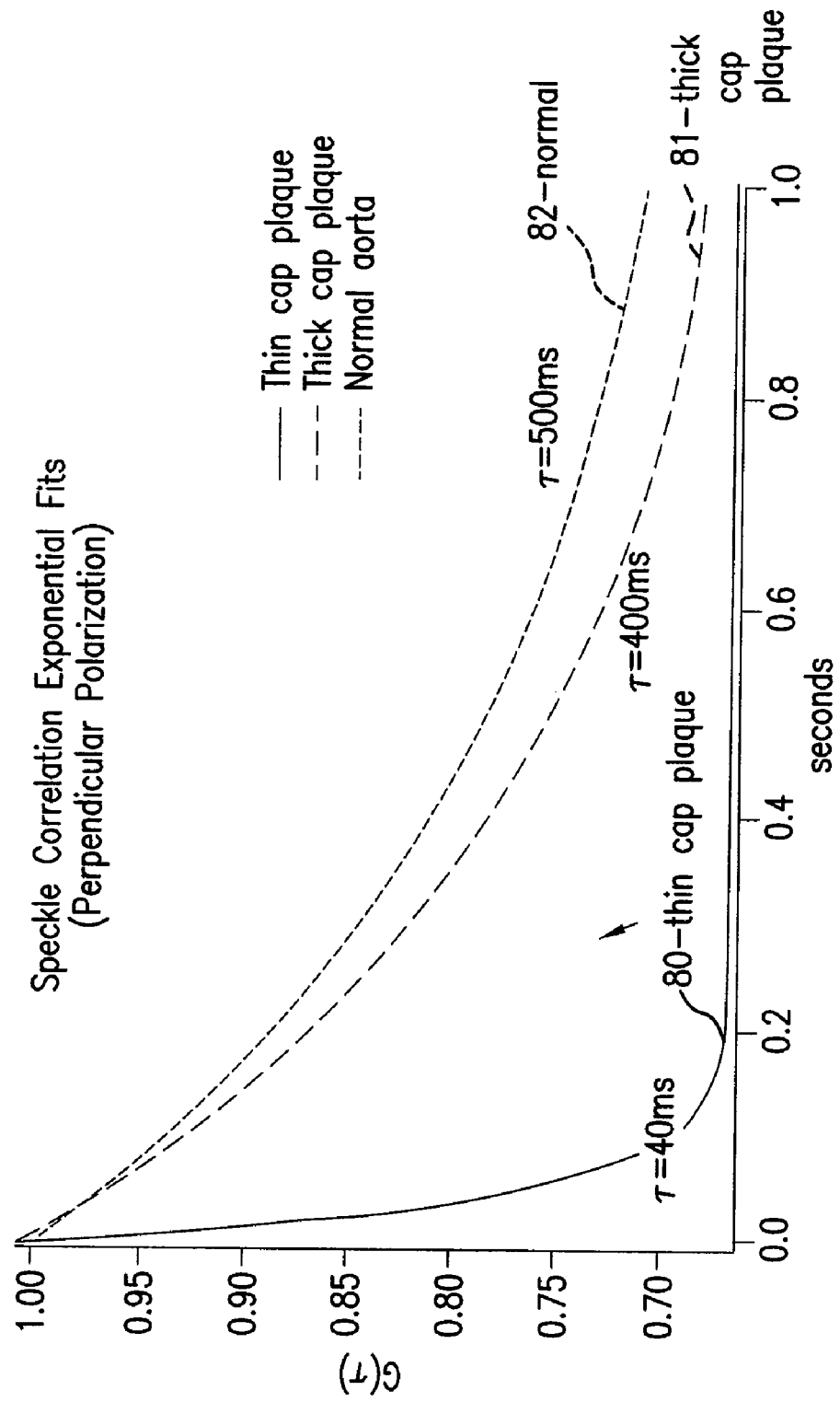
FIG. 7 is an exponential graph showing speckle decorrelation of a thin cap atherosclerotic plaque, a thick cap atherosclerotic plaque, and normal aortic tissue over a time interval.

The maximum cross-correlation data for the lipid-rich plaque and the normal aorta tissue were then fit to an exponential cross-correlation function, $G(\tau)$, using Igor Pro®, v 3.01 software (Wavemetrics, Inc). The resulting exponential function was graphed in FIG. 7, curve 80. By way of comparison, the exponential cross-correlation function for speckle data taken from healthy cadaveric aortic tissue is shown in curve 82. The data for curve 82 was gathered and processed using the same procedures as the data for curve 80. FIG. 7 also shows the data for a thick-capped plaque (curve 81). The time constant for this non-vulnerable plaque was 400 ms, so the plaque would not need intervention. Again, the same techniques were used to generate this curve as curves 80 and 82.

From the cross-correlation data, the decorrelation rate, represented by the time constant $\tau$, was calculated. For the plaque, the time constant was 40 ms. For the aortic tissue, the time constant was 500 ms.

Based on these data, the plaque was borderline vulnerable. Thus, had this plaque been analyzed in vivo, using the procedures described above, a physician would have determined that the plaque was a possible candidate for rupture, and may have chosen to intervene, preventing a possible infarction.

OTHER EMBODIMENTS

As noted throughout, the methods described herein can also be used to characterize diseased tissue other than atherosclerotic plaques. The microscopic and macroscopic constituents of diseased tissue differ from normal non-pathologic counterparts. For example, speckle patterns can be used to diagnose and characterize other tissue pathology such as neoplasia (cancer), infection, tissue viability, or healing response to injury. In the case of neoplasia, tumors typically have an abnormal abundance of one cell type (clonal) and a surrounding abnormal supporting matrix. This cell type may produce and secrete a viscous fluid, such as mucin in adenocarcinoma, which would result in lower speckle decorrelation time constants than normal non-cancerous tissue. Moreover, the surrounding matrix may be composed of necrotic tissue and an abundance of abnormal vessels that would also serve to decrease the speckle decorrelation time constant. Other tumors, like osteosarcoma, produce osteoid or immature bone that would increase the time constant compared to normal tissue. Other forms of neoplasia would have increased time constants due to desmoplastic (abundant) fibrous stroma initiated by cytokines produced by the tumor. Indeed, many tumors, including bronchogenic carcinomas and breast carcinomas are firm upon gross examination due to the fibrous stroma surrounding the malignant cells. This fibrous stroma would increase the time constant relative to surrounding normal tissue.

In other examples, in the case of infection, abscesses will be less viscous than surrounding tissue, enabling identification of the infected region by measuring a decrease in the time constant. Inflammation, manifested by the influx of activated inflammatory cells will be characterized by a decrease in the speckle decorrelation time constant as these cells degrade the normal supporting tissue in response to a the presence of bacterial, viral, or foreign body antigens. Necrotic tissue, such as burn eschar, diabetic ulcers, necrotic bowel, and ischemic myocardium will have longer time constants than viable tissue from the same organ due to the lack of intravascular and extravascular fluid and flow in these extracellular spaces.

In the case of healing, fibrosis and fibrous remodeling will likely have longer time constants due to the abundance of collagen matrix and granulation tissue, which would not be present in uninjured tissue. Speckle decorrelation times may also be used to estimate tissue hydration and provide a means for quantifying the state of hydration in a patient. While the above examples elucidate some of the mechanisms that explain how disease affects the biomechanical properties of pathologic tissue, many more exist and are well known in the field of gross anatomic pathology. These differing biomechanical properties and characteristics can be measured by speckle for the purpose of screening, intraoperative margin (e.g., tumor margin) identification, and primary diagnosis.

The foregoing detailed description is intended to illustrate and not limit the scope of the invention, which is defined by the appended claims. Other aspects, advantages, and modifications are within the scope of the claims.

What is claimed is:

1. A method of analyzing tissue, the method comprising:
   illuminating a tissue with coherent or partially coherent light;
   receiving light reflected from the tissue at a detector and forming series of speckle patterns;
   analyzing changes in the speckle patterns at time intervals sufficient to measure changes caused by microscopic motion of objects within the tissue, wherein the tissue is at least one of in vivo or an internal tissue; and
   compensating for macroscopic motion to isolate the microscopic motion.

2. The method of claim 1, wherein the microscopic motion is Brownian motion.

3. The method of claim 1, wherein the microscopic motion is motion of cells or cellular organelles.

4. The method of claim 1, wherein the illuminating step comprises providing an invasive device coupled to a light source, passing the device into a patient, placing the device in proximity to the tissue, and shining coherent or partially coherent light from the light source onto the tissue.

5. The method of claim 4, wherein the invasive device is selected from the group consisting of a catheter, an endoscope, and a laparoscope.

6. The method of claim 4, wherein the placing step includes placing the device in direct contact with the tissue.

7. The method of claim 1, wherein the coherent light comprises laser light.

8. The method of claim 1, wherein a detector is located farther than one wavelength of light from the tissue and detects far field speckle.

9. The method of claim 1, wherein a detector is located within one wavelength of light from the tissue and detects near field speckle.

10. The method of claim 1, wherein the analyzing step comprises comparing each of the series of speckle patterns to a series of reference speckle patterns, and quantifying the temporal correlation differences between the speckle patterns and the reference patterns.

11. The method of claim 10, wherein the analyzing step comprises digitizing each of the speckle patterns, and the quantifying step comprises evaluating a cross-correlation between the speckle patterns and the reference patterns.

12. The method of claim 11, wherein the analyzing step further comprises determining a decorrelation rate for the speckle patterns.

13. The method of claim 10, wherein the analyzing step comprises digitizing each of the speckle patterns, and the quantifying step comprises evaluating a maximum cross-correlation between the speckle patterns and the reference patterns.

14. The method of claim 1, wherein the analyzing step further comprises analyzing spatial characteristics of the speckle pattern to deduce structural characteristics of the tissue.

15. The method of claim 14, wherein the illuminating step comprises illuminating multiple locations of the tissue in succession, the receiving step comprises forming a separate series of speckle patterns for each respective section of the tissue, and the analyzing step comprises analyzing each separate series of speckle patterns and comparing the separate series to deduce structural differences between the respective locations of the tissue.

16. The method of claim 1, wherein the analyzing step further comprises analyzing spatial characteristics of the speckle pattern to deduce biomechanical characteristics of the tissue.

17. The method of claim 1, wherein the compensating for the macroscopic motion comprises performing the receiving step during a diastole of a heartbeat.

18. The method of claim 1, wherein the macroscopic motion comprises a patient motion.

19. The method of claim 1, wherein the macroscopic motion is peristalsis.

20. The method of claim 1, wherein the receiving step comprises gathering reflected light at a light receptor and transmitting the gathered light to a detector, and wherein compensating for macroscopic motion includes coupling the receptor to the tissue.

21. The method of claim 1, wherein the compensating for the macroscopic motion includes excluding changes in the speckle patterns caused by non-random motion during the analysis step.

22. The method of claim 1, wherein the tissue comprises an atherosclerotic plaque.

23. A method of analyzing tissue, the method comprising:
    illuminating a tissue with coherent or partially coherent light;
    receiving light reflected from the tissue at a detector and forming series of speckle patterns;
    analyzing changes in the speckle patterns at time intervals sufficient to measure changes caused by a microscopic motion of objects within the tissue; and
    compensating for a macroscopic motion to isolate the microscopic motion, wherein the macroscopic motion results from a motion or the deformation of the tissue.

24. A method of analyzing a tissue structure, the method comprising:
    illuminating the tissue structure with coherent or partially coherent light;
    receiving light reflected from the tissue structure at a detector and forming a series of speckle patterns;
    gathering speckle pattern data at time intervals sufficient to measure microscopic motion within the tissue structure or adjacent tissue; and
    assessing the tissue structure by analyzing spatial characistics of the speckle pattern data to deduce structural or biomechanical characteristics of the tissue structure, wherein the tissue structure is at least one of in vivo or an internal tissue structure;
    wherein the spatial characteristics are analyzed by assessing a thickness of the tissue structure; and
    wherein the tissue structure thickness is assessed by;
    (i) measuring the decorrelation time constant $r$ as a function of $r=(x_0^2+y_0^2)^{1/2}$;
    (ii) measuring optical properties of the tissue structure; and
    (iii) comparing the measured optical properties and $\tau(r)$ to a mathematical simulation that models light remittance as a function of tissue structure thickness.

25. The method of claim 24, wherein the optical properties are measured by computing first and second order statistics of a speckle probability distribution function or by using diffuse reflectance spectrophotometry.

26. The method of claim 24, wherein the mathematical simulation is a Monte Carlo simulation or diffusion theory simulation.

27. The method of claim 24, wherein the tissue structure comprises an atherosclerotic plaque.

28. A method of analyzing tissue which comprises an atherosclerotic plague, the method comprising:
    illuminating a tissue with coherent or partially coherent light;
    receiving light reflected from the tissue at a detector and forming series of speckle patterns;
    analyzing changes in the speckle patterns at time intervals sufficient to measure changes caused by microscopic motion of objects within the tissue, wherein the tissue is at least one of in vivo or an internal tissue; and
    gathering speckle pattern data at time intervals sufficient to measure microscopic motion within a lipid pool within the atherosclerotic plaque; and assessing the atherosclerotic plaque's vulnerability to rupture from the amount of microscopic motion.

29. The method of claim 28, further comprising analyzing spatial characteristics of the speckle pattern data to deduce structural characteristics of the plaque.

30. The method of claim 29, wherein analyzing comprises assessing the thickness of the fibrous cap.

31. The method of claim 30, wherein cap thickness is assessed by
    (i) measuring the decorrelation time constant $\tau$ as a function of $r=(x_0^2+y_0^2)^{1/2}$;
    (ii) measuring optical properties of the cap; and
    (iii) comparing the measured optical properties and $\tau(r)$ to a mathematical simulation that models light remittance as a function of cap layer thickness.

32. The method of claim 31, wherein the optical properties are measured by computing first and second order statistics of a speckle probability distribution function or by using diffuse reflectance spectrophotometry.

33. The method of claim 31, wherein the mathematical simulation is a Monte Carlo simulation or diffusion theory simulation.

34. The method of claim 30, wherein a plaque is considered vulnerable to rupture if the thickness of the fibrous cap is less than about 60 microns.

35. The method of claim 30, wherein thickness of the fibrous cap is assessed by analyzing variation of $\tau$ as a function of distance from a center of the speckle pattern as a function of $(x_0^2+y_0^2)^{1/2}$.

36. The method of claim 29, wherein analyzing comprises assessing the viscosity of the lipid pool.

37. The method of claim 28, wherein the microscopic motion is Brownian motion or cellular motion.

38. A method of analyzing tissue, the method comprising:
illuminating a tissue with coherent or partially coherent light, wherein the tissue comprises an atherosclerotic plaque;
receiving light reflected from the tissue at a detector and forming series of speckle patterns; and
analyzing changes in the speckle patterns at time intervals sufficient to measure changes caused by microscopic motion within a lipid pool within the atherosclerotic plaque; and assessing the atherosclerotic plaque's vulnerability to rupture from the amount of microscopic motion, wherein the plaque is considered vulnerable to rupture if the viscosity of the lipid pool has a time constant of less than about 200 milliseconds.

39. A method of analyzing tissue, the method comprising:
illuminating a tissue with coherent or partially coherent light, wherein the tissue comprises an atherosclerotic plaque;
receiving light reflected from the tissue at a detector and forming series of speckle patterns; and
analyzing changes in the speckle patterns at time intervals sufficient to measure changes caused by microscopic motion within a lipid pool within the atherosclerotic plaque; and assessing the atherosclerotic plaque's vulnerability to rupture from the amount of microscopic motion, wherein the plaque is considered likely to rupture if the viscosity of the lipid pool has a time constant of less than about 100 milliseconds.

40. A The method of analyzing a tissue structure of which comprises an atherosclerotic plaque, the method comprising:
illuminating the tissue structure with coherent or partially coherent light;
receiving light reflected from the tissue structure at a detector and forming a series of speckle patterns;
gathering speckle pattern data at time intervals sufficient to measure microscopic motion within the tissue structure or adjacent tissue; and
assessing the tissue structure by analyzing spatial characteristics of the speckle pattern data to deduce structural or biomechanical characteristics of the tissue structure, wherein the tissue structure is at least one of in vivo or an internal tissue structure, wherein tissue structure thickness is assessed by analyzing variation of $\tau$ as a function of distance from a center of the speckle pattern as a function of $(x_0^2 + y_0^2)^{1/2}$.

41. A method of analyzing tissue, comprising:
illuminating a tissue with coherent or partially coherent light;
receiving light reflected from the tissue at a detector and forming series of speckle patterns; and
analyzing changes in the speckle patterns at time intervals sufficient to measure changes caused by microscopic motion of objects within the tissue, wherein the tissue is at least one of in vivo or an internal tissue, wherein the analyzing step comprises measuring biomechanical properties of the tissue in three dimensions.

42. A method of analyzing a tissue structure, comprising:
illuminating the tissue structure with coherent or partially coherent light;
receiving light reflected from the tissue structure at a detector and forming a series of speckle patterns;
gathering speckle pattern data at time intervals sufficient to measure microscopic motion within the tissue structure or adjacent tissue; and
assessing the tissue structure by analyzing spatial characteristics of the speckle pattern data to deduce structural or biomechanical characteristics of the tissue structure, wherein the tissue structure is at least one of in vivo or an internal tissue structure, wherein the analysis of the special characteristics includes a measurement of biomechanical properties of the tissue in three dimensions.

43. A method of analyzing tissue, comprising:
illuminating a tissue with coherent or partially coherent light;
receiving light reflected from the tissue at a detector and forming series of speckle patterns; and
analyzing changes in the speckle patterns at time intervals sufficient to measure changes caused by microscopic motion of objects within the tissue, wherein the tissue is at least one of in vivo or an internal tissue, wherein the analyzing step comprises determining a collagen content of the tissue.

44. A method of analyzing tissue, comprising:
illuminating a tissue with coherent or partially coherent light;
receiving light reflected from the tissue at a detector and forming series of speckle patterns; and
analyzing changes in the speckle patterns at time intervals sufficient to measure changes caused by microscopic motion of objects within the tissue, wherein the tissue is at least one of in vivo or an internal tissue, wherein the analyzing step comprises determining a viscosity of a lipid pool within the tissue.

45. A method of analyzing a tissue structure, comprising:
illuminating the tissue structure with coherent or partially coherent light;
receiving light reflected from the tissue structure at a detector and forming a series of speckle patterns;
gathering speckle pattern data at time intervals sufficient to measure microscopic motion within the tissue structure or adjacent tissue; and
assessing the tissue structure by analyzing spatial characteristics of the speckle pattern data to deduce structural or biomechanical characteristics of the tissue structure, wherein the tissue structure is at least one of in vivo or an internal tissue structure, wherein the analysis of the special characteristics includes a determination of collagen content of the tissue.

46. A method of analyzing a tissue structure, comprising:
illuminating the tissue structure with coherent or partially coherent light;
receiving light reflected from the tissue structure at a detector and forming a series of speckle patterns;
gathering speckle pattern data at time intervals sufficient to measure microscopic motion within the tissue structure or adjacent tissue; and
assessing the tissue structure by analyzing spatial characteristics of the speckle pattern data to deduce structural or biomechanical characteristics of the tissue structure, wherein the tissue structure is at least one of in vivo or an internal tissue structure, wherein the analysis of the special characteristics includes a determination of analyzing comprises determining a viscosity of a lipid pool within the tissue.

47. A method of analyzing tissue, the method comprising:
illuminating a tissue with coherent or partially coherent light;
receiving light reflected from the tissue at a detector and forming series of speckle patterns;
analyzing changes in the speckle patterns at time intervals sufficient to measure changes caused by microscopic motion of objects within the tissue; and at least partially replacing blood provided in or adjacent to the tissue with at least partially transparent solution.

48. A method of analyzing tissue, the method comprising:
illuminating a tissue with coherent or partially coherent light;
receiving light reflected from the tissue at a detector and forming series of speckle patterns;
analyzing changes in the speckle patterns at time intervals sufficient to measure changes caused by microscopic motion of objects within the tissue;
compensating for a macroscopic motion to isolate the microscopic motion, wherein the macroscopic motion results from a motion or the deformation of the tissue; and
at least partially replacing blood provided in or adjacent to the tissue with at least partially transparent solution.

49. A method of analyzing a tissue structure, comprising:
illuminating the tissue structure with coherent or partially coherent light;
receiving light reflected from the tissue structure at a detector and forming a series of speckle patterns;
gathering speckle pattern data at time intervals sufficient to measure microscopic motion within the tissue structure or adjacent tissue;
assessing the tissue structure by analyzing spatial characteristics of the speckle pattern data to deduce structural or biomechanical characteristics of the tissue structure, wherein the tissue structure is at least one of in vivo or an internal tissue structure; and
compensating for macroscopic motion to isolate the microscopic motion.

50. A method of analyzing a tissue structure, comprising:
illuminating the tissue structure with coherent or partially coherent light;
receiving light reflected from the tissue structure at a detector and forming a series of speckle patterns;
gathering speckle pattern data at time intervals sufficient to measure microscopic motion within the tissue structure or adjacent tissue;
assessing the tissue structure by analyzing spatial characteristics of the speckle pattern data to deduce structural or biomechanical characteristics of the tissue structure, wherein the tissue structure is at least one of in vivo or an internal tissue structure, wherein the tissue structure comprises an atherosclerotic plaque; and
gathering speckle pattern data at time intervals sufficient to measure microscopic motion within a lipid pool within the atherosclerotic plaque; and assessing the atherosclerotic plaque's vulnerability to rupture from the amount of microscopic motion.

* * * * *